United States Patent
Ter Meulen et al.

(10) Patent No.: US 10,584,356 B2
(45) Date of Patent: *Mar. 10, 2020

(54) MULTIGENOME RETROVIRAL VECTOR PREPARATIONS AND METHODS AND SYSTEMS FOR PRODUCING AND USING SAME

(71) Applicant: IMMUNE DESIGN CORP., Seattle, WA (US)

(72) Inventors: Jan Henrik Ter Meulen, Mercer Island, WA (US); Peter Lars Aksel Berglund, Seattle, WA (US)

(73) Assignee: IMMUNE DESIGN CORP., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/211,997

(22) Filed: Dec. 6, 2018

(65) Prior Publication Data

US 2019/0127759 A1   May 2, 2019

Related U.S. Application Data

(63) Continuation of application No. 15/439,324, filed on Feb. 22, 2017, now Pat. No. 10,179,919.

(60) Provisional application No. 62/410,633, filed on Oct. 20, 2016, provisional application No. 62/371,513, filed on Aug. 5, 2016, provisional application No. 62/298,948, filed on Feb. 23, 2016.

(51) Int. Cl.
| | | |
|---|---|---|
| A61K 39/395 | (2006.01) | |
| A61K 39/00 | (2006.01) | |
| C07K 16/40 | (2006.01) | |
| C07K 16/18 | (2006.01) | |
| C07K 14/47 | (2006.01) | |
| C12N 15/86 | (2006.01) | |
| A61K 48/00 | (2006.01) | |
| C07K 14/005 | (2006.01) | |

(52) U.S. Cl.
CPC .......... *C12N 15/86* (2013.01); *A61K 39/0011* (2013.01); *A61K 48/005* (2013.01); *C07K 14/005* (2013.01); *C07K 14/4748* (2013.01); *A61K 2039/5256* (2013.01); *A61K 2039/70* (2013.01); *C12N 2740/15043* (2013.01); *C12N 2740/15052* (2013.01); *C12N 2770/36122* (2013.01); *C12N 2810/609* (2013.01)

(58) Field of Classification Search
CPC ................ C07K 2319/00; C07K 16/18; C07K 2317/24; C07K 2317/33; C07K 2317/76
See application file for complete search history.

(56) References Cited

U.S. PATENT DOCUMENTS

| | | |
|---|---|---|
| 4,886,499 A | 12/1989 | Cirelli et al. |
| 4,937,190 A | 6/1990 | Palmenberg et al. |
| 5,057,540 A | 10/1991 | Kensil et al. |
| 5,168,062 A | 12/1992 | Stinski |
| 5,279,552 A | 1/1994 | Magnet |
| 5,328,483 A | 7/1994 | Jacoby |
| 5,385,839 A | 1/1995 | Stinski |
| 5,510,474 A | 4/1996 | Quail et al. |
| 5,843,728 A | 12/1998 | Seed et al. |
| 5,848,991 A | 12/1998 | Gross et al. |
| 5,997,501 A | 12/1999 | Gross et al. |
| 6,365,150 B1 | 4/2002 | Leboulch et al. |
| 6,392,013 B1 | 5/2002 | Seed et al. |
| 6,410,319 B1 | 6/2002 | Raubitschek et al. |
| 6,494,865 B1 | 12/2002 | Alchas |
| 6,569,143 B2 | 5/2003 | Alchas et al. |
| 6,670,349 B1 | 12/2003 | Nyce |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,808,506 B2 | 10/2004 | Lastovich et al. |
| 6,955,919 B2 | 10/2005 | Leboulch et al. |
| 6,971,999 B2 | 12/2005 | Py et al. |
| 7,047,070 B2 | 5/2006 | Wilkinson et al. |
| 7,083,592 B2 | 8/2006 | Lastovich et al. |
| 7,083,599 B2 | 8/2006 | Alchas et al. |
| 7,108,679 B2 | 9/2006 | Alchas |
| 7,115,108 B2 | 10/2006 | Wilkinson et al. |
| 7,241,275 B2 | 7/2007 | Alchas et al. |
| 7,265,209 B2 | 9/2007 | Jensen |
| 7,311,907 B2 | 12/2007 | Leboulch et al. |
| 7,446,179 B2 | 11/2008 | Jensen et al. |
| 7,446,190 B2 | 11/2008 | Sadelain et al. |
| 7,741,465 B1 | 6/2010 | Eshhar et al. |
| 7,994,298 B2 | 8/2011 | Zhang et al. |
| 8,034,620 B2 | 10/2011 | Leboulch et al. |
| 8,187,872 B2 | 5/2012 | Allen et al. |
| 8,252,914 B2 | 8/2012 | Zhang et al. |

(Continued)

FOREIGN PATENT DOCUMENTS

| | | |
|---|---|---|
| GB | 2220211 A | 1/1990 |
| WO | WO-96/10419 A2 | 4/1996 |

(Continued)

OTHER PUBLICATIONS

U.S. Appl. No. 11/446,353, filed Jun. 1, 2006, US-2007-0020238-A1.

(Continued)

*Primary Examiner* — Barry A Chestnut
(74) *Attorney, Agent, or Firm* — Marshall, Gerstein & Borun LLP

(57) ABSTRACT

The present invention provides novel multigenome retroviral vectors, methods and packaging systems for making such retroviral vectors and methods of use.

25 Claims, 13 Drawing Sheets

Specification includes a Sequence Listing.

(56) References Cited

U.S. PATENT DOCUMENTS

| | | | |
|---|---|---|---|
| 8,273,345 | B2 | 9/2012 | Wang et al. |
| 8,273,361 | B2 | 9/2012 | Reed et al. |
| 8,323,662 | B1 | 12/2012 | Nicolai et al. |
| 8,329,162 | B2 | 12/2012 | Wang et al. |
| 8,343,512 | B2 | 1/2013 | Reed et al. |
| 8,372,390 | B2 | 2/2013 | Wang et al. |
| 8,609,114 | B2 | 12/2013 | Reed |
| 8,715,640 | B2 | 5/2014 | Wang et al. |
| 8,741,576 | B2 | 6/2014 | Tangri et al. |
| 8,821,856 | B2 | 9/2014 | Baltimore et al. |
| 8,840,908 | B2 | 9/2014 | Reed et al. |
| 8,906,359 | B2 | 12/2014 | Wang et al. |
| 9,303,072 | B2 | 4/2016 | Wang et al. |
| 9,713,635 | B2 | 7/2017 | Nicolai et al. |
| 9,840,721 | B2 | 12/2017 | Wang et al. |
| 9,907,845 | B2 | 3/2018 | Reed et al. |
| 9,950,063 | B2 | 4/2018 | Reed et al. |
| 2007/0020238 | A1 | 1/2007 | Baltimore et al. |
| 2008/0019998 | A1 | 1/2008 | Wang et al. |
| 2008/0131466 | A1 | 6/2008 | Reed et al. |
| 2009/0181078 | A1 | 7/2009 | Reed et al. |
| 2010/0120122 | A1 | 5/2010 | Wang et al. |
| 2010/0120140 | A1 | 5/2010 | Wang et al. |
| 2011/0014274 | A1 | 1/2011 | Reed et al. |
| 2011/0064763 | A1 | 3/2011 | Allen et al. |
| 2011/0070290 | A1 | 3/2011 | Reed et al. |
| 2011/0212530 | A1 | 9/2011 | Baltimore et al. |
| 2012/0039932 | A1 | 2/2012 | Allen et al. |
| 2012/0039994 | A1 | 2/2012 | Reed et al. |
| 2012/0070462 | A1 | 3/2012 | Wang et al. |
| 2013/0084307 | A1 | 4/2013 | Reed et al. |
| 2013/0230554 | A1 | 9/2013 | Wang et al. |
| 2013/0288368 | A1 | 10/2013 | June et al. |
| 2014/0037691 | A1 | 2/2014 | Reed et al. |
| 2014/0193459 | A1 | 7/2014 | Reed et al. |
| 2014/0341970 | A1 | 11/2014 | Reed et al. |
| 2015/0050307 | A1 | 2/2015 | Nicolai et al. |
| 2015/0175667 | A1 | 6/2015 | Wang et al. |
| 2015/0203886 | A1 | 7/2015 | Kishi et al. |
| 2015/0335736 | A1 | 11/2015 | Reed et al. |
| 2016/0058860 | A1 | 3/2016 | Reed et al. |
| 2016/0076055 | A1 | 3/2016 | Allen et al. |
| 2016/0222409 | A1 | 8/2016 | Baltimore et al. |
| 2016/0340692 | A1 | 11/2016 | Wang et al. |
| 2018/0055921 | A1 | 3/2018 | Nicolai et al. |

FOREIGN PATENT DOCUMENTS

| | | |
|---|---|---|
| WO | WO-1998/032869 A1 | 7/1998 |
| WO | WO-2009/035528 A2 | 3/2009 |
| WO | WO-2009/076524 A2 | 6/2009 |
| WO | WO-2011011584 A1 | 1/2011 |
| WO | WO-2012/079000 A1 | 6/2012 |
| WO | WO-2012/129514 A1 | 9/2012 |
| WO | WO-2013/076309 A1 | 5/2013 |
| WO | WO-2013/149167 A1 | 10/2013 |

OTHER PUBLICATIONS

U.S. Appl. No. 11/781,865, filed Jul. 23, 2007, US-2008-0019998-A1, U.S. Pat. No. 8,329,162.
U.S. Appl. No. 11/862,122, filed Sep. 26, 2007, US-2008-0131466-A1, U.S. Pat. No. 8,273,361.
U.S. Appl. No. 12/134,127, filed Jun. 5, 2008.
U.S. Appl. No. 12/154,663, filed May 22, 2008.
U.S. Appl. No. 12/351,710, filed Jan. 9, 2009, US-2009-0181078-A1.
U.S. Appl. No. 12/688,689, filed Jan. 15, 2010, US-2010-0120122-A1, U.S. Pat. No. 8,715,640.
U.S. Appl. No. 12/688,779, filed Jan. 15, 2010, US-2010-0120140-A1, U.S. Pat. No. 8,372,390.
U.S. Appl. No. 12/842,609, filed Jul. 23, 2010, US-2011-0064763-A1.
U.S. Appl. No. 12/843,395, filed Jul. 26, 2010, US-2011-0014274-A1.
U.S. Appl. No. 12/843,398, filed Jul. 26, 2010, US-2011-0070290-A1.
U.S. Appl. No. 13/041,115, filed Mar. 4, 2011, US-2011-0212530-A1, U.S. Pat. No. 8,821,856.
U.S. Appl. No. 13/277,900, filed Oct. 20, 2011, US-2012-0039932-A1, U.S. Pat. No. 8,187,872.
U.S. Appl. No. 13/277,919, filed Oct. 20, 2011, US-2012-0039994-A1, U.S. Pat. No. 8,343,512.
U.S. Appl. No. 13/301,545, filed Nov. 21, 2011, US-2012-0070462-A1, U.S. Pat. No. 8,273,345.
U.S. Appl. No. 13/436,472, filed Mar. 30, 2012, U.S. Pat. No. 8,323,662.
U.S. Appl. No. 13/599,695, filed Aug. 30, 2012, U.S. Pat. No. 8,609,114.
U.S. Appl. No. 13/599,701, filed Aug. 30, 2012, US-2013-0084307-A1, U.S. Pat. No. 8,840,908.
U.S. Appl. No. 13/886,666, filed May 3, 2013, US-2014-0193459-A1.
U.S. Appl. No. 13/887,908, filed May 6, 2013, US-2013-0230554-A1, U.S. Pat. No. 8,906,359.
U.S. Appl. No. 13/930,953, filed Jun. 28, 2013, US-2014-0037691-A1, U.S. Pat. No. 9,987,355.
U.S. Appl. No. 14/096,582, filed Dec. 4, 2013, US-2014-0341970-A1, U.S. Pat. No. 9,907,845.
U.S. Appl. No. 14/338,947, filed Jul. 23, 2014, US-2016-0222409-A1, U.S. Pat. No. 9,994,867.
U.S. Appl. No. 14/389,131, filed Sep. 29, 2014, US-2015-0050307-A1, U.S. Pat. No. 9,713,635.
U.S. Appl. No. 14/532,371, filed Nov. 4, 2014, US-2015-0175667-A1, U.S. Pat. No. 9,303,072.
U.S. Appl. No. 14/581,062, filed Dec. 23, 2014, US-2015-0335736-A1, U.S. Pat. No. 9,950,063.
U.S. Appl. No. 14/849,212, filed Sep. 9, 2015, US-2016-0058860-A1.
U.S. Appl. No. 14/872,633, filed Oct. 1, 2015, US-2016-0076055-A1.
U.S. Appl. No. 15/051,907, filed Feb. 24, 2016, US-2016-0340692-A1, U.S. Pat. No. 9,840,721.
U.S. Appl. No. 15/612,192, filed Jun. 2, 2017, US-2018-0055921-A1, U.S. Pat. No. 10,391,157.
U.S. Appl. No. 15/820,741, filed Nov. 22, 2017, US-2018-0179555-A1, U.S. Pat. No. 10,266,847.
U.S. Appl. No. 15/823,852, filed Nov. 28, 2017, US-2018-0221470-A1.
U.S. Appl. No. 15/868,460, filed Jan. 11, 2018, US-2018-0169226-A1.
U.S. Appl. No. 15/875,517, filed Jan. 19, 2018, US-2018-0236063-A1.
Adra et al., Cloning and expression of the mouse pgk-1 gene and the nucleotide sequence of its promoter, Gene, 60(1):65-74 (1987).
Albershardt et al., LV305, a dendritic cell-targeting integration-deficient ZVex(TM)-based lentiviral vector encoding NY-ESO-1, induces potent anti-tumor immune response, Mol. Ther. Oncolytics, 3:16010 (2016).
Apolonia, Development and application of non-integrating lentiviral vectors for gene therapy, Thesis submitted to University College London, pp. 82-97 (Apr. 2009).
Baig et al., Regulation of primate lentiviral RNA dimerization by structural entrapment, Retrovirology, 5:65 (2008).
Banchereau et al., Dendritic cells as vectors for therapy, Cell, 106(3):271-4 (2001).
Batchu et al., High-level expression of cancer/testis antigen NY-ESO-1 and human granulocyte-macrophage colony-stimulating factor in dendritic cells with a bicistronic retroviral vector, Hum. Gene Ther., 14(14):1333-45 (2003).
Bernard et al., Mutations in the E2 glycoprotein of Venezuelan equine encephalitis virus confer heparan sulfate interaction, low morbidity, and rapid clearance from blood of mice, Virology, 276(1):93-103 (2000).

Boon et al., Tumor antigens recognized by T lymphocytes, Annu. Rev. Immunol., 12:337-65 (1994).

(56) References Cited

OTHER PUBLICATIONS

Boshart et al., A very strong enhancer is located upstream of an immediate early gene of human cytomegalovirus, Cell, 41(2):521-30 (1985).
Brown et al., Structure-based mutagenesis of the human immunodeficiency virus type 1 DNA attachment site: effects on integration and cDNA synthesis, J. Virol., 73(11):9011-20 (1999).
Byrnes et al., Binding of Sindbis virus to cell surface heparan sulfate, J. Virol., 72(9):7349-56 (1998).
Cann (ed.), RNA Viruses: A Practical Approach, Oxford University Press (2000). [Table of Contents Only].
Chen et al., High efficiency of HIV-1 genomic RNA packaging and heterozygote formation revealed by single virion analysis, Proc. Natl. Acad. Sci. USA, 106(32):13535-40 (2009).
Chen et al., Oncology meets immunology: the cancer-immunity cycle, Immunity, 39(1):1-10 (2013).
Coffin, "Structure of the Retroviral Genome", IN: Weiss et al. (eds.), RNA Tumor Viruses, 2nd ed., Cold Spring Harbor Laboratory (1982).
Dahlberg et al., Micromanagement during the innate immune response, Sci STKE, 2007(387):pe25 (2007).
De Felipe et al., Targeting of proteins derived from self-processing polyproteins containing multiple signal sequences, Traffic, 5(8):616-26 (2004).
Dekhatiarenko et al., The context of gene expression defines the immunodominance hierarchy of cytomegalovirus antigens, J. Immunol., 190(7):3399-409 (2013).
Deleage et al., Defining HIV and SIV Reservoirs in Lymphoid Tissues, Pathog. Immun., 1(1):68-106 (2016).
Dilley et al., Determining the frequency and mechanisms of HIV-1 and HIV-2 RNA copackaging by single-virion analysis, J. Virol., 85(20):10499-508 (2011).
Dobson et al., Conservation of high efficiency promoter sequences in *Saccharomyces cerevisiae*, Nucleic Acids Res., 10(8):2625-37 (1982).
Déglon et al., Self-inactivating lentiviral vectors with enhanced transgene expression as potential gene transfer system in Parkinson's disease, Hum. Gene Ther., 11(1):179-90 (2000).
Engelman et al., Multiple effects of mutations in human immunodeficiency virus type 1 integrase on viral replication, J. Virol., 69(5):2729-36 (1995).
Fang et al., Stable antibody expression at therapeutic levels using the 2A peptide, Nat. Biotechnol., 23(5):584-90 (2005).
Farrington et al., Competition for antigen at the level of the APC is a major determinant of immunodominance during memory inflation in murine cytomegalovirus infection, J. Immunol., 190(7):3410-6 (2013).
Fire et al., Potent and specific genetic interference by double-stranded RNA in Caenorhabditis elegans, Nature, 391(6669):806-11 (1998).
Flynn et al., Nonrandom dimerization of murine leukemia virus genomic RNAs, J. Virol., 78(22):12129-39 (2004).
Gabitzsch et al., The generation and analyses of a novel combination of recombinant adenovirus vaccines targeting three tumor antigens as an immunotherapeutic, Oncotarget, 6(31):31344-59 (2015).
Geijtenbeek et al., Self- and nonself-recognition by C-type lectins on dendritic cells, Annu. Rev. Immunol., 22:33-54 (2004).
Graham et al., A new technique for the assay of infectivity of human adenovirus 5 DNA, Virology, 52(2):456-67 (1973).
Gunning et al., A human beta-actin expression vector system directs high-level accumulation of antisense transcripts, Proc. Natl. Acad. Sci. USA, 84(14):4831-5 (1987).
Hamilton et al., Cancer vaccines targeting the epithelial-mesenchymal transition: tissue distribution of brachyury and other drivers of the mesenchymal-like phenotype of carcinomas, Semin. Oncol., 39(3):358-66 (2012).
Hindson et al., "High-throughput droplet digital PCR system for absolute quantitation of DNA copy number," Anal. Chem. 83(22):8604-10 (2011).

International Application No. PCT/US2017/018823, International Search Report and Written Opinion, dated May 31, 2017.
Iwakuma et al., Self-inactivating lentiviral vectors with U3 and U5 modifications, Virology, 261(1):120-32 (1999).
Jensen et al., Adjuvant activity of incomplete Freund's adjuvant, Adv. Drug Deliv. Rev., 3293):173-86 (1998).
Kensil et al., Structural and Immunological Characterization of the Vaccine Adjuvant QS-21, pp. 525-541 IN: Powell et al. (eds.), Vaccine Design: The Subunit and Adjuvant Approach, Springer (1995).
Klimstra et al., Adaptation of Sindbis virus to BHK cells selects for use of heparan sulfate as an attachment receptor, J. Virol., 72(9):7357-66 (1998).
Klimstra et al., DC-SIGN and L-SIGN can act as attachment receptors for alphaviruses and distinguish between mosquito cell- and mammalian cell-derived viruses, J. Virol., 77(22):12022-32 (2003).
Kobayashi et al., A new cloning and expression system yields and validates TCRs from blood lymphocytes of patients with cancer within 10 days, Nat. Med., 19(11):1542-6 and Supplementary Information (2013).
Kobayashi et al., A novel system for cloning human TCRs: Cutting short the way to TCR-based anticancer therapy, Oncoimmunology, 3(1):e27258 (2014).
Kreiter et al., Mutant MHC class II epitopes drive therapeutic immune responses to cancer, Nature, 520(7549):692-6 (2015).
Kuzembayeva et al., Life of psi: how full-length HIV-1 RNAs become packaged genomes in the viral particles, Virology, 454-5:362-70 (2014).
Lieberman et al., Recognition of a small number of diverse epitopes dominates the cytotoxic T lymphocytes response to HIV type 1 in an infected individual, AIDS Res. Hum. Retroviruses, 13(5):383-92 (1997).
Linnemann et al., High-throughput epitope discovery reveals frequent recognition of neo-antigens by CD4' T cells in human melanoma, Nat. Med., 21(1):81-5 (2015).
Livingston et al., The hepatitis B virus-specific CTL responses induced in humans by lipopeptide vaccination are comparable to those elicited by acute viral infection, J. Immunol., 159(3):1383-92 (1997).
Lopes et al., Immunization with a lentivector that targets tumor antigen expression to dendritic cells induces potent CD8+ and CD4+ T-cell responses, J. Virol., 82(1):86-95 (2008).
Lu et al., Structural determinants and mechanism of HIV-1 genome packaging, J. Mol. Biol., 410(4):609-33 (2011).
Martin et al., Targeting the undruggable: immunotherapy meets personalized oncology in the genomic era, Ann. Oncol., 26(12):2367-74 (2015).
McWilliams et al., Mutations in the 5' end of the human immunodeficiency virus type 1 polypurine tract affect RNase H cleavage specificity and virus titer, J. Virol., 77(20):11150-7 (2003).
Meissner et al., Development of an inducible pol III transcription system essentially requiring a mutated form of the TATA-binding protein, Nucleic Acids Res., 29(8):1672-82 (2001).
Men et al., Assessment of immunogenicity of human Melan-A peptide analogues in HLA-A*0201/Kb transgenic mice, J. Immunol., 162(6):3566-73 (1999).
Menendez-Arias et al., Cytotoxic T-lymphocyte responses to HIV-1 reverse transcriptase (review), Viral Immunol., 11(4):167-81 (1998).
Miyoshi et al., Development of a self-inactivating lentivirus vector, J. Virol., 72(10):8150-7 (1998).
Moore et al., Dimer initiation signal of human immunodeficiency virus type 1: its role in partner selection during RNA copackaging and its effects on recombination, J. Virol., 81(8):4002-11 (2007).
Moore et al., HIV-1 RNA dimerization: It takes two to tango, AIDS Rev., 11(2):91-102 (2009).
Mukhopadhyay et al., A structural perspective of the flavivirus life cycle, Nat. Rev. Microbiol., 3(1):13-22 (2005).
Nightingale et al., Transient gene expression by nonintegrating lentiviral vectors, Mol. Ther., 13(6):1121-32 (2006).
Nikolaitchik et al., Multiple barriers to recombination between divergent HIV-1 variants revealed by a dual-marker recombination assay, J. Mol. Biol., 407(4):521-31 (2011).

(56) References Cited

OTHER PUBLICATIONS

Ohkawa et al., Control of the functional activity of an antisense RNA by a tetracycline-responsive derivative of the human U6 snRNA promoter, Hum. Gene Ther., 11(4):577-85 (2000).
Palena et al., Overexpression of the EMT driver brachyury in breast carcinomas: association with poor prognosis, J. Natl. Cancer Inst., 106(5) (2014).
Pardoll, The blockade of immune checkpoints in cancer immunotherapy, Nat. Rev. Cancer, 12(4):252-64 (2012).
Paule et al., Survey and summary: transcription by RNA polymerases I and III, Nucleic Acids Res., 28(6):1283-98 (2000).
Pfeifer et al., Gene therapy: promises and problems, Annu. Rev. Genomics Hum. Genet., 2:177-211 (2001).
Philpott et al., Use of nonintegrating lentiviral vectors for gene therapy, Hum. Gene Ther., 18(6):483-9 (2007).
Pinheiro et al., Evaluation of a droplet digital polymerase chain reaction format for DNA number quantification, Anal. Chem., 8492):1003-11 (2012).
Player et al., Single-copy gene detection using branched DNA (bDNA) in situ hybridization, J. Histochem. Cytochem., 49(5):603-12 (2001).
Powell et al., Sequence and structural determinants required for priming of plus-strand DNA synthesis by the human immunodeficiency virus type 1 polypurine tract, J. Virol., 70(8):5288-96 (1996).
Rajasagi et al., Systematic identification of personal tumor-specific neoantigens in chronic lymphocytic leukemia, Blood, 124(3):453-62 (2014).
Reiser et al., Development of multigene and regulated lentivirus vectors, J. Virol., 74(22):10589-99 (2000).
Renkvist et al., A listing of human tumor antigens recognized by T cells, Cancer Immunol. Immunother., 50(1):3-15 (2001).
Rivoltini et al., A superagonist variant of peptide MART1/Melan A27-35 elicits anti-melanoma CD8+ T cells with enhanced functional characteristics: implication for more effective immunotherapy, Cancer Res., 59(2):301-6 (1999).
Roselli et al., Brachyury, a driver of the epithelial-mesenchymal transition, is overexpressed in human lung tumors: an opportunity for novel interventions against lung cancer, Clin. Cancer Res., 18(14):3868-79 (2012).
Sambrook et al. Molecular Cloning: A Laboratory Manual, 3d ed., Cold Spring Harbor Laboratory Press, NY 2001).
Schatzlein, Non-viral vectors in cancer gene therapy: principles and progress, Anticancer Drugs, 12(4):275-304 (2001).
Scherer et al., High epitope expression levels increase competition between T cells, PLoS Comput. Biol., 2(8):e109 (2006).
Selby et al., Hepatitis C virus envelope glycoprotein E1 originates in the endoplasmic reticulum and requires cytoplasmic processing for presentation by class I MHC molecules, J. Immunol., 162(2):669-76 (1999).
Singer-Sam et al., Sequence of the promoter region of the gene for human X-linked 3-phosphoglycerate kinase, Gene, 32(3):409-17 (1984).
Stoute et al., A preliminary evaluation of a recombinant circumsporozoite protein vaccine against Plasmodium falciparum malaria. RTS,S Malaria Vaccine Evaluation Group, N. Engl. J. Med., 336(2):86-91 (1997).
Stripecke et al., Lentiviral vectors for efficient delivery of CD80 and granulocyte-macrophage-colony-stimulating factor in human acute lymphoblastic leukemia and acute myeloid leukemia cells to induce antileukemic immune responses, Blood, 96(4):1317-26 (2000).
Szymczak et al., Correction of multi-gene deficiency in vivo using a single 'self-cleaving' 2A peptide-based retroviral vector, Nat. Biotechnol., 22(5):589-94 (2004).
Taganov et al., MicroRNAs and immunity: tiny players in a big field, Immunity, 26(2):133-7 (2007).
Thomsen et al., Promoter-regulatory region of the major immediate early gene of human cytomegalovirus, Proc. Natl. Acad. Sci. USA, 81(3):659-63 (1984).
Tiemann et al., RNAi-based therapeutics-current status, challenges and prospects, EMBO Mol. Med., 1(3):142-51 (2009).
Tran et al., Conserved determinants of lentiviral genome dimerization, Retrovirology, 12:83 (2015).
Trang et al., MicroRNAs as potential cancer therapeutics, Oncogene, 27 Suppl 2:S52-7 (2008).
Wang et al., High-affinity laminin receptor is a receptor for Sindbis virus in mammalian cells, J. Virol., 66(8):4992-5001 (1992).
Wang et al., RNAscope: a novel in situ RNA analysis platform for formalin-fixed, paraffin-embedded tissues, J. Mol. Diagn., 1491):22-9 (2012).
Wang et al., The stimulation of low-affinity, nontolerized clones by heteroclitic antigen analogues causes the breaking of tolerance established to an immunodominant T cell epitope, J. Exp. Med., 190(7):983-94 (1999).
Wigler et al., DNA-mediated transfer of the adenine phosphoribosyltransferase locus into mammalian cells, Proc. Natl. Acad. Sci. USA, 76(3):1373-6 (1979).
Zaremba et al., Identification of an enhancer agonist cytotoxic T lymphocyte peptide from human carcinoembryonic antigen, Cancer Res., 57(20):4570-7 (1997).
Zufferey et al., Self-inactivating lentivirus vector for safe and efficient in vivo gene delivery, J. Virol., 72(12):9873-80 (1998).
Zufferey et al., Woodchuck Hepatitis Virus Posttranscriptional Regulatory Element Enhances Expression of Transgenes Delivered by Retroviral Vectors, J. Virol., 73(4):2886-92 (1999).
Zügel et al., Termination of peripheral tolerance to a T cell epitope by heteroclitic antigen analogues, J. Immunol., 161(4):1705-9 (1998).

SEQUENCE LISTING

```
<160> NUMBER OF SEQ ID NOS: 14

<210> SEQ ID NO 1
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 1 gcgcgc                                                              6

<210> SEQ ID NO 2
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 2 gcccgg                                                              6

<210> SEQ ID NO 3
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 3 ccgggc                                                              6

<210> SEQ ID NO 4
<211> LENGTH: 6
```

-continued

```
<212> TYPE: DNA
<213> ORGANISM: Artificial Sequence
<220> FEATURE:
<223> OTHER INFORMATION: Dimer initiation site (DIS)

<400> SEQUENCE: 4 gggggg                                                              6

<210> SEQ ID NO 5
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 5 cccccc                                                              6

<210> SEQ ID NO 6
<211> LENGTH: 6
<212> TYPE: RNA
<213> ORGANISM: Artificial Sequence
<220> FEATURE:
<223> OTHER INFORMATION: Dimer initiation site (DIS)

<400> SEQUENCE: 6 gugcac                                                              6

<210> SEQ ID NO 7
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 7 gcgcgg                                                              6

<210> SEQ ID NO 8
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 8 cgcgcc                                                              6

<210> SEQ ID NO 9
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 9 gggcgg                                                              6

<210> SEQ ID NO 10
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 10
```

```
<210> SEQ ID NO 11
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 11 cgcgcg                                                                     6

<210> SEQ ID NO 12
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 12 cgggcc                                                                     6

<210> SEQ ID NO 13
<211> LENGTH: 6
<212> TYPE: DNA
<213> ORGANISM: Artificial Sequence
<220> FEATURE:
<223> OTHER INFORMATION: Dimer initiation site (DIS)

<400> SEQUENCE: 13 ggcccg                                                                     6

<210> SEQ ID NO 14
<211> LENGTH: 6
<212> TYPE: RNA
<213> ORGANISM: Artificial Sequence
<220> FEATURE:
<223> OTHER INFORMATION: Dimer initiation site (DIS)

<400> SEQUENCE: 14 cacgug                                                                     6
```

MULTIGENOME RETROVIRAL VECTOR PREPARATIONS AND METHODS AND SYSTEMS FOR PRODUCING AND USING SAME

CROSS-REFERENCE TO RELATED APPLICATIONS

This application is a continuation application of U.S. application Ser. No. 15/439,324 filed Feb. 22, 2017, which claims priority to U.S. Provisional Application No. 62/410,633 filed Oct. 20, 2016; U.S. Provisional Application No. 62/371,513 filed Aug. 5, 2016; and U.S. Provisional Application No. 62/298,948 filed Feb. 23, 2016, incorporated herein by reference in its entirety.

INCORPORATION BY REFERENCE OF MATERIALS SUBMITTED ELECTRONICALLY

This application contains, as a separate part of the disclosure, a Sequence Listing in computer readable form (Filename: 50496A_Seqlisting.txt; Size: 3,205 bytes; Created: Dec. 5, 2018), which is incorporated by reference in its entirety.

FIELD

The present invention provides novel multigenome retroviral vectors and methods and packaging systems for making such retroviral vectors.

BACKGROUND

Retroviral vectors are a common tool for gene delivery in that the ability of retroviral vectors to deliver a nucleic acid of interest into a broad range of cells makes them well suited for transferring genes to a cell. Retroviral vectors have been used in gene therapy as well as for therapeutic vaccines for infectious diseases and cancer. However, expression of multiple transgenes from a single retroviral vector genome (multicistronic expression) often results in unequal expression levels of the recombinant proteins due to, for example, competition of the different promoters for transcription factors or variability in function of internal ribosome entry site (IRES). In the case of delivery of nucleic acids to dendritic cells, interference phenomena on the level of expression, antigen processing or presentation, especially with certain tumor antigens, have been observed.

The present invention provides for improved retroviral vectors and methods of making same that facilitate expression of multiple transgenes.

SUMMARY OF THE INVENTION

One aspect of the present disclosure provides a recombinant multigenome retroviral vector preparation comprising: a) a first retroviral particle comprising two copies of a first retroviral vector genome comprising a first sequence of interest; b) a second retroviral particle comprising two copies of a second retroviral vector genome comprising a second sequence of interest; c) a third retroviral particle comprising one copy of the first retroviral vector genome comprising a first sequence of interest and one copy of the second retroviral vector genome comprising a second sequence of interest; wherein the first and second sequences of interest are different; wherein the first and second retroviral vector genomes are defective retroviral genomes (e.g., do not encode essential viral proteins, such as functional gag or pol proteins and are unable to produce infectious particles after entering a target cell) and wherein the retroviral vector preparation is pseudotyped with a heterologous envelope glycoprotein. In certain embodiments of the recombinant multigenome retroviral vector preparations herein, the third retroviral particle makes up at least 60%, 70%, 80%, 90% or 95% of the total retroviral particles in the preparation. In another embodiment of the recombinant multigenome retroviral vector preparations described herein, the heterologous envelope glycoprotein is selected from the group consisting of VSVg, measles envelope glycoprotein, and a Sindbis envelope glycoprotein. In a particular embodiment, the heterologous envelope glycoprotein comprises a variant Sindbis virus E2 glycoprotein, and in one embodiments, the variant Sindbis virus E2 glycoprotein binds to DC-SIGN. In one embodiment, the recombinant multigenome retroviral vector preparation described herein is a lentiviral vector preparation.

In another embodiment of the recombinant multigenome retroviral vector preparation described herein, the first sequence of interest encodes a tumor-associated antigen or one or more neoantigens and the second sequence of interest encodes an immunomodulatory molecule. In another embodiment, the first sequence of interest encodes a tumor-associated antigen and the second sequence of interest encodes a different tumor-associated antigen. In a further embodiment, the first sequence of interest encodes a tumor-associated antigen and the second sequence of interest encodes one or more neoantigens. In an additional embodiment, the one or more neoantigens is derived from the tumor-associated antigen of the first sequence of interest.

In another embodiment, the recombinant multigenome retroviral vector preparations described herein further comprises: e) a fourth retroviral particle comprising two copies of a third retroviral vector genome comprising a third sequence of interest; f) a fifth retroviral particle comprising one copy of the first retroviral vector genome comprising a first sequence of interest and one copy of the third retroviral vector genome comprising the third sequence of interest; and g) a sixth retroviral particle comprising one copy of the second retroviral vector genome comprising a second sequence of interest and one copy of the third retroviral vector genome comprising the third sequence of interest. In one embodiment, the retroviral vector genomes used to generate the multigenome retroviral vector preparations herein are defective retroviral genomes (e.g., do not encode essential viral proteins, such as functional gag or pol proteins and are unable to produce infectious particles after entering a target cell).

Another aspect of the present disclosure provides a retroviral vector packaging system for producing a pseudotyped multigenome retroviral vector preparation, comprising: a) a first nucleic acid molecule encoding a viral envelope protein; b) a second nucleic acid molecule encoding gag and pol proteins; c) a third nucleic acid molecule encoding rev; d) a fourth nucleic acid molecule comprising a first lentiviral vector genome comprising a first sequence of interest; e) a fifth nucleic acid molecule comprising a second lentiviral vector genome comprising a second sequence of interest; f) optionally a sixth nucleic acid molecule encoding vpx; and g) a packaging cell or cell line. In certain embodiments of the retroviral vector packaging systems described herein, the retroviral vector preparation is a lentiviral vector preparation. In one embodiment, the vector genomes used to generate the multigenome retroviral vector preparations herein are defective retroviral genomes (e.g., do not encode essential viral proteins, such as functional gag or pol proteins and are unable to produce infectious particles after entering a target cell). In another embodiment of the retroviral vector packaging systems herein, the first sequence of interest encodes a tumor-associated antigen or one or more neoantigens and the second sequence of interest encodes an immunomodulatory molecule. In a further embodiment, the first sequence of interest encodes a tumor-associated antigen and the second sequence of interest encodes a different tumor-associated antigen. In one embodiment, the first sequence of interest encodes a tumor-associated antigen and the second sequence of interest encodes one or more neoantigens. In another embodiment of the retroviral vector packaging system of claim 13 wherein the viral envelope protein is selected from the group consisting of VSVg, measles envelope glycoprotein, and a Sindbis envelope glycoprotein. In certain embodiments, the viral envelope protein comprises a Sindbis virus E2 glycoprotein or a variant thereof capable of infecting dendritic cells. In another embodiment of the retroviral vector packaging system, equal amounts of the fourth nucleic acid molecule and the fifth nucleic acid molecule are used. In a further embodiment, the relative input ratio of the fourth nucleic acid molecule to the fifth nucleic acid molecule used in the packaging system is 60:40.

In another embodiment of the retroviral vector packaging systems described herein, the first lentiviral vector genome and the second lentiviral vector comprise a palindromic dimer initiation site (DIS) sequence. In certain embodiment, the palindromic dimer initiation site (DIS) sequence in the first lentiviral vector genome and the second lentiviral vector is the same. In another embodiment, the first lentiviral vector genome comprises a first palindromic DIS sequence and the second lentiviral vector comprise a second palindromic dimer initiation site (DIS) sequence. Thus, in certain embodiments, the retroviral vector packaging system preferentially produces homozygous retroviral vector particles. In another embodiment of the retroviral vector packaging systems described herein, the first lentiviral vector genome comprises a first DIS sequence and the second lentiviral vector comprise a second dimer initiation site (DIS) sequence wherein the first DIS sequence pairs with the second DIS sequence during packaging such that the retroviral vector packaging system preferentially produces heterozygous retroviral vector particles.

In certain embodiments of the retroviral vector packaging system described herein, the pol protein has a non-functional integrase. In one embodiment, the vector genomes used to generate the multigenome retroviral vector preparations herein are defective retroviral genomes (e.g., do not encode essential viral proteins, such as functional gag or pol proteins and are unable to produce infectious particles after entering a target cell). Thus, in certain embodiments, the vector genomes used to generate any of the multigenome vector preparations described herein do not contain sequences encoding a functional gag or pol protein.

Another aspect of the present disclosure provides a multigenome retroviral vector packaging system, comprising: a) at least two nucleic acid molecules each comprising a retroviral vector genome comprising a unique sequence of interest; b) one or more nucleic acid molecules encoding the components necessary to generate pseudotyped retroviral vector particles; c) optionally a nucleic acid molecule encoding vpx; and d) a packaging cell line. In one embodiment, the at least two retroviral vector genomes are defective retroviral genomes (e.g., do not encode essential viral proteins, such as functional gag or pol proteins and are unable to produce infectious particles after entering a target cell). In one embodiment, the multigenome retroviral vector packaging system consists of 2 to 8 nucleic acid molecules each comprising a retroviral vector genome comprising a unique sequence of interest. In certain embodiments, the unique sequences of interest are selected from the group consisting of the sequences encoding MAGEA1, MAGEA4, NYESO1, MAGEA3, MAGEA10, ScFvanti-PD1, IL12, IL23, CD40, ScFvanti-PDL1, and ScFvanti-CTLA4, or an immunogenic variant of any of the foregoing. In one embodiment, the components necessary to generate retroviral vector particles include gag, pol, rev, and envelope proteins. In a further embodiment, the packaging cell line stably expresses one or more of the components necessary to generate retroviral vector particles. In one particular embodiment of the multigenome retroviral vector packaging system, the retroviral vector genome is a lentiviral vector genome.

Another aspect of the present disclosure provides a method for producing a pseudotyped multigenome retroviral vector preparation comprising culturing a packaging cell line of the multigenome retroviral vector packaging systems described herein wherein the packaging cell line is transfected with a) at least two nucleic acid molecules each comprising a retroviral vector genome comprising a unique sequence of interest; b) one or more nucleic acid molecules encoding the components necessary to generate pseudotyped retroviral vector particles; and c) optionally a nucleic acid molecule encoding vpx, and harvesting the pseudotyped multigenome retroviral vector particles. This, one aspect of the present disclosure provides a pseudotyped multigenome retroviral vector preparation produced by this method.

Another aspect of the present disclosure provides a method of inducing an immune response in a subject comprising administering the multigenome retroviral vector preparations described herein, in certain embodiments, those preparations expressing one or more tumor antigens and/or one or more immunomodulatory molecules.

Another aspect of the present disclosure provides a method of treating cancer in a subject comprising administering the multigenome retroviral vector preparations expressing one or more tumor antigens and/or one or more immunomodulatory molecules.

A further aspect of the present disclosure provides a method for delivering and expressing multiple sequences of interest to a subject in vivo comprising administering the multigenome retroviral vector preparations described herein.

Another aspect of the present disclosure provides a recombinant multigenome retroviral vector preparation of any of the embodiments described herein for use in therapy.

Another aspect of the disclosure provides a recombinant multigenome retroviral vector preparation of any of the embodiments described herein for use in a method of treatment of a patient.

A further aspect of the disclosure provides a recombinant multigenome retroviral vector preparation of any of the embodiments described herein for use in a method of treating cancer in a patient.

Another aspect of the disclosure provides a recombinant multigenome retroviral vector preparation of any of the embodiments described herein for use in a method of stimulating an immune response in a patient.

These and other aspects of the present invention will become evident upon reference to the following detailed description and attached drawings.

BRIEF DESCRIPTION OF THE DRAWINGS

FIG. 7A: multi ICS staining of CD8+ T cells stimulated in vitro with MAGEA1 pool; FIG. 7B: multi ICS staining of CD8+ T cells stimulated in vitro with MAGEA3 pool; FIG. 7C: multi ICS staining of CD8+ T cells stimulated in vitro with MAGEA4 pool; FIG. 7D: multi ICS staining of CD8+ T cells stimulated in vitro with MAGEA10 pool.

FIG. 8A: % IFNg+ of CD8+ T cells stimulated in vitro with NYESO1 peptide pool; FIG. 8B: % IFNg+ of CD8+ T cells stimulated in vitro with MAGEA3 peptide pool; FIG. 8C: % IFNg+ of CD8+ T cells stimulated in vitro with MAGEA10 pool. % vaccine take is denoted above relevant bars. *Statistically significant using Mann-Whitney test.

FIG. 9A: GCN/GCN=lentiviral vector preparations made with a single vector genome plasmid encoding NYESO1 with wild type DIS (GCGCGC, SEQ ID NO:1); GGN/GGN=lentiviral vector preparation made with a single vector genome plasmid encoding NYESO1 with mutated DIS (GGGGGG, SEQ ID NO:4). FIG. 9B: GCN/GCM=lentiviral vector preparations made with a single vector genome plasmid encoding NYESO1 with wild type DIS (GCGCGC, SEQ ID NO:1); GCN/GCM=multigenome lentiviral vector preparation made with two different vector genome plasmids each containing wild type HIV DIS sequence of SEQ ID NO:1: GCN: genome encoding NYESO; GCM: genome encoding MAGEA3; GGN/CCM=multigenome lentiviral vector preparation made with two different vector genomes: GGN: vector genome encoding NYESO1 with mutated DIS sequence GGGGGG, SEQ ID NO:4; GGM: vector genome encoding MAGEA3 with mutated DIS sequence CCCCCC, SEQ ID NO:5.

BRIEF DESCRIPTION OF THE SEQUENCE IDENTIFIERS

Figure 1:
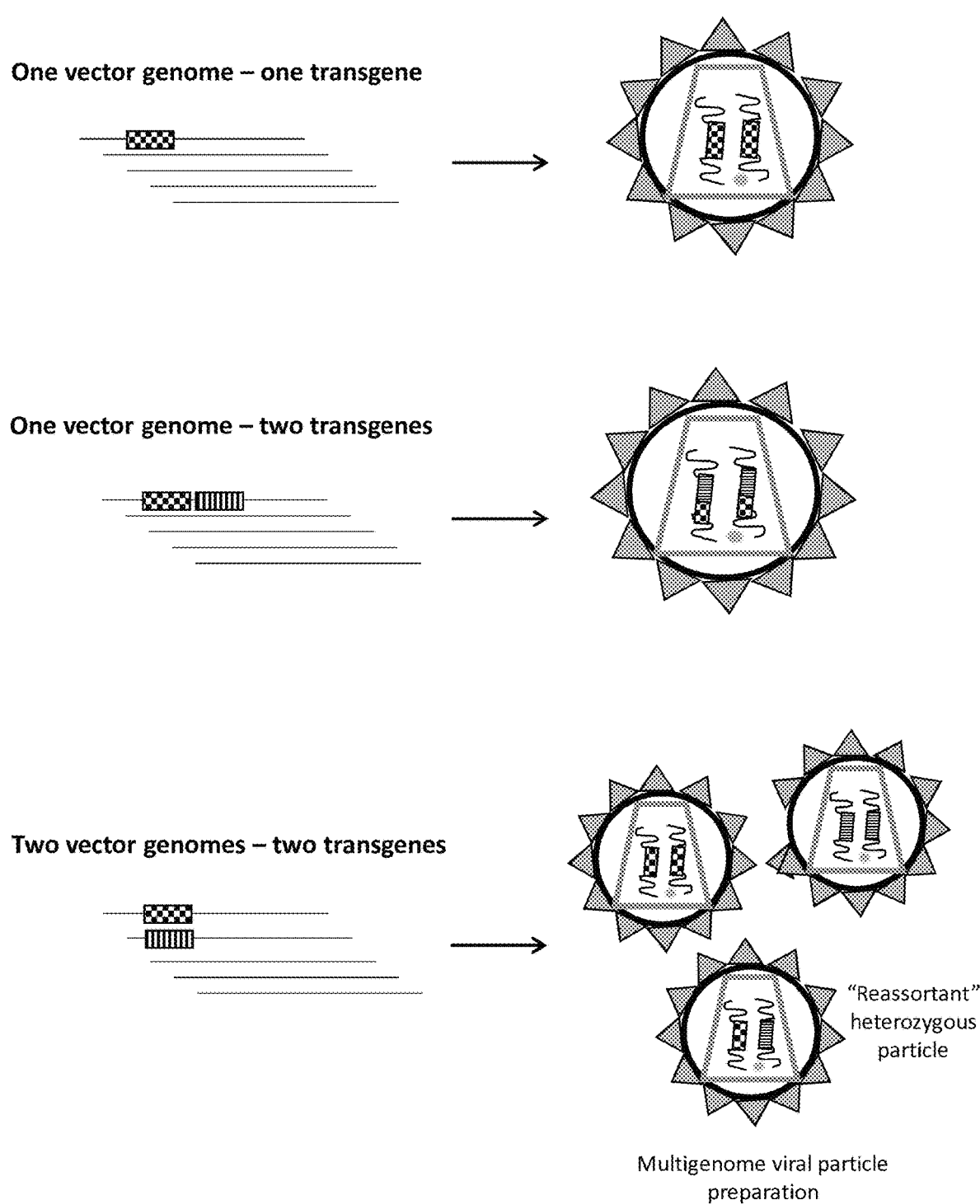
FIG. 1 is a diagram showing how the multigenome retroviral vector preparations are produced. As noted, the heterozygous viral particles produced in the multigenome system can be referred to as reassortants.

SEQ ID NO 1-SEQ ID NO: 14 are dimer initiation site (DIS) sequences that can be used in the retroviral vector genomes and packaging systems described herein. GCGCGC (SEQ ID NO:1); GCCCGG (SEQ ID NO:2); CCGGGC (SEQ ID NO:3); GGGGGG (SEQ ID NO:4); CCCCCC (SEQ ID NO:5); GUGCAC (SEQ ID NO:6); GCGCGG (SEQ ID NO:7); CGCGCC (SEQ ID NO:8); GGGCGG (SEQ ID NO:9); CCCGCC (SEQ ID NO:10); CGCGCG (SEQ ID NO; 11); CGGGCC (SEQ ID NO:12); GGCCCG (SEQ ID NO:13); CACGUG (SEQ ID NO:14).

DETAILED DESCRIPTION

Lentiviral vectors are proven tools for delivering nucleic acid in vivo. U.S. Pat. No. 8,187,872 describes an integration-deficient, DC-targeting modified third generation lentiviral vector platform currently under evaluation in Phase 2 studies for its ability to elicit immune responses against tumor-associated antigen (TAA). For lentiviral vector technologies, the size of the payload is often limited to 8-10 kb, which, although significant, can hinder the targeting of multiple tumor antigens (TAs) and hinder including other sequences of interest such as those encoding immunomodulatory molecules. Additionally, common methods of expressing multiple proteins, such as antigens, within a single vector construct (e.g., endoprotease cleavage, internal ribosome entry sites (IRES), etc) often lead to decreased expression of proteins of interest and/or, in the setting of vaccines, significantly reduced induction of antigen-specific T cell responses against one or more encoded antigens.

Thus, the present multigenome retroviral vector preparations were designed to overcome the limitations of single genome vector platforms with respect to efficient co-expression of any combination of desired genes. Unlike other vectors the present multigenome vector preparations do not require multiple cloning steps modifying the vector backbone, which often result in unpredictable expression patterns of the coded gene products. The present disclosure overcomes the limitations of prior vector systems and successfully allows for multigene delivery in vivo. The present disclosure provides a next generation retroviral vector system that achieves among other things, effective targeting of multiple tumor antigens. The ability to mix antigen-expressing plasmids at controllable ratios at the transfection stage of vector production grants otherwise unachievable flexibility to manufacture combinations of multigenome vectors, and its versatility and agility of manufacturing makes it potentially the best-in-class vector system for co-expression of tumor antigens and immune modulators for enhanced cancer immunotherapy. Because of its ability to generate robust antigen-specific T cell responses across multiple antigens and/or epitopes of interest (including neoantigen epitopes), the present multigenome retroviral vector system is potentially a powerful platform to generate agents with superior anti-tumor control across multiple tumor types. The present disclosure provides other advantages as described herein.

The present disclosure describes generation of retroviral vector particles expressing one (homologous vector) or two (heterologous vector) transgenes in a single production step. This is a novel approach to generating retroviral vector preparations which can deliver and express two or more proteins of interest and overcomes the current limitations of constructing bi- or multicistronic vectors, which include limitations of insert size, compromised gene expression, impaired biosynthesis of functional gene products, lack of effective control of relative expression levels, etc.

The present disclosure describes in one aspect heterozygous retroviral vector particles and methods to generate such vector particles containing two RNA genomes coding each for different transgenes generated through controlled and directed genetic reassortment during the manufacturing process (see FIG. 1). The process produces a mixture of lentiviral vector particles, some of which are heterozygous and some of which are homozygous. As described in more detail herein, the process can be controlled such that the ratio of heterozygous to homozygous particles in the viral vector preparations can be modified as desired. These multigenome viral vector preparations comprising heterozygous particles can be used to deliver and express two or more different nucleic acids of interest in vivo or in vitro in target cells, (e.g., dendritic cells, T cells or other target cells), alone or in combination, e.g. nucleic acids that encode cancer antigens including neoantigens, cytokines, immune checkpoint inhibitors, or any other protein of interest. The invention enables the rapid construction of off-the-shelf, semi-personalized and personalized cancer vaccines with superior immunogenicity and breadth of protection compared to current state-of-the-art approaches in constructing vectored cancer vaccines.

Expression of multiple transgenes from reassortant retroviral vectors can overcome these problems. Whereas cloning of multicistronic vectors require optimization of the positioning of the transgenes of interest in the transfer vector genome, reassortant vectors can be generated much faster by transfecting producer/packaging cells with a mix of plasmids comprising multiple retroviral transfer vector (retroviral genomes) each expressing a different transgene.

Expression of multiple transgenes is sometimes achieved by combining monocistronic vector preparations prior to transducing cells. This requires the combined vector mix to be used at high multiplicities of infection (MOI) for in vitro transductions, which results in inefficient use of the vector preparations. Moreover, this approach is highly ineffective in vaccine or therapeutic settings as achieving co-transduction is unpredictable following administration in vivo. The present invention allows for coexpression of two transgenes in vivo and at very low MOPs in vitro.

The present invention allows for creating personalized cancer vaccines based on vector mixes generated through multi-plasmid transfections using off-the-shelf transfer vectors. This also allows for creating vaccines composed of different transgenes whose mechanism of action benefits from co-expression within the same cell in vivo. One example being co-expression of transgenes encoding helper T-cell epitopes with CTL- or B-cell epitopes for the induction of potent adaptive immune responses and immunological memory. A second example being co-expression of an antigen with an intracellular immunomodulating factor, such as IRF-3, or a CpG motif. A third example being co-expression of individual subunits of a hetero-dimeric functional molecules such as Interleukin-12, in a way that avoids the potential of "non-self" neoantigen epitopes resulting from engineered linker domains. A fourth example being expression of self-replicating, replicon, transcripts that are very large and therefore inefficiently packaged into LV. By splitting up the large replicon RNA into two separate but complementary vector constructs the replicon functionality can be achieved with inserts individually small enough to be packaged.

Furthermore, the present invention allows for effective control of the blending ratio of the individual vector genomes by varying the relative amount of input plasmids during the production step as summarized in Table 1 and Table 2 herein. This cannot be reliably achieved with multicistronic vectors.

Moreover, the present invention provides an additional advantage of being able to control the proportions of heterozygous or homozygous vectors in any given preparation by modifying the dimer initiation signal of each retroviral vector genome to either promote homozygous interactions or heterozygous interactions. In this regard, it is known that the two retrovirus RNA copies meet up in the host cell before viral budding, even before they interact with the gag protein (see e.g., Moore et al., AIDS Rev. 2009 April-June; 11(2): 91-102.). In HIV-1, for example, there is a stem loop in the RNA called SL1 that exposes a palindromic sequence GCGCGC (SEQ ID NO:1). This sequence interacts in a Watson-Crick manner with the same sequence on the other RNA partner. Modifying this sequence can turn dimerization on or off. This feature can be utilized to tailor a given genome to specific desired dimerization properties. Palindromic dimerization sequences derived from any retrovirus are contemplated for use herein. As another example, HIV-1 subtype C has the palindrome GUGCAC (SEQ ID NO:6).

As one example, to reduce the probability of genome A dimerizing with genome B, a different palindromic sequence can be used in genome B (a sequence which does not pair with the palindromic sequence of genome A) allowing it only to dimerize with itself. The sequence can be designed such that it will allow homodimerization but not heterodimerization with genome A. This could be useful in circumstances where a particular sequence of interest benefits from being in homozygous vectors, e.g., for the purpose of generating immune responses.

As another example, the palindromic dimerization sequence can be modified such that homodimerization cannot occur (e.g., the sequence is modified to be non-palindromic). Instead the sequence is engineered to form strong base-pairing with a cognate partner. For example, a sequence such as GCCCGG (SEQ ID NO:2) for genome A and CCGGGC (SEQ ID NO:3) for genome B. This sequence configuration favors heterologous dimer pairing and heterozygous vector particle formation. In this way, the resulting proportion of heterozygous vector particles (reassortants) in a preparation can be controlled and made to contain more than 50% reassortants. This is useful, for example, where an immunomodulatory molecule is delivered along with a particular antigen and is best delivered to the same host cell (e.g., where IRF3, CD40, siRNA or other sequences of interest are used that need to be co-delivered). Another example of where it would be preferable to promote heterozygous pairing is to express TCR-alpha and beta chains with as few homodimers as possible for CART production. Other dimerization motifs that are contemplated herein include GGGGGG (SEQ ID NO:4) and CCCCCC (SEQ ID NO:5) for A and B, respectively. Addition of one or more A-U base pairings could be used to modify the binding strength of the interaction. See also, Baig et al., 2008 Retrovirl 5:65; Lu et al 2011 J Mol Biol 410:609; Moore et al., 2007 J Virol 81:4002; Moore et al., 2009 AIDS Rev. 11:91; Tran et al., 2015 Retrovirol 12:83.

A. Viral Vector Envelope

The viral vectors described herein are generally pseudotyped with an envelope protein from a heterologous virus. A "pseudotyped" lentivirus is a lentiviral particle having one or more envelope glycoproteins that are encoded by a virus that is distinct from the lentiviral genome. The envelope glycoprotein may be modified, mutated or engineered as described herein. Any envelope glycoprotein with suitable targeting and other characteristics as known to the skilled person can be used to pseudotype the viral vectors herein. In certain embodiments, the viral vectors are pseudotyped with VSVg envelope glycoprotein. In other embodiments, the viral vectors may be pseudotyped with an envelope glycoprotein derived from a heterologous HIV (e.g., HIV-2) or other heterologous retrovirus such as feline immunodeficiency virus (FIV), equine infectious anemia virus, Simian Immunodeficiency Virus (SIV) or maedi/visna virus. In yet further embodiments, the viral vectors described herein a pseudotyped with measles virus envelope glycoproteins.

In particular embodiments, the viral vectors described herein are pseudotyped with an envelope glycoprotein derived from an Arbovirus. Arthropod-borne viruses (Arboviruses) are viruses that are transmitted to a host, such as humans, horses, or birds by an infected arthropod vector such as a mosquito. Arboviruses are further divided into sub-families of viruses including alphaviruses and flaviviruses, which have a single-stranded RNA genome of positive polarity and a glycoprotein-containing envelope. For example, dengue fever virus, yellow fever virus and West Nile virus belong to the flavivirus family, and Sindbis virus, Semliki Forest virus and Venezuelan Equine Encephalitis virus, are members of the alphavirus family (Wang et al. J. Virol. 66, 4992 (1992)). The envelope of Sindbis virus includes two transmembrane glycoproteins (Mukhopadhyay et al. Nature Rev. Microbio. 3, 13 (2005)): E1, believed to be responsible for fusion, and E2, believed to be responsible for cell binding. Sindbis virus envelope glycoproteins are known to pseudotype other retroviruses, including oncoretroviruses and lentiviruses.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, "envelope" of an arbovirus virus includes at least E2, and may also include E1, 6K and E3. An exemplary sequence of envelope glycoproteins of Sindbis virus, strain HR, is presented as SEQ ID No. 17 of WO 2011/011584. Sequences of envelope glycoproteins for other arboviruses can be found in e.g., GenBank. For example, sequence encoding Dengue virus glycoproteins can be found in Accession GQ252677 (among others in GenBank) and in the virus variation database at NCBI (GenBank accessions and virus variation database are incorporated by reference for envelope glycoprotein sequences) and sequence encoding Venezuelan equine encephalitis virus envelope glycoproteins in Accession NP 040824 (incorporated by reference for sequences of envelope glycoproteins).

Although the cellular receptor(s) on dendritic cells for alphaviruses, and Sindbis virus in particular, have not been definitively identified to date, one receptor appears to be DC-SIGN (Klimstra et al., J Virol 77: 12022, 2003). The use of the terms "attachment", "binding", "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (Geijtenbeek, T. B., et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that don't express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also appears to bind to cells via heparan sulfate (Klimstra et al., J Virol 72: 7357, 1998; Burmes and Griffin, J Virol 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, non-specific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudo-typed with Sindbis virus envelope E2 glycoprotein may offer other advantages over viral particles pseudo-typed with glycoproteins such as VSVG. Examples of such advantages include reduced complement-mediated lysis and/or reduced neuronal cell targeting, both of which are believed to associate with administration of VSV-G pseudo-typed viral particles.

In various exemplifications, the lentiviral vector particles specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described herein, or other methods known in the art, to identify envelope glycoproteins with the most desirable characteristics.

B. Lentiviral Vector Genome

The viral vector particle comprises a genome, which comprises the sequence(s) of interest. Other sequences may be included, such as sequences that allow the genome to be packaged into the virus particle and sequences that promote expression of the sequence(s) of interest following transduction of the target cell. The genome can be derived from any of a large number of suitable, available retroviral, e.g., lentiviral, genome based vectors, including those identified for human gene therapy applications, such as those described by Pfeifer and Verma (Annu. Rev. Genomics Hum. Genet. 2:177-211, 2001).

1. Backbone

Suitable retroviral vector genomes can be derived from any retrovirus, including alpharetroviruses (Rous sarcoma virus), Betaretroviruses (mouse mammary tumor virus), Gammaretroviruses (Murine leukemia virus; feline leukemia virus), Deltaretroviruses (Bovine leukemia virus; Human T lymphotropic virus (HTLV)), Epsilonretroviruses, Spumaviruses (Simian foamy virus) and lentiviruses. Particularly illustrative retroviral vector genomes include lentiviral vector genomes. Lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells, it is not necessary for target cells to be dividing (or to stimulate the target cells to divide). Generally, the genome and envelope glycoproteins will be based on different viruses, such that the resulting viral vector particle is pseudotyped. Safety features of the vector genome are desirably incorporated. Safety features include self-inactivating LTR and a non-integrating genome.

In some exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (Zufferey et al. J Virol 72: 9873, 1998; Miyoshi et al., J Virol 72:8150, 1998). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

Retroviral vector genomes are generally defective in gag, and/or in pol (see Coffin, J., In: RNA Tumor Viruses, Weiss, R. et al. (ed) Cold Spring Harbor Laboratory, Vol. 2, pp. 36-73, 1985). Thus, the retroviral vector genomes suitable for use herein are generally defective retroviral vector genomes that, once packaged, are capable of infecting a target cell, reverse transcribing their RNA genomes, and in certain embodiments, integrating the reverse transcribed DNA into the target cell genome (or remain as episomal), but are incapable of replicating within the target cell to produce infectious retroviral particles. These so called third and fourth generation retroviral vectors have genomes that are in essence gutted of most or all HIV proteins. Viral proteins necessary for particle production are then provided in trans in the packaging system, offering significant safety advantages. Thus, in certain embodiments, the vector genome comprises a polynucleotide that does not contain a functional gag/pol open reading frame. Thus, in certain embodiments, suitable vector genomes do not encode for a functional gag or pol protein. In certain embodiments, suitable vector genomes do not encode for a functional gag, pol or env protein. As would be understood by the ordinarily skilled person, in certain embodiments, it may be desireable to keep some gag sequence that is near the packaging signal in order to facilitate cloning and/or efficient packaging however the full coding region for gag/pol is not present.

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

As stated above, one approach is to make and use a non-functional integrase. Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC), the central domain core, which contains the catalytic core and a conserved DD35E motif (D64, D116, E152 in HIV-1), and a C-terminal domain, which has DNA binding properties. Point mutations introduced into integrase are sufficient to disrupt normal function. Many integrase mutations have been constructed and characterized (see, Philpott and Thrasher, Human Gene Therapy 18:483, 2007; Apolonia, Thesis submitted to University College London, April 2009, pp, 82-97; Engelman et al. J Virol 69: 2729, 1995; Nightingale et al. Mol Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (Engelman et al. J Virol 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g. W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (Brown et al J Virol 73:9011 (1999). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of the 3' polypurine tract (PPT) (WO 2009/076524), located proximally to the 3' LTR. The PPT is a polypurine sequence of about 15 nucleotides that can serve as a primer binding site for plus-strand DNA synthesis. In this case, mutations or deletions of PPT targets the reverse transcription process. Without wishing to be held to a mechanism, by mutating or deleting PPT, production of linear DNA is radically reduced and essentially only 1-LTR DNA circles are produced. Integration requires a linear double-stranded DNA vector genome, and integration is essentially eliminated without it. As stated above, a PPT can be made non-functional by mutation or by deletion. Typically, the entire about 15 nt PPT is deleted, although in some embodiments, shorter deletions of 14 nt, 13 nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (McWilliams et al., J Virol 77:11150, 2003), although single and double mutations in the first four bases still reduce transcription. Mutations made at the 3' end of PPT generally have a more dramatic effect (Powell and Levin J Virol 70:5288, 1996).

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

2. Regulatory Elements

As discussed herein, the viral vector genome comprises one or more nucleic acids of interest that is desirable to express in target cells. For simplicity, the term "sequence of interest" (SOI) is used to mean one or more sequences of interest (such as an antigen, with or without one or more other immunostimulatory molecules, cytokines or one or more additional antigens). Typically, the sequences of interest are located between the 5' LTR and 3' LTR sequences. Further, the sequence of interest is preferably in a functional relationship with other genetic elements, for example transcription regulatory sequences including promoters or enhancers, to regulate expression of the sequence of interest in a particular manner. In certain instances, the useful transcriptional regulatory sequences are those that are highly regulated with respect to activity, both temporally and spatially. Expression control elements that may be used for regulating the expression of the components are known in the art and include, but are not limited to, inducible promoters, constitutive promoters, secretion signals, enhancers and other regulatory elements.

The sequence of interest and any other expressible sequence is typically in a functional relationship with internal promoter/enhancer regulatory sequences. An "internal" promoter/enhancer is one that is located between the 5' LTR and the 3' LTR sequences in the viral vector construct and is operably linked to the sequence of interest. The internal promoter/enhancer may be any promoter, enhancer or promoter/enhancer combination known to increase expression of a gene with which it is in a functional relationship. A "functional relationship" and "operably linked" mean, without limitation, that the sequence is in the correct location and orientation with respect to the promoter and/or enhancer that the sequence of interest will be expressed when the promoter and/or enhancer is contacted with the appropriate molecules.

The choice of an internal promoter/enhancer is based on the desired expression pattern of the sequence of interest and the specific properties of known promoters/enhancers. Thus, the internal promoter may be constitutively active. Non-limiting examples of constitutive promoters that may be used include the promoter for ubiquitin (U.S. Pat. No. 5,510,474; WO 98/32869,), CMV (Thomsen et al., PNAS 81:659, 1984; U.S. Pat. No. 5,168,062,), beta-actin (Gunning et al. 1989 Proc. Natl. Acad. Sci. USA 84:4831-4835,) and pgk (see, for example, Adra et al. 1987 Gene 60:65-74; Singer-Sam et al. 1984 Gene 32:409-417; and Dobson et al. 1982 Nucleic Acids Res. 10:2635-2637,).

Alternatively, the promoter may be a tissue specific promoter. In some preferred embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC Class II. In addition, promoters may be selected to allow for inducible expression of the sequence of interest. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of the gene of interest. The artisan of ordinary skill will be able to select a promoter based on the desired expression pattern of the gene in the organism or the target cell of interest.

The viral genome may comprise at least one RNA Polymerase II or III responsive promoter. This promoter can be operably linked to the sequence of interest and can also be linked to a termination sequence. In addition, more than one RNA Polymerase II or III promoters may be incorporated. RNA polymerase II and III promoters are well known to one of skill in the art. A suitable range of RNA polymerase III promoters can be found, for example, in Paule and White, Nucleic Acids Research., Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods of the invention. Particularly suited Pol II or III promoters include the tetracycline responsive promoters provided in Ohkawa and Taira, Human Gene Therapy, Vol. 11, pp 577-585 (2000) and in Meissner et al. Nucleic Acids Research, Vol. 29, pp 1672-1682 (2001).

An internal enhancer may also be present in the viral construct to increase expression of the gene of interest. For example, the CMV enhancer (Boshart et al. Cell, 41:521, 1985;) may be used. Many enhancers in viral genomes, such as HIV, CMV, and in mammalian genomes have been identified and characterized (see GenBank). An enhancer can be used in combination with a heterologous promoter. One of ordinary skill in the art will be able to select the appropriate enhancer based on the desired expression pattern.

A viral vector genome will usually contain a promoter that is recognized by the target cell and that is operably linked to the sequence of interest, viral components, and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operably linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in "Promoters used to regulate gene expression" on Patent Lens web site, accessed 18 May 2009.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. Heterologous promoters are preferred, however, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The viral vector genome may also contain additional genetic elements. The types of elements that may be included in the construct are not limited in any way and may be chosen to achieve a particular result. For example, a signal that facilitates nuclear entry of the viral genome in the target cell may be included. An example of such a signal is the HIV-1 cPPT/CTS signal (DNA flap). Further, elements may be included that facilitate the characterization of the provirus integration site in the target cell. For example, a tRNA amber suppressor sequence may be included in the construct. An insulator sequence from e.g., chicken β-globin may also be included in the viral genome construct. This element reduces the chance of silencing an integrated provirus in the target cell due to methylation and heterochromatinization effects. In addition, the insulator may shield the internal enhancer, promoter and exogenous gene from positive or negative positional effects from surrounding DNA at the integration site on the chromosome. In addition, the vector genome may contain one or more genetic elements designed to enhance expression of the gene of interest. For example, a woodchuck hepatitis virus responsive element (WRE) may be placed into the construct (Zufferey et al. 1999. J. Virol. 74:3668-3681; Deglon et al. 2000. Hum. Gene Ther. 11:179-190,).

The viral vector genome is typically constructed in a plasmid form that may be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

Plasmids containing one or more of the components described herein are readily constructed using standard techniques well known in the art. For analysis to confirm correct sequences in plasmids constructed, the plasmid may be replicated in *E. coli*, purified, and analyzed by restriction endonuclease digestion or its DNA sequence determined by conventional methods.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22. Other vectors and methods suitable for adaptation to the expression of polypeptides are well known in the art and are readily adapted to the specific circumstances.

Using the teachings provided herein, one of skill in the art will recognize that the efficacy of a particular expression system can be tested by transfecting packaging cells with a vector comprising a gene encoding a reporter protein and measuring the expression using a suitable technique, for example, measuring fluorescence from a green fluorescent protein conjugate. Suitable reporter genes are well known in the art.

3. Dimer Initiation Site (DIS) Sequences

Retroviruses selectively package two copies of the unspliced RNA genome. It is known that the two retrovirus RNA copies meet up in the host cell before viral budding, even before they interact with the gag protein (see e.g., Moore et al., AIDS Rev. 2009 April-June; 11(2): 91-102; Lu et al J Mol Biol 2011 410:609-633). In HIV-1, for example, there is a stem loop in the RNA located near the 5'-end of the genome and primarily within the 5'untranslated region (5'UTR) called SL1 that exposes a palindromic sequence GCGCGC (SEQ ID NO:1). This sequence interacts in a Watson-Crick manner with the same sequence on the other RNA partner. Modifying this sequence can turn dimerization on or off. This feature can be exploited to tailor a given genome to specific desired dimerization properties. Palindromic or non-palindromic dimer initiation site (DIS) sequences derived from any retrovirus are contemplated for use herein. Synthetic palindromic or non-palindromic DIS sequences are also contemplated for use herein. As another example, HIV-1 subtype C has the palindrome GUGCAC (SEQ ID NO:6).

As one example, to reduce the probability of genome A dimerizing with genome B, a different palindromic sequence can be used in genome B (a sequence which does not pair with the palindromic sequence of genome A) allowing it only to dimerize with itself. The sequence can be designed such that it will allow homodimerization but not heterodimerization with genome A. This could be useful in circumstances where a particular sequence of interest benefits from being in homozygous vectors, e.g., for the purpose of generating immune responses.

As another example, the palindromic DIS sequence can be modified such that homodimerization is reduced (e.g., the sequence is modified to be non-palindromic). Instead the sequence is engineered to form strong base-pairing with a cognate partner. For example, a sequence such as GCCCGG (SEQ ID NO:2) for genome A and CCGGGC (SEQ ID NO:3) for genome B. This sequence configuration favors heterologous dimer pairing and heterozygous vector particle formation. In this way, the resulting proportion of heterozygous vector particles (reassortants) in a preparation can be modified and made to contain more than 50% reassortant heterozygous particles. This is useful, for example, where an immunomodulatory molecule is delivered along with a particular antigen and is best delivered to the same host cell (e.g., where IRF3, CD40, siRNA or other sequences of interest are used that need to be co-delivered). Another example of where it would be preferable to promote heterozygous pairing is to express TCR-alpha and beta chains with as few homodimers as possible for CART production. Other dimerization motifs that are contemplated herein include GGGGGG (SEQ ID NO:4) and CCCCCC (SEQ ID NO:5) for A and B, respectively. Addition of one or more A-U base pairings could be used to modify the binding strength of the interaction. Further dimerization sequence pairs that can be used in the vectors herein include GCGCGG (SEQ ID NO:7) paired with CGCGCC (SEQ ID NO:8); GGGCGG (SEQ ID NO:9) paired with CCCGCC (SEQ ID NO:10). See also, Lu et al 2011 J Mol Biol 410:609; Baig et al., 2008 Retrovirl 5:65; Moore et al., 2007 J Virol 81:4002; Moore et al., 2009 AIDS Rev. 11:91; Tran et al., 2015 Retrovirol 12:83. Any RNA sequence or sequence pair that functions to promote a desired pairing of one genome with another or serves as a dimerization sequence is contemplated for use with the viral vectors and packaging systems herein.

4. Sequences of Interest (SOI)

The sequence of interest is not limited in any way and includes any nucleic acid that one of ordinary skill desires to have transcribed, and express in the target cell. Typically, the sequence of interest is heterologous to the retroviral vector genome however in certain embodiments the sequence of interest may encode a retroviral protein. The product can be a protein or a nucleic acid. The sequence of interest can encode a protein or a nucleic acid molecule, including siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein.

In some instances, the sequence of interest can encode an antigen against which an immune response is desired. In particular, tumor antigens, in particular neoantigens, and infectious disease antigens from agents such as HIV, RSV, HBV, HSV, HCV, HPV, pertussis, *Staphylococcus aureus*, malaria, or tuberculosis are desirable. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor-associated antigen or neoantigen, or may be identified from the tumor itself by any of a variety of methods known in the art.

Tumor-associated antigens are known for a variety of cancers including, for example, sarcomas, renal cell carcinoma, prostate cancer, melanoma, and breast cancer. In some breast cancers, for example, the Her-2 receptor is overexpressed on the surface of cancerous cells. Exemplary tumor antigens include tissue differentiation antigens, mutant protein antigens, oncogenic viral antigens, cancer-testis antigens and vascular or stromal specific antigens. Tumor antigens contemplated for use herein include, but are not limited to, any cancer testis antigen, any one or more of the MAGE tumor antigens (e.g., MAGEA1, MAGEA2, MAGEA3, MAGEA4, MAGEA10), BAGE, RAGE, and NY-ESO-1, which are unmutated antigens expressed in the immune-privileged areas of the testes and in a variety of tumor cells; lineage-specific tumor antigens such as the melanocyte-melanoma lineage antigens MART-1/Melan-A, gp100, gp75, mda-7, tyrosinase and tyrosinase-related protein, renal cell carcinoma-5T4, SM22-alpha, carbonic anhydrases I and IX (also known as G250), hypoxia-inducible factors (e.g., HIF-1alpha and HIF-2alpha), VEGF or prostate specific membrane antigen (PSMA), prostate-specific antigen (PSA), prostatic acid phosphates, and six-transmembrane epithelial antigen of the prostate (STEAP), NKX3.1, which are antigens expressed in normal and neoplastic cells derived from the same tissue; epitope proteins/peptides derived from genes mutated in tumor cells or genes transcribed at different levels in tumor compared to normal cells, such as telomerase enzyme, survivin, mesothelin, SSX2 (HOM-MEL-40 tumor antigen), mutated ras, bcr/abl rearrangement, Her2/neu, EGF receptor (including EGFRviii mutation), mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; epitope proteins/peptides derived from oncoviral processes, such as human papilloma virus proteins E6 and E7; nonmutated oncofetal proteins with a tumor-selective expression, such as carcinoembryonic antigen and alpha-fetoprotein. Also contemplated as a tumor associated antigen is the embryonic transcription factor Brachyury (see e.g., Roselli et al., Clin Cancer Res. 2012 Jul. 15; 18(14):3868-79; Hamilton et al., Semin Oncol. 2012 June; 39(3):358-66; Palena et al., J Natl Cancer Inst. 2014 May 9; 106(5)). A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001.).

In one particular embodiment, the multigenome lentiviral vector preparation expresses NYESO1 and MAGEA3 as sequences of interest. In a further embodiment, the multigenome lentiviral vector preparation expresses multiple MAGE proteins, with or without an immunomodulatory molecule. In one embodiments, the multigenome lentiviral vector preparation expresses MAGEA1, MAGEA3, MAGEA4, MAGEA10 and IL-12. In an additional embodiment, the multigenome lentiviral vector preparation expresses multiple MAGE proteins in addition to one or more neoantigens, with or without an immunomodulatory molecule. In this regard, the one or more neoantigens may be from a MAGE antigen or from a different protein.

In certain embodiments, the sequence of interest encodes one or more neoantigens. Neoantigens are abnormal mutated proteins that are produced by cancer cells and are recognized by the immune system (see e.g., Martin et al 2015 Annals Oncol. 26:2367-2374; Linnemann et al., 2015 Nature Medicine 21:81-85; Kreiter et al., Nature 520, 692-696; Blood. 2014 Jul. 17; 124(3): 453-462;' and others). Neoantigens can be identified by sequencing DNA and RNA from tumor and normal tissues from an individual to identify tumor-specific mutations; HLA typing the individual and predicting HLA binding epitopes from the neoantigens identified. The neoantigens are then synthesized in open reading frames and used in the preparation of personalized vaccines. High throughput sequencing and epitope identification using in silico prediction and/or MS based sequencing of HLA-eluted peptides from tumor biopsies, and immunoassay confirmation allows for identification of neoantigens from patients and immediate use of the identified neoantigens in personalized vaccines. Thus, the present systems for producing multigenome vector preparations are particularly suited for producing patient-specific multigenome viral vector preparations encoding neoantigens or neoantigen polyepitope cassettes and optionally with other full length tumor antigens and/or immunomodulatory molecules.

The antigen can also be an antigen associated with an infectious disease, such as, for example, HIV/AIDS. The antigen can be, for example, gp120 (Klimstra, W. B., et al. 2003. J Virol 77:12022-12032; Bernard, K. A., et al. 2000. Virology 276:93-103; Byrnes, A. P., et al. 1998. J Virol 72: 7349-7356). Other exemplary antigens include, but are not limited to: gag, pol, env, tat, nef and rev (Lieberman, J. et al. 1997. AIDS Res Hum Retroviruses 13(5): 383-392; Menendez-Arias, L. et al. 1998. Viral Immunol 11(4): 167-181).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, or a hepatitis C virus E1 or E2 glycoproteins, core, or non-structural proteins, herpes-virus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi*

OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and selected, a sequence that encodes the desired antigen is identified. In certain embodiments, the sequence comprises a cDNA.

In certain cases, the sequence of interest can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are well known in the art (Fire et al., Nature 391:806, 1998; see also "The RNA Interference Resource" of Applied Biosystems, Trang et al., Oncogene Suppl 2:S52, 2008; Taganov, K., et al. 2007. Immunity 26:133-137; Dahlberg, J. E. and E. Lund. 2007. Sci. STKE 387:pe25; Tiemann and Rossi, EMBO Mol Med 1: 142, 2009). Alternatively, the sequence of interest can encode a self-complementary double stranded RNA in which the complementary region is greater than about 20 ribonucleotides in length, or an anti-sense RNA that is greater than about 20 ribonucleotides in length. Those of ordinary skill in the art will appreciate that siRNA, miRNA, dsRNA and anti-sense RNA molecules can be expressed from an RNA polymerase III promoter, or, alternatively, can be a component of a non-coding RNA that is transcribed from an RNA polymerase II promoter.

In addition, the sequence of interest may encode more than one product. In some configurations, the sequence to be delivered can comprise multiple genes encoding at least one protein, at least one siRNA, at least one microRNA, at least one dsRNA or at least one anti-sense RNA molecule or any combinations thereof. For example, the sequence to be delivered can include one or more nucleic acids that encode one or more antigens against which an immune response is desired. The one or more antigens can be associated with a single disease or disorder, or they can be associated with multiple diseases and/or disorders. In certain embodiments, the SOI comprises a sequence encoding an immunomodulatory protein. In some instances, a sequence encoding an immunomodulatory protein can be included along with a sequence encoding an antigen against which an immune response is desired, and the combination can elicit and regulate the immune response to the desired direction and magnitude. In other instances, a sequence encoding an siRNA, microRNA, dsRNA or anti-sense RNA molecule can be constructed with a gene encoding an antigen against which an immune response is desired, and the combination can regulate the scope of the immune response. The products may be produced as an initial fusion product in which the encoding sequence is in functional relationship with one promoter. Alternatively, the products may be separately encoded and each encoding sequence in functional relationship with a promoter. The promoters may be the same or different.

In certain configurations, vectors contain polynucleotide sequences that encode immunomodulatory molecules. Exemplary immunomodulatory molecules include any of a variety of cytokines. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, IL-1, IL-1alpha, IL-2, IL-3, IL-4, IL-5, IL-6, IL-7, IL-8, IL-9, IL-10, IL-11, IL-12; IL-15, IL-18, IL-21, IL-23, IL-27, TNF; and other polypeptide factors including LIF and kit ligand (KL). Other immunomodulatory molecules contemplated for use herein include IRF3, B7.1, B7.2, 4-1BB, CD40 ligand (CD40L), drug-inducible CD40 (iCD40), and the like. In certain embodiments, these polynucleotides are typically under the control of one or more regulatory elements that direct the expression of the coding sequences in dendritic cells.

In certain embodiments, the immunomodulatory molecule encoded by the retroviral vectors described herein is a checkpoint inhibitor molecule. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides vectors encoding immune checkpoint inhibitors. Immune checkpoint inhibitors include any agent that blocks or inhibits in a statistically significant manner, the inhibitory pathways of the immune system. Such inhibitors may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+(αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

In certain embodiments, the sequence of interest expressed by the lentiviral vector genome is a chimeric antigen receptor (CAR) (also referred to as a chimeric T cell receptor) or a recombinant T cell receptor, including single chain or soluble T cell receptors. In certain embodiments, activation and co-stimulation of target T cells are provided by a single chimeric T cell receptor comprising a cytoplasmic signaling domain (e.g., zeta chain signaling domain with or without a costimulatory signaling region) and a target-specific antigen binding domain. The chimeric antigen receptors herein also comprise a transmembrane (TM) domain to anchor them to the surface of the T cell. The TM can be derived from the CD3 zeta chain or can be derived from another transmembrane molecule, such as CD28 or CD4. As would be recognized by the skilled person, any TM domain that functions properly to anchor the chimeric receptor to the membrane can be used. The chimeric T cell receptor is suitably generated in T lymphocytes that have been transduced with the lentiviral vector particles described herein expressing the chimeric T cell receptor. Illustrative chimeric antigen receptors are described, for example, in U.S. Pat. Nos. 7,741,465; 5,843,728; 7,446,190; 6,392,013; 7,994,298; 8,252,914; 6,410,319; 7,446,179; 7,265,209; and published applications US20130288368, WO 2012/079000 and WO2012/129514.

In another embodiment, the sequence of interest encodes a "binding domain" or "binding region" or "binding element". According to the present disclosure, binding domains may be, for example, any protein, polypeptide, oligopeptide, or peptide that possesses the ability to specifically recognize and bind to a biological molecule (e.g., a cell surface receptor or tumor associated protein, or a component thereof). A binding domain includes any naturally occurring, synthetic, semi-synthetic, or recombinantly produced binding partner for a biological molecule of interest. For example, a binding domain may be antibody light chain and heavy chain variable regions, or the light and heavy chain variable region regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE™ analysis).

In certain embodiments, the target molecule to be bound by a binding domain may be a cell surface expressed protein, such as a receptor (e.g., immune checkpoint molecule) or a tumor antigen. In another embodiment, the target molecule bound by a binding domain useful herein is a soluble antigen such as a cytokine, albumin, or other serum protein. Illustrative binding domains include immunoglobulin antigen-binding domains such as scFv, scTCR, extracellular domains of receptors, ligands for cell surface molecules/receptors, or receptor binding domains thereof, and tumor binding proteins. In certain embodiments, the antigen binding domains can be an scFv, a VH, a VL, a domain antibody variant (dAb), a camelid antibody (VHH), a fibronectin 3 domain variant, an ankyrin repeat variant and other antigen-specific binding domain derived from other protein scaffolds.

A sequence encoding a detectable product, usually a protein, can be included to allow for identification of cells that are expressing the desired product. For example, a fluorescent marker protein, such as green fluorescent protein (GFP), is incorporated into the construct along with a sequence of interest (e.g., encoding an antigen). In other cases, the protein may be detectable by an antibody or the protein may be an enzyme that acts on a substrate to yield a detectable product, or a product that allows selection of a transfected or transduced target cell, for example confers drug resistance, such as hygromycin resistance. Typical selection genes encode proteins that confer resistance to antibiotics or other toxins suitable for use in eukaryotic cells, e.g., neomycin, methotrexate, blasticidine, among others known in the art, or complement auxotrophic deficiencies, or supply critical nutrients withheld from the media. The selectable marker can optionally be present on a separate plasmid and introduced by co-transfection.

As described elsewhere, the methods herein for generating reassortant retroviral vectors are intended to overcome certain limitations of multicistronic expression units in vectors. However, in certain embodiments, it may be desirable to use one or more multicistronic expression units that include two or more of the elements (e.g., sequence(s) of interest, the envelope) necessary for production of the desired virus in packaging cells. In certain embodiments, a multicistronic expression unit may be included in the viral vector genome. The use of multicistronic vectors reduces the total number of nucleic acid molecules required and thus avoids the possible difficulties associated with coordinating expression from multiple vector genomes. In a multicistronic vector the various elements to be expressed are operably linked to one or more promoters (and other expression control elements as necessary). In some configurations, a multicistronic vector comprises a sequence of interest, a sequence encoding a reporter product, and viral elements. The sequence of interest typically encodes an antigen, an immunomodulatory molecule, or a combination of one or more antigens and one or more immunomodulatory molecules. At times, the multicistronic vector comprises a gene encoding an antigen, a gene encoding an immunomodulatory molecule.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (U.S. Pat. No. 4,937,190; de Felipe et al. 2004. Traffic 5: 616-626). In one embodiment, oligonucleotides encoding furin cleavage site sequences (RAKR) (Fang et al. 2005. Nat. Biotech 23: 584-590) linked with 2A-like sequences from foot-and-mouth diseases virus (FMDV), equine rhinitis A virus (ERAV), and thosea asigna virus (TaV) (Szymczak et al. 2004. Nat. Biotechnol. 22: 589-594) are used to separate genetic elements in a multicistronic vector. The efficacy of a particular multicistronic vector can readily be tested by detecting expression of each of the genes using standard protocols.

In a specific exemplification, the viral vector genome comprises: a cytomegalovirus (CMV) enhancer/promoter sequence; the R and U5 sequences from the HIV 5' LTR; a packaging sequence (ψ); an RRE, the HIV-1 cPPT/CTS (DNA flap) signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR. (Iwakuma et al. Virology 15:120, 1999,).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000).

Any of the sequences of interest described herein may comprise a variant of the wild type version of the sequence of interest, either of the nucleotide sequence or the amino acid sequence, or both.

With respect to polynucleotide sequences (e.g., DNA/cDNA plasmids used in the packaging systems, RNA genome sequences, etc), polynucleotide variants may contain one or more substitutions, additions, deletions and/or insertions, such that the biological function of the polypeptide encoded by the variant polynucleotide is not substantially diminished relative to the reference polypeptide encoded by the polynucleotide sequence. For example, certain multigenome lentiviral vector preparations may include a sequence encoding an immunomodulatory molecule. A variant of a polynucleotide sequence encoding an immunomodulatory molecule may comprise one or more substitutions, additions, deletions and/or insertions, preferably such that the immunomodulatory activity of the molecule encoded thereby is not substantially diminished relative to the reference immunomodulatory molecule encoded by the polynucleotide sequence. In this regard, such polynucleotides encode polypeptides that have a level of biological activity (e.g., immunomodulatory activity) of at least about 50%, 55%, 60%, 65%, 70%, 75%, 80%, 85%, 90%, 95%, 96%, 97%, 98%, or 99% of that for a reference polypeptide sequence. As a non-limiting example, the immunomodulatory protein may be IL-12. IL-12 activity may be measured using assays known to the person of ordinary skill in the art. The activity of a variant IL-12 polypeptide can be measured and compared to a wild-type IL-12 protein.

In certain embodiments, the variants may be a codon optimized variant polynucleotide sequence that encodes a protein identical to a reference protein.

In another embodiment, a variant may be a heteroclitic analog of a reference sequence (see e.g., U.S. Pat. No. 8,741,576). Heteroclitic epitopes are modified T cell epitopes that induce T cell responses stronger than those induced by the native epitope. Heteroclitic analogs are defined as peptides (or epitopes within the full length protein) having increased stimulatory capacity or potency for a specific T cell, as measured by increased responses to a given dose, or by a requirement of lesser amounts to achieve the same response.

The advantages associated with using heteroclitic analogs in clinical applications are as follows. First, heteroclitic analogs have the ability to break/overcome tolerance by reversing a state of T cell anergy, activating non-tolerized cross-reactive clones of T cells, or by mediating "immune deviation," i.e., the type of CTL produced, such as Th1 or Th2. Recent studies indicate that heteroclitic analogs are immunogenic (Zaremba, et al., Cancer Research, 57:4570 (1997); Rivoltoni, et al., Cancer Research, 59:301 (1999); Selby, et al., 162(2):669 (1999)) in that they are capable of inducing CTLs that recognize endogenously processed epitope. This is confirmed by studies in different immunological systems (Zugel, et al., J. Immunol., 161:1705 (1998), Wang, et al., J. Exp. Med., 190:983 (1999), Men, et al., J. Immunol., 162:3566, (1999)). For example, studies by Zugel et al. (Zugel, et al., supra) have shown that T cell tolerance to an immunodominant T cell epitope in adult mice can be overcome by immunization with heteroclitic cross-reactive peptide analogs of that peptide.

In certain embodiments, the variants are immunogenic variants wherein the polynucleotide variants will contain one or more substitutions, additions, deletions and/or insertions, preferably such that the immunogenicity of the polypeptide encoded by the variant polynucleotide is not substantially diminished relative to a polypeptide encoded by a reference sequence.

In certain embodiments, the polynucleotides herein, e.g., polynucleotide variants, encode polypeptides that are immunologically cross-reactive with a reference polypeptide sequence (e.g., tumor antigen sequences available in public sequence databases). In other embodiments, such polynucleotides encode polypeptides that have a level of immunogenic activity of at least about 50%, 55%, 60%, 65%, 70%, 75%, 80%, 85%, 90%, 95%, 96%, 97%, 98%, or 99% of that for a reference polypeptide sequence.

Therefore, in certain embodiments of the disclosure, a mutagenesis approach, such as site-specific mutagenesis, is employed for the preparation of variants and/or derivatives of the sequences of interest described herein. By this approach, specific modifications in a polypeptide sequence can be made through mutagenesis of the underlying polynucleotides that encode them. This technique provides a straightforward approach to prepare and test sequence variants, for example, incorporating one or more of the foregoing considerations, by introducing one or more nucleotide sequence changes into the polynucleotide.

Site-specific mutagenesis allows the production of variants through the use of specific oligonucleotide sequences which encode the DNA sequence of the desired variant, as well as a sufficient number of adjacent nucleotides, to provide a primer sequence of sufficient size and sequence complexity to form a stable duplex on both sides of the sequence being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of sequences of interest to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule.

C. Production of Multigenome Viral Vector Preparations

Generally, the methods used for producing the retroviral vector particles described herein are standard methods known in the art except that in order to produce multigenome viral vector preparations comprising heterozygous (reassortant) retroviral particles, the packaging system will include at least two different viral vector genome plasmids (see e.g., FIG. 1). Because of the propensity of retroviruses to form genomic reassortants, the resulting vector preparations hypothetically contain a mix of all possible homozygous and heterozygous vector particles.

As noted elsewhere herein, in certain embodiments, the at least two different viral vector genome plasmids contemplated for use herein contain retroviral genomes that are defective. In other words, the retroviral (e.g., lentiviral) vector genomes do not contain a functional gag/pol open reading frame. Thus, in certain embodiments, suitable vector genomes do not encode for a functional gag protein or a function gag or pol protein. In certain embodiments, suitable vector genomes do not encode for a functional gag, pol or env protein.

The present invention allows for effective control of the final ratio of homozygous versus heterozygous vector genomes in the multigenome viral vector particle preparation by varying the relative amount of input plasmids during the production step. The total output genomes distribution likewise can be controlled by varying the relative amount of input plasmids during the production step. These concepts are summarized in Table 1, Table 2, and Table 3 below. As noted elsewhere, the final control over expression of two (or more) different sequences of interest cannot be reliably achieved with multi-cistronic vectors, in particular in an off the shelf manner.

TABLE 1

CONTROL OF BLENDING RATIOS OF RETROVIRAL VECTORS

| RELATIVE RATIO, INPUT PLASMID A AND B* | APPROXIMATE THEORETICAL BLENDING PROPORTIONS | | |
|---|---|---|---|
| | VECTOR PARTICLES HOMOZYGOUS FOR A (A × A) | VECTOR PARTICLES HOMOZYGOUS FOR B (B × B) | VECTOR PARTICLES HETEROZYGOUS FOR A AND B (A × B) |
| 50:50 | 25% | 25% | 50% |
| 60:40 | 36% | 16% | 48% |
| 67:33 | 44.5% | 11% | 44.5% |
| 70:30 | 49% | 9% | 42% |
| 80:20 | 64% | 4% | 32% |
| 90:10 | 81% | 1% | 18% |

*also ≈ output vector genomes

TABLE 2

CONTROL OF BLENDING RATIOS OF RETROVIRAL VECTORS COMPRISING 3 GENOMES

| Input plasmid (%) | | | Vector combinations (%) | | | | | | | Theoretical Genome Distribution | | |
|---|---|---|---|---|---|---|---|---|---|---|---|---|
| A | B | C | AA | BB | CC | AB | AC | BC | Sum | Tot A | Tot B | Tot C |
| 33.3 | 33.3 | 33.3 | 11.1 | 11.1 | 11.1 | 22.2 | 22.2 | 22.2 | 100 | 55.6 | 55.6 | 55.6 |
| 50 | 25 | 25 | 25.0 | 6.3 | 6.3 | 25.0 | 25.0 | 12.5 | 100 | 75.0 | 43.8 | 43.8 |
| 80 | 10 | 10 | 64.0 | 1.0 | 1.0 | 16.0 | 16.0 | 2.0 | 100 | 96.0 | 19.0 | 19.0 |
| 20 | 40 | 40 | 4.0 | 16.0 | 16.0 | 16.0 | 16.0 | 32.0 | 100 | 36.0 | 64.0 | 64.0 |
| 10 | 45 | 45 | 1.0 | 20.3 | 20.3 | 9.0 | 9.0 | 40.5 | 100 | 19.0 | 69.8 | 69.8 |

TABLE 3

| | Input Plasmid Distribution (=output vector genomes*) | | | | | Theoretical % vector particle with at least one genome** | | | | | Theoretical Genetic Makeup of Vector Particles and % Distribution Within Multigenome Viral Preparation | | | |
|---|---|---|---|---|---|---|---|---|---|---|---|---|---|---|
| Input Ratios | IL12 | M1 | M3 | M4 | M10 | IL12 | M1 | M3 | M4 | M10 | IL12:IL12 | IL12:M1 | IL12:M3 | IL12:M4 |
| 1:1:1:1:1 | 20.00% | 20.00% | 20.00% | 20.00% | 20.00% | 36% | 36% | 36% | 36% | 36% | 4.00% | 8.00% | 8.00% | 8.00% |
| 4:1:1:1:1 | 50.00% | 12.50% | 12.50% | 12.50% | 12.50% | 75% | 23% | 23% | 23% | 23% | 25.00% | 12.50% | 12.50% | 12.50% |
| 2:1:1:1:1 | 33.33% | 16.67% | 16.67% | 16.67% | 16.67% | 56% | 31% | 31% | 31% | 31% | 11.11% | 11.11% | 11.11% | 11.11% |
| 3:1:1:1:1 | 28.57% | 14.29% | 14.29% | 14.29% | 14.29% | 41% | 22% | 22% | 22% | 22% | 8.16% | 8.16% | 8.16% | 8.16% |

| | Theoretical Genetic Makeup of Vector Particles and % Distribution Within Multigenome Viral Preparation | | | | | | | | | |
|---|---|---|---|---|---|---|---|---|---|---|
| Input Ratios | IL12:M10 | M1:M1 | M1:M3 | M1:M4 | M1:M10 | M3:M3 | M3:M4 | M3:M10 | M4:M4 | M4:M10 | M10:M10 |
| 1:1:1:1:1 | 8.00% | 4.00% | 8.00% | 8.00% | 8.00% | 4.00% | 8.00% | 8.00% | 4.00% | 8.00% | 4.00% |
| 4:1:1:1:1 | 12.50% | 1.56% | 3.13% | 3.13% | 3.13% | 1.56% | 3.13% | 3.13% | 1.56% | 3.13% | 1.56% |
| 2:1:1:1:1 | 11.11% | 2.78% | 5.56% | 5.56% | 5.56% | 2.78% | 5.56% | 5.56% | 2.78% | 5.56% | 2.78% |
| 3:1:1:1:1 | 8.16% | 2.04% | 4.08% | 4.08% | 4.08% | 2.04% | 4.08% | 4.08% | 2.04% | 4.08% | 2.04% |

*This is the value generated in the gene-specific qRT-PCR assays described e.g., in the Examples. Theoretically, the output gene-specific genomes distribution should equal the input plasmid distribution, keeping in mind variability and limitations of the assays.
**This is the theoretical percentage of the vector particles containing any given input genome.

Thus, using the viral vector packaging system described herein, two or more different viral vector genomes can be used. In this regard, 2, 3, 4, 5, 6 7, 8, 9, 10, or more different viral vector genome plasmids can be added to the packaging system in various different ratios to achieve the multigenome retroviral vector preparation desired. In certain embodiments, 2-9, 2-8, 2-7, 2-6, 2-5, 2-4, 3-9, 3-8, 3-7, 3-6, 3-5, 3-4, 4-9, 4-8, 4-7, 4-6, or 4-5 different viral vector genome plasmids can be added to the packaging system in various different ratios to achieve the multigenome retroviral vector preparation desired.

In certain embodiments, the different viral vector genomes are the same except for the sequence of interest. In this regard, the viral vector genomes will have the same promoter for each sequence of interest. In other embodiments, one or more of the different viral vector genomes may have a different promoter. Thus, in certain embodiments, a different promoter may be used for different sequences of interest. Promoters and expression control sequences are known to the skilled person and are described in more detail elsewhere herein.

Moreover, as described in more detail elsewhere herein (see Section B. Lentiviral Vector Genome, subsection 3. Dimer Initiation Site (DIS) sequences), the present invention provides an additional advantage of being able to control the proportions of heterozygous or homozygous vector particles in any given multigenome preparation by modifying the dimer initiation signal of each retroviral vector genome to either promote homozygous interactions or heterozygous interactions. Furthermore, the present invention provides the advantage of being able to control the specific pairing of the input vector genomes. Thus, in certain embodiments, more than two different viral vector genome plasmids may be used in the packaging systems described herein. For example, 2, 3, 4, 5, 6, 7, 8, 9, 10, or even more different vector genome plasmids, two or more of them containing a DIS sequence to promote a particular pairing event (and thus, a particular homozygous or heterozygous viral vector particle), can be used in the packaging systems described herein.

Thus, the present invention enables the rapid construction of off-the-shelf, semi-personalized and personalized cancer vaccines with superior immunogenicity and breadth of protection compared to current state-of-the-art approaches in constructing vectored cancer vaccines.

Expression of multiple transgenes from multigenome retroviral vector preparations addresses problems of cloning of multicistronic vectors which require optimization of the positioning of the transgenes of interest in the transfer vector genome. Multigenome viral vectors can be generated much faster by transfecting producer/packaging cells with a mix of plasmids comprising multiple retroviral transfer vectors (retroviral genomes) each expressing a different transgene.

The present invention allows for creating personalized cancer vaccines based on vector mixes generated through multi-plasmid transfections using off-the-shelf transfer vectors. This also allows for creating vaccines composed of different transgenes whose mechanism of action benefits from co-expression within the same cell in vivo.

As used herein, the mixed populations of viral vectors generating using the methods herein may be referred to as "multigenome" viral vectors or multigenome viral vector preparations. This helps to distinguish the vectors herein from simply taking two viral vector preps and admixing them once they are produced. As would be clear to the skilled person, such admixed viral vector preps do not contain any heterozygous viral particles. The multigenome viral vectors herein, as described above, may comprise a mixture of particles, some comprising homozygous genomes and some comprising heterozygous genomes. A variety of multigenome populations of viral vectors can be produced using the present invention (see, e.g., as a non-limiting example, Tables 1 and 2). The multigenome viral vector preparations may comprise various ratios of homozygous and heterozygous viral vector particles depending on the input vector genomes used (e.g., using various dimer initiation signal sequences to promote either homozygous or heterozygous interactions or by using different viral vector genomes all comprising the same DIS sequence and controlling the output population by modifying the amount of input vector genome plasmids used in the packaging system). In one embodiment, where two vector genomes are used in the packaging system (vector genomes A and B), the output multigenome preparation may comprise particles comprising AA homozygous genomes, BB homozygous genomes, each at a particular ratio, and in addition comprises AB heterozygous particles at a particular ratio. In another embodiment, the output multigenome preparation may comprise at least about 50% particles comprising homozygous genomes (AA and BB homozygous genomes) and comprises about 50% AB heterozygous particles. In certain embodiments, the output multigenome preparation may comprise at least about 60% particles comprising homozygous genomes (AA and BB homozygous genomes) and comprises about 40% AB heterozygous particles. In certain embodiments, the output multigenome preparation may comprise at least about 70% particles comprising homozygous genomes (AA and BB homozygous genomes) and comprises about 30% AB heterozygous particles. In certain embodiments, the output multigenome preparation may comprise at least about 80% particles comprising homozygous genomes (AA and BB homozygous genomes) and comprises about 20% AB heterozygous particles.

In certain embodiments, it may be desirable to have as high a percentage of heterozygous particles in the multigenome viral vector preparation as possible. In this regard, the present invention provides multigenome viral vector preparations and methods for producing multigenome viral vector preparations comprising at least 60% heterozygous viral vector particles. In certain embodiments, the present invention provides a multigenome viral vector preparation comprising from about 50% to about 99% heterozygous viral vector particles. In another embodiment, the present disclosure provides a multigenome viral vector preparation comprising at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or even 100% heterozygous viral vector particles. In certain embodiments, the present disclosure provides a multigenome viral vector preparation comprising from about 40% to about 80%, about 45% to about 75%, about 50% to about 70%, or about 55% to about 65% heterozygous viral vector particles. As described herein, the present invention provides specific viral vector genomes, methods and packaging systems for making mixed viral vector preparations comprising the percentages of heterozygous viral vector particles described herein.

In certain embodiments, the multigenome viral vector preparations are characterized by measuring the percentage of a particular specific genome as compared to the total genomes titer of a particular preparation (see e.g., Example 1). In this regard, in certain embodiments, the present disclosure provides multigenome viral vector preparations comprising from about 2% to about 95% of a specific genome in the preparation. In certain embodiments, the multigenome viral vector preparations may comprise from about 5% to about 70%, from about 10% to about 60%, from about 15% to about 50% of a specific genome in the preparation. Depending on the number of input vector genome plasmids and the ratio of each used, the percentage of a particular specific genome in the final multigenome lentiviral vector preparation will vary (see e.g., Tables 2 and 3).

The multigenome viral vector preparations may comprise vector genomes having any combination of the sequences of interest described herein. As a non-limiting example, a multigenome viral vector preparation may be made using three different viral vector genomes each encoding a different tumor antigen and also include one or more viral vector genomes encoding an immunomodulatory molecule. Illustrative examples of combinations of viral vector genomes to produce multigenome viral vector preparations include, but are not limited to: 1) LV-NYESO1, LV-MAGEA3, LV-MAGEA10, LV-ScFvanti-CTLA4; 2) LV-NYESO1, LV-MAGEA3, LV-MAGEA10, LV-IL12; 3) 2) LV-NYESO1, LV-MAGEA3, LV-MAGEA10, LV-IL23; 4) LV-NY-ESO-1, LV-MAGEA3, LV-MAGEA10, LV-CD40; 5) LV-MAGEA1, LV-MAGEA3, LV-MAGEA4, LV-MAGEA10; 6) LV-NYESO1, LV-MAGEA3, LV-MAGEA10, LV-ScFvanti-PD1; 7) LV-NYESO1, LV-MAGEA3, LV-MAGEA10, LV-ScFvanti-PDL1; 8) LV-NYESO1, LV-MAGEA3, LV-MAGEA10, LV-ScFvanti-PDL1, LV-ScFvanti-CTLA4.

In certain embodiments, a multigenome viral vector preparation may be made using four or more different viral vector genomes each encoding a different tumor antigen, with or without one or more viral vector genomes encoding an immunomodulatory molecule. An illustrative example of combinations of viral vector genomes to produce multigenome viral vector preparations include, but are not limited to: multiple MAGE proteins, with or without an immunomodulatory molecule (e.g., MAGEA1, MAGEA3, MAGEA4, MAGEA10, with or without IL-12).

In certain embodiments, a multigenome viral vector preparation may be made using multiple different viral vector genomes each encoding a different tumor antigen, one or more viral vector genomes each encoding one or more neoantigens, with or without one or more viral vector genomes encoding an immunomodulatory molecule. As a non-limiting example, combinations of viral vector genomes to produce multigenome viral vector preparations include, but are not limited to: 1) multiple MAGE proteins in addition to one or more neoantigens, with or without an immunomodulatory molecule (e.g., any combination of one or more of MAGEA1, MAGEA3, MAGEA4, MAGEA10, a neoantigen cassette comprising multiple neoantigens, with or without IL-12).

As would be understood by the skilled person, the multigenome viral vector preparation will contain a mixture of different heterozygous and homozygous viral particles (see e.g., Table 2 which describes the different possible particles in a preparation using three viral vector genomes).

In certain embodiments, the mixed viral vector particle preparation comprises one or more heterozygous viral vector particles wherein the heterozygous viral vector particle comprises a viral vector genome encoding an antigen and a viral vector genome encoding an immunomodulatory molecule. As further nonlimiting examples, in one embodiment, a heterozygous viral vector particle comprises a first vector genome encoding a first antigen, and a second vector genome encoding a second antigen wherein the second antigen is different from the first antigen. In certain embodiments, a heterozygous viral vector particle comprises a 1st vector genome encoding a full-length tumor antigen, and a 2nd vector genome encoding one or more neoantigens or a cassette of neoantigen epitopes. In a further embodiment, a heterozygous viral vector particle comprises a 1st vector genome encoding an antigen and a 2nd vector genome encoding a checkpoint inhibitor molecule. In an additional embodiment, a heterozygous viral vector particle comprises a 1st vector genome encoding an antigen and a 2nd vector genome encoding a TLR agonist.

Any of a variety of methods already known in the art may be used to produce lentiviral particles whose genome comprises an RNA copy of the viral vector genome as described herein. In one method, two or more viral vector genomes as described elsewhere are introduced into a packaging cell line that contains all the components necessary to package viral genomic RNA, transcribed from the viral vector genome, into viral particles. Alternatively, the viral vector genomes may comprise one or more genes encoding viral components in addition to the one or more sequences of interest. In order to prevent replication of the genome in the target cell, however, endogenous viral genes required for replication will usually be removed and provided separately in the packaging cell line in trans.

In general, the retroviral vector particles are produced by a cell line that is transfected with one or more plasmid vectors containing the components necessary to generate the particles. Two or more different vector genome plasmids (at predetermined ratios), each encoding a protein of interest (e.g., a full-length antigen or immune modulator or neoantigen epitope cassette), are mixed prior to transfection of production cells together with other constant plasmids coding for the proteins forming the vector particle.

These vector particles are typically not replication-competent, i.e., they are only capable of a single round of infection. Most often, multiple plasmid vectors are utilized to separate the various genetic components that generate the retroviral vector particles, mainly to reduce the chance of recombination events that might otherwise generate replication competent viruses. A single plasmid vector having all of the retroviral components can be used if desired, however. As one example of a system that employs multiple plasmid vectors, a cell line is transfected with at least two plasmids containing the viral vector genomes (i.e., the vector genome plasmids), including the LTRs, the cis-acting packaging sequence, and the sequence(s) of interest, which are often operably linked to a heterologous promoter, at least one plasmid encoding the virus enzymatic and structural components (i.e., the packaging plasmid that encodes components such as, Gag and Pol), and at least one envelope plasmid encoding an envelope glycoprotein. Additional plasmids can be used to enhance retrovirus particle production, e.g., Rev-expression plasmids and/or Vpx expression plasmids, as described herein and known in the art. Viral particles bud through the cell membrane and comprise a core that includes a genome containing the sequence of interest and an envelope glycoprotein that targets dendritic cells. When the envelope glycoprotein is Sindbis virus E2 glycoprotein, the glycoprotein is engineered to have reduced binding to heparan sulfate compared to the reference strain HR.

Transfection of packaging cells with plasmid vectors of the present invention can be accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. (2001. Non-Viral Vectors in Cancer Gene Therapy: Principles and Progresses. Anticancer Drugs). Cationic lipid or salt treatment methods are typically employed, see, for example, Graham et al. (1973. Virol. 52:456; Wigler et al. (1979. Proc. Natl. Acad. Sci. USA 76:1373-76). The calcium phosphate precipitation method is most often used. However, other methods for introducing the vector into cells may also be used, including nuclear microinjection and bacterial protoplast fusion.

As described further herein in Tables 1, 2, 3 and the Examples, the ratio of input retroviral genome plasmid for each genome desired in the multigenome retroviral vector preparation can be varied depending on the desired output.

The packaging cell line provides the components, including viral regulatory and structural proteins, that are required in trans for the packaging of the viral genomic RNA into retroviral vector particles. The packaging cell line may be any cell line that is capable of expressing retroviral proteins and producing functional retroviral vector particles. Some suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells. The packaging cell line may stably express the necessary viral proteins. Such a packaging cell line is described, for example, in U.S. Pat. No. 6,218,181. Alternatively a packaging cell line may be transiently transfected with nucleic acid molecules encoding one or more necessary viral proteins along with the viral vector genome. The resulting viral particles are collected and used to infect a target cell. The gene(s) encoding envelope glycoprotein(s) is usually cloned into an expression vector, such as pcDNA3 (Invitrogen, CA USA). Eukaryotic cell expression vectors are well known in the art and are available from a number of commercial sources. Packaging cells, such as 293T cells are then co-transfected with the viral vector genome encoding a sequence of interest, at least one plasmid encoding virus packing components, and a vector for expression of the targeting molecule. The envelope is expressed on the membrane of the packaging cell and incorporated into the viral vector.

In one scenario, one or more vectors are used to introduce polynucleotide sequences into a packaging cell line for the preparation of a retroviral vector particle pseudotyped with a VSVg envelope or a Sindbis virus envelope glycoprotein such as E2, as described herein. The vectors can contain polynucleotide sequences encoding the various components of the virus including the VSVg or Sindbis virus envelope, the vector genome plasmids, each containing a sequence(s) of interest (e.g., an antigen or other sequences of interest), and any components necessary for the production of the virus that are not provided by the packaging cell.

In yet other scenarios, packaging cells are co-transfected with at least two viral vector genomes encoding the proteins of interest and one or more additional vectors. For example, in addition to the viral vector genomes comprising the sequence(s) of interest (and optionally one or more additional sequences of interest), a second vector carries the genes encoding an envelope protein, such as a VSVg envelope or a modified (also called a variant) Sindbis virus envelope. In some situations, the plasmids containing the viral vector genomes include a polynucleotide sequence encoding additional selected immunomodulatory molecules, including non-limiting examples of a chemokine, a cytokine, a DC maturation factor, or a factor that regulates immune checkpoint mechanisms.

In certain embodiments, the packaging system is a so-called fourth generation packaging system whereby the gag-pol gene is further separated onto two separate plasmids. Such systems are known in the art and described for example in U.S. Pat. Nos. 6,365,150, 6,955,919, 7,311,907 and 8,034,620. Such packaging systems are also commercially available from, e.g., Clontech/Takara, San Diego, Calif.). In certain embodiments, the pol gene may be fused to vpr to ensure transport of the reverse transcriptase/integrase protein into the recombinant viral particle.

In certain embodiments, the packaging system is as described in WO2013/149167 or WO2011/011584.

In some or any embodiments, the retroviral vector particles described herein comprise a SAMHD1 inhibitor. In certain embodiments, the SAMHD1 inhibitor is a Vpx protein or a Vpr protein. In certain embodiments, the retroviral vector particles described herein comprise a Vpx protein or a variant thereof (see e.g., WO2013/149167). In some or any embodiments, the variant retains the ability to inhibit SAMHD1.

In some embodiments the retroviral vector is pseudotyped with an arbovirus envelope glycoprotein, such as a Sindbis envelope protein. The Sindbis virus envelope protein contains four N-linked glycans—two on the E2 protein and two on the E1 protein. Two N-glycans of the virus produced in mammalian cells in the absence of a mannosidase I inhibitor have a high-mannose structure (one E2 N-linked glycan and one E1 N-linked glycan), while the remaining two have a complex structure. The two complex structure N-glycans are exposed on the surface of the envelope protein, while the two high-mannose structure N-glycans are buried within the center of the trimer of the envelope proteins. Sindbis virus particles with complex N-linked glycans do not bind DC-SIGN as efficiently as particles with less complex, highly mannosylated glycoproteins.

In certain embodiments, the viral particles are produced in mammalian cells in the presence of the mannosidase I inhibitor, such as kifunensine (see e.g., WO2013/149167). Thus, in some or any embodiments, a virus packaging cell is cultured in the presence of a mannosidase I inhibitor. In some or any embodiments, the mannosidase I inhibitor is kifunensine. In some embodiments, kifunensine is present in the media at a concentration of about 0.01 µg/ml to about 1 mg/ml, about 0.1 µg/ml to about 10 µg/ml, about 0.1 µg/ml to about 9 µg/ml, about 0.1 µg/ml to about 8 µg/ml, about 0.1 µg/ml to about 7 µg/ml, about 0.1 µg/ml to about 6 µg/ml, about 0.1 µg/ml to about 5 µg/ml, about 0.1 µg/ml to about 4 µg/ml, about 0.1 µg/ml to about 3 µg/ml, about 0.1 µg/ml to about 2 µg/ml, about 0.1 µg/ml to about 1 µg/ml, about 0.25 µg/ml to about 10 µg/ml, about 0.25 µg/ml to about 9 µg/ml, about 0.25 µg/ml to about 8 µg/ml, about 0.25 µg/ml to about 7 µg/ml, about 0.25 µg/ml to about 6 µg/ml, about 0.25 µg/ml to about 5 µg/ml, about 0.25 µg/ml to about 4 µg/ml, about 0.25 µg/ml to about 3 µg/ml, about 0.25 µg/ml to about 2 µg/ml, or about 0.25 µg/ml to about 1 µg/ml.

In some or any embodiments wherein a pseudotyped retroviral vector particle comprises a Sindbis virus E2 glycoprotein and a Vpx protein, the retroviral particles are produced in the presence of a mannosidase I inhibitor. In some embodiments, the mannosidase inhibitor is deoxymannojirimycin (DMNJ). In preferred embodiments, the mannosidase inhibitor is kifunensine. In some embodiments, DMNJ is present in the media at a concentration of about 1.0 µg/ml to about 1.0 mg/ml, about 1.0 µg/ml to about 900 µg/ml, about 1.0 µg/ml to about 800 µg/ml, about 1.0 µg/ml to about 700 µg/ml, about 1.0 µg/ml to about 600 µg/ml, about 1.0 µg/ml to about 500 µg/ml, about 1.0 µg/ml to about 400 µg/ml, about 1.0 µg/ml to about 300 µg/ml, about 1.0 µg/ml to about 200 µg/ml, about 1.0 µg/ml to about 100 µg/ml, about 50 µg/ml to about 500 µg/ml, about 50 µg/ml to about 400 µg/ml, about 50 µg/ml to about 300 µg/ml, about 50 µg/ml to about 200 µg/ml, about 50 µg/ml to about 100 µg/ml, about 100 µg/ml to about 500 µg/ml, about 100 µg/ml to about 400 µg/ml, about 100 µg/ml to about 300 µg/ml, about 100 µg/ml to about 200 µg/ml, about 200 µg/ml to about 500 µg/ml, or about 200 µg/ml to about 400 µg/ml.

In some or any embodiments, a pseudotyped retroviral vector particle produced in the presence of a mannosidase I inhibitor (e.g., kifunensine) comprises an envelope glycoprotein (e.g., Sindbis virus E2), wherein at least 60% of N-linked glycans comprise a Mannose5 (Man5), Man6, Man7, Man8, and/or Man9 structure. In some embodiments, at least 65%, at least 70%, at least 75%, at least 80%, at least 85%, at least 90%, at least 95%, at least 96%, at least 97%, at least 98%, at least 99%, or 100% of N-linked glycans comprise a Man5, Man6, Man7, Man8, and/or Man9+ structure.

In one scenario, one or more vectors are used to introduce polynucleotide sequences into a packaging cell line for the preparation of a retroviral vector particle pseudotyped with a Sindbis virus envelope glycoprotein such as E2, as described herein. In some embodiments, the retroviral vector particle is highly mannosylated. In some embodiments, the retroviral vector particle also comprises a Vpx protein or variant thereof. In yet other embodiments, the retroviral vector particle is highly mannosylated and comprises a Vpx protein or variant thereof. The vectors can contain polynucleotide sequences encoding the various components of the virus including the Sindbis virus envelope, a sequence(s) of interest (typically encoding an antigen), and any components necessary for the production of the virus that are not provided by the packaging cell.

The glycosylation profile of a viral envelope protein can be determined by any method known in the art. For example, gel shift assays on viral glycoproteins treated with glycosidases (e.g., EndoH or PNGaseF) or left untreated may be compared. Other methods include cleaving glycans from the viral glycoproteins and separating and identifying the components via HPLC and mass spectrometry methods.

Production of virus is measured as described herein and expressed as IU per volume. IU is infectious unit, or alternatively transduction units (TU); IU and TU can be used interchangeably as a quantitative measure of the titer of a viral vector particle preparation. As described herein, virus is produced in which the genome can express a product that is readily measurable. A fluorescent protein, green fluorescent protein, is preferred. The retroviral vector is typically non-integrating. The virus is then administered to target cells and the number of target cells that express GFP is determined, such as by flow cytometry. The titer is then calculated. The titer is preferably as high as possible, but at least $1\times10^5$ IU/mL, at least $3\times10^5$ IU/mL, at least $1\times10^6$ IU/mL, at least $3\times10^6$ IU/mL, or at least $1\times10^7$ IU/mL of cell supernatant (before any concentration). Alternatively, the titer is at least 80%, at least 90%, at least 95%, at least 100% of the titer of the same retroviral vector pseudotyped in the same cells with VSV-G envelope.

In certain embodiments, production of virus is measured as genomes/ml. Genomes can be measured using various methods known in the art, such as RT-PCR, PCR, qPCR, qdd (digital droplet) PCR and RNASCOPE or DNASCOPE.

A variety of methods can be used for determining the makeup of a particular retroviral vector particle preparation described herein comprising reassortants. For example, gene-specific qRT-PCR based on primer sets specific for each sequence of interest present in the viral vector preparation can be used. In certain embodiments, gene specific qRT-PCR in combination with flow cytometry can be used. Other single cell methodologies can also be used such as digital droplet PCR (see e.g., Bio-Rad QX-100 RT-ddPCR system, Bio-Rad, Hercules, Calif.); see also Hindson B J et al. (2011). High-throughput droplet digital PCR system for absolute quantitation of DNA copy number. Anal Chem 83(22): 8604-8610; Pinheiro L B et al. (2012). Evaluation of a droplet digital polymerase chain reaction format for DNA copy number quantification. Anal Chem 84, 1003-1011). Other methods include RNASCOPE and DNASCOPE (Advanced Cell Diagnostics, Inc., Newark, Calif.) (see e.g., Deleage et al., Pathogens and Immunity 2016 Spring; 1(1): 68-106; Wang et al., J Mol Diagn. 2012; 14(1):22-9; Player et al., J Histochem Cytochem. 2001; 49(5):603-12). These and other methods for determining the homozygous versus heterozygous makeup of a particular viral vector preparation or viral particles or transduced cells would be known to the person of skill in the art.

D. Delivery of the Virus

Compositions comprising the multigenome viral vector preparations may be delivered to a target cell in any way that allows the virus to contact the target cells in which delivery of a polynucleotide of interest is desired. Depending on the application, different cells may be targeted. In certain embodiments, tumor cells are targeted. In other embodiments, dendritic cells (DCs) are targeted. In further embodiments, T cells or B cells are targeted. The retroviral vectors of the present invention can be used in vitro (e.g., for ex vivo modification of cells) or directly in vivo.

At times, a suitable amount of a composition comprising the multigenome viral vector preparation will be introduced into a human or other animal directly (in vivo), e.g., though injection into the body. Suitable animals include, without limitation, any mammal, such as horses, dogs, cats, cattle, pigs, sheep, rabbits, chickens or other birds. Viral particles may be injected by a number of routes, such as intravenous, intramuscular, intra-dermal, subcutaneous, intranodal, intra-tumoral, intra-peritoneal cavity, or mucosal. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

Alternatively, target cells are provided and contacted with the viral particles in vitro, such as in culture plates. The target cells are typically populations of cells comprising T cells or dendritic cells obtained from a healthy subject or a subject in need of treatment or in whom it is desired to stimulate an immune response to an antigen. Methods to obtain cells from a subject are well known in the art and includes phlebotomy, surgical excision, and biopsy. Human DCs may also be generated by obtaining CD34α+ human hematopoietic progenitors and using an in vitro culture method as described elsewhere (e.g., Bancbereau et al. Cell 106, 271-274 (2001) incorporated by reference in its entirety). Appropriate T cell populations may be generated in vitro using similar methods.

The multigenome preparation may be suspended in media and added to the wells of a culture plate, tube or other container. Media containing the virus may be added prior to the plating of the cells or after the cells have been plated. Cells are typically incubated in an appropriate amount of media to provide viability and to allow for suitable concentrations of virus in the media such that transduction of the host cell occurs. The cells are preferably incubated with the virus for a sufficient amount of time to allow the virus to infect the cells. Preferably the cells are incubated with virus for at least 1 hour, at least 5 hours or at least 10 hours.

In both in vivo and in vitro delivery, an aliquot of viral particles containing sufficient number to infect the desired target cells may be used. When the target cell is to be cultured, the concentration of the viral particles is generally at least 1 IU/μL, more preferably at least 10 IU/μl, even more preferably at least 300 IU/μL, even more preferably at least $1\times10^4$ IU/μL, even more preferably at least $1\times10^5$ IU/μL, even more preferably at least $1\times10^6$ IU/μL, or even more preferably at least $1\times10^7$ IU/μL Following infection with the viral particles in vitro, target cells can be introduced (or re-introduced) into a human or other animal. The cells can be introduced into the dermis, under the dermis, or into the peripheral blood stream. The cells introduced into an animal are preferably cells derived from that animal, to avoid an adverse immune response. Cells derived from a donor having a similar immune background may also be used. Other cells that also can be used include those designed to avoid an adverse immunologic response.

Target cells may be analyzed for integration, transcription and/or expression of the sequences or gene(s) of interest, the number of copies of the gene integrated, and the location of the integration, for examples. Such analysis may be carried out at any time and may be carried out by any method known in the art.

Subjects in which a virus or virus-infected cells are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to a variety of animal species. In some instances, viral particles are delivered to a human or to human cells, such as T cells, B cells or dendritic cells, and in other instances they are delivered to an animal such as a mouse, horse, dog, cat, or mouse or to birds. As discussed herein, the viral vector is pseudotyped to confer upon it a broad host range as well as target cell specificity. One of skill in the art would also be aware of appropriate internal promoters and other elements to achieve the desired expression of a sequence of interest in a particular animal species. Thus, one of skill in the art will be able to modify the method of infecting cells from any species.

Target cells may be infected with a mixed retroviral vector particle preparation as described herein for the prevention of or treatment of a disease or disorder. In certain embodiments, target cells may be infected with a mixed retroviral vector particle preparation as described herein for the prevention of or treatment of a disease or disorder for which activation of an immune response in a patient would be beneficial. Many such diseases are well known. For example, diseases or disorders that are amenable to treatment or prevention by the methods of the present invention include, without limitation, cancers, autoimmune diseases, and infections, including viral, bacterial, fungal and parasitic infections. In one method, a disease is treated by viral particles described herein in order to deliver sequences of interest to dendritic cells, wherein expression of the sequences of interest produces a disease-specific antigen and leads to stimulation of antigen-specific cellular immune responses and humoral immune responses. Generally, the sequences of interest encode one or more antigens against which an immune response is desired, but is not normally expressed in a dendritic cell. The antigen is expressed and presented by the dendritic cell. In other embodiments, the viral vector genome may encode an immunomodulatory molecule as described herein. In certain embodiments, the viral vector particle is heterozygous and comprises a viral vector genome encoding an antigen and a viral vector genome encoding an immunomodulatory molecule, both of which are expressed in the target cells.

In a typical usage, viral particles deliver to dendritic cells sequences encoding an antigen against which an immune response is desired and a sequence encoding an immunomodulatory molecule. The delivery can be achieved by contacting cells with the virus in vitro, whereupon the infected cells are provided to a patient. Other times, delivery can be achieved by delivering the virus to a subject for infecting cells in vivo. In certain embodiments, compositions comprising multigenome preparations are delivered to a subject for infecting dendritic cells in vivo. The dendritic cells then stimulate antigen-specific T cells or B cells in a patient to induce cellular and humoral immune responses to the expressed antigen. Thus, the present disclosure provides methods of inducing an immune response in a subject, comprising administering to the subject a pharmaceutical composition comprising the multigenome retroviral vector preparations described herein. In further embodiments, the present disclosure provides methods of treating cancer in a subject, comprising administering to the subject a pharmaceutical composition comprising the multigenome viral vectors preparations described herein, wherein the SOIs encode one or more tumor associated antigens and optionally one or more checkpoint inhibitors or one or more cytokines, or a combination thereof. In another embodiment, the present disclosure provides a method of treating an infectious disease in a subject, comprising administering to the subject a pharmaceutical composition comprising a multigenome retroviral vector preparation as described herein wherein the SOIs encode an antigen associated with the infectious disease.

In other embodiments, target cells are infected either in vivo or in vitro with the virus is described herein expressing an immunomodulatory molecule. Infected cells then express immunomodulatory molecule in a patient to modulate the immune response. In such ways, a patient that is suffering from a disease or disorder is treated by generating immune cells with a desired specificity or modulated immune response with an immunomodulatory molecule.

Any antigen that is associated with a disease or disorder can be delivered to dendritic cells using the multigenome viral vectors as described herein. An antigen that is associated with the disease or disorder is identified for preparation of a viral particle that targets dendritic cells.

If contacted ex vivo, the target dendritic cells are then transferred back to the patient, for example by injection, where they interact with immune cells that are capable of generating an immune response against the desired antigen. In other embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

In certain embodiments, a viral vector particle is heterozygous and contains vector genomes each comprising a polynucleotide sequence encoding a different antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders.

In some of the multigenome vectors described herein, the particles comprise at least one vector genome that encodes an immunomodulatory molecule that activates and/or stimulates an immune response, and in certain embodiments activates and/or stimulates maturation of the DCs. In alternatives, the DCs are activated by delivery of DC maturation factors prior to, simultaneously with, or after delivery of the virus. DC maturation factors may be provided separately from administration of the virus.

The methods described herein can be used for adoptive immunotherapy in a patient. As described above, an antigen against which an immune response is desired is identified. A polynucleotide encoding the desired antigen is obtained and packaged into a recombinant multigenome viral vector preparation as described herein. Target dendritic cells are obtained from the patient and transduced with a recombinant virus containing a polynucleotide that encodes the desired antigen. The dendritic cells are then transferred back into the patient.

The multigenome viral vectors may be injected in vivo, where they infect target cells, such as DCs, and deliver the sequences of interest, typically encoding an antigen and/or immunomodulatory molecule. The amount of viral particles is at least $3\times10^6$ IU, and can be at least $1\times10^7$ IU, at least $3\times10^7$ IU, at least $1\times10^8$ IU, at least $3\times10^8$ IU, at least $1\times10^9$ IU, or at least $3\times10^9$ IU. At selected intervals, DCs from the recipient's lymphoid organs may be used to measure expression, for example, by observing marker expression, such as the antigen of interest or GFP or luciferase. Nucleic acid monitoring techniques and measurements of reverse transcriptase (RT) activity can also be used to analyze the biodistribution of viral particles. T cells from peripheral blood mononuclear cells, lymph nodes, spleens, or malignant or target pathogen-infected tissue of lentiviral vector particle-treated recipients may be measured from the magnitude and durability of response to antigen stimulation. Tissue cells other than DCs, such as epithelial cells and lymphoid cells, may be analyzed for the specificity of in vivo gene delivery.

Vaccines often include an adjuvant. The multigenome retroviral vectors described herein may also be administered along with an adjuvant. The adjuvant may be administered with the recombinant virus particles, before the recombinant virus particles, or after the recombinant virus particles. If administered with the virus particles, desirable adjuvants do not significantly disrupt the integrity of the virus particle, such as disrupting the viral membrane containing the envelope glycoproteins.

Although a typical usage of the multigenome viral vectors herein is to target DCs in vivo for induction of an immune response against an antigen, or multiple antigens, other target cells and uses are contemplated herein such as for adoptive immunotherapy, production of modified T cells (expressing a modified TCR or chimeric antigen receptor), gene therapy, etc.

A variety of adjuvants can be used in combination with the virus to elicit an immune response to the antigen encoded in the viral vector genome. Preferred adjuvants augment the intrinsic response to an antigen without causing conformational changes in the antigen that affect the qualitative form of the response. Preferred adjuvants include alum, 3 De-O-acylated monophosphoryl lipid A (MPL) (see GB 2220211). QS21 is a triterpene glycoside or saponin isolated from the bark of the Quillaja *Saponaria* Molina tree found in South America (see Kensil et al., in Vaccine Design: The Subunit and Adjuvant Approach (eds. Powell and Newman, Plenum Press, N Y, 1995); U.S. Pat. No. 5,057,540). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, Aβ can be coupled to an adjuvant. For example, a lipopeptide version of Aβ can be prepared by coupling palmitic acid or other lipids directly to the N-terminus of Aβ as described for hepatitis B antigen vaccination (Livingston, J. Immunol. 159, 1383-1392 (1997)). However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

One class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn- -glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated there from such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

Another adjuvant that can be used with the compositions herein is identified by chemical formula (I):

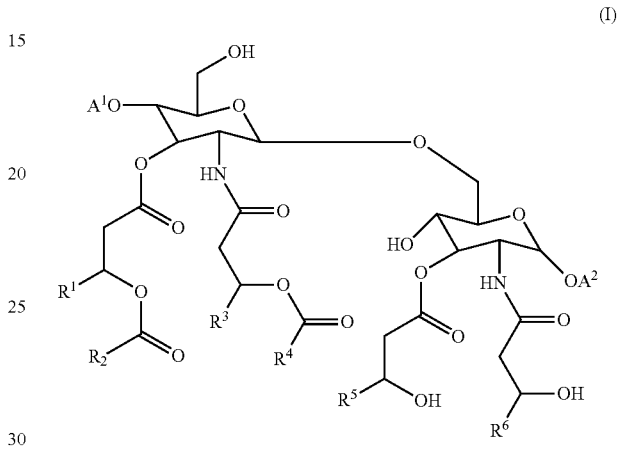

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is a GLA and has the formula shown below as E1 in combination with E10.

In certain embodiments the adjuvant has the formula shown below:

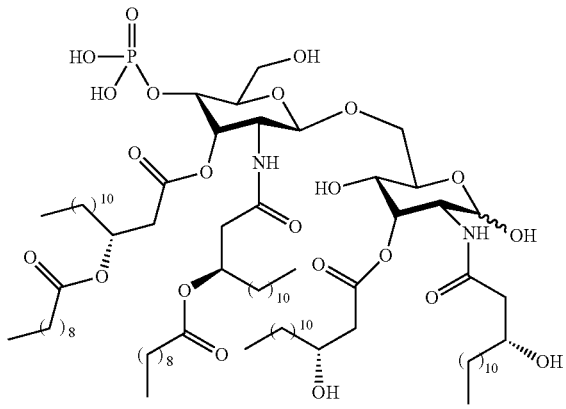

In various embodiments of the invention, the adjuvant has the chemical structure of formula (I) but the moieties A1, A2, R1, R2, R3, R4, R5, and R6 are selected from subsets of the options previously provided for these moieties, where these subsets are identified below by E1, E2, etc.

E1: A1 is phosphate or phosphate salt and A2 is hydrogen.

E2: R1, R3, R5 and R6 are C3-C21 alkyl; and R2 and R4 are C5-C23 hydrocarbyl.

E3: R1, R3, R5 and R6 are C5-C17 alkyl; and R2 and R4 are C7-C19 hydrocarbyl.

E4: R1, R3, R5 and R6 are C7-C15 alkyl; and R2 and R4 are C9-C17 hydrocarbyl.

E5: R1, R3, R5 and R6 are C9-C13 alkyl; and R2 and R4 are C11-C15 hydrocarbyl.

E6: R1, R3, R5 and R6 are C9-C15 alkyl; and R2 and R4 are C11-C17 hydrocarbyl.

E7: R1, R3, R5 and R6 are C7-C13 alkyl; and R2 and R4 are C9-C15 hydrocarbyl.

E8: R1, R3, R5 and R6 are C11-C20 alkyl; and R2 and R4 are C12-C20 hydrocarbyl.

E9: R1, R3, R5 and R6 are C11 alkyl; and R2 and R4 are C13 hydrocarbyl.

E10: R1, R3, R5 and R6 are undecyl and R2 and R4 are tridecyl.

In certain options, each of E2 through E10 is combined with embodiment E1, and/or the hydrocarbyl groups of E2 through E9 are alkyl groups, preferably straight chain alkyl groups.

The adjuvant of formula (I) may be formulated into a pharmaceutical composition, optionally with a co-adjuvant, each as discussed below. In this regard reference is made to US Patent Publication No. 2008/0131466 which provides formulations, e.g., aqueous formulation (AF) and stable emulsion formulations (SE) for GLA adjuvant, where these formulations may be utilized for any of the adjuvants of formula (I).

An adjuvant can be administered with the multigenome viral vectors of the invention as a single composition, or can be administered before, concurrent with or after administration of the recombinant virus of the invention. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously, such as alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

The compositions comprising a multigenome viral vector as described herein may also be administered simultaneously with, prior to, or after administration of one or more other therapeutic agents.

Such combination therapy may include administration of a single pharmaceutical dosage formulation which contains a heterozygous viral vector and one or more additional active agents, as well as administration of compositions comprising a heterozygous viral vector of the invention and each active agent in its own separate pharmaceutical dosage formulation. For example, a composition comprising a heterozygous viral vector and the other active agent can be administered to the patient together in a single enteral (e.g., oral) dosage composition such as a tablet or capsule, or each agent administered in separate enteral (e.g., oral) dosage formulations. Similarly, compositions comprising a heterozygous viral vector and the other active agent can be administered to the patient together in a single parenteral (e.g., any of the parenteral routes known and described herein, such as, subcutaneous, intradermal, intranodal, intratumoral or intramuscular) dosage composition such as in a saline solution or other physiologically acceptable solution, or each agent administered in separate parenteral dosage formulations. The combination therapies as described herein can be administered by the same route or may be administered using different routes. Where separate dosage formulations are used, the compositions comprising heterozygous viral vector and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of compositions comprising a multigenome viral vector preparation of this disclosure in combination with one or more other therapeutic agents (e.g. other anti-cancer agents, or other palliative or adjunctive therapy). In certain embodiments, such therapeutic agents may be accepted in the art as a standard treatment for a particular cancer as described herein. Exemplary therapeutic agents contemplated include cytokines, growth factors, steroids, NSAIDs, DMARDs, anti-inflammatories, immune checkpoint inhibitors, chemotherapeutics, radiotherapeutics, or other active and ancillary agents.

In one embodiment, compositions comprising a multigenome viral vector preparation are administered in combination with one or more cancer therapeutic agents, including one or more chemotherapeutic agents. Examples of cancer therapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such asTargretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In another embodiment, the compositions comprising a multigenome viral vector preparation herein are administered in combination with another immunostimulatory agent. Such immunostimulatory agents include, but are not limited to, N-acetylmuramyl-L-alanine-D-isoglutamine (MDP), glucan, IL-12, GM-CSF, interferon-γ and anti-CD40 antibodies or other antibodies that bind to and activate co-stimulatory pathways (e.g., CD28, ICOS, OX40, CD27 and the like).

In one embodiment, the multigenome viral vector compositions herein are administered in combination with one or more immune checkpoint inhibitors. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides immune checkpoint inhibitors that can be administered in combination with the GLA compositions without antigen. Such combination therapies work in concert to enhance an anti-cancer immune response. Certain viruses have also developed mechanisms to co-opt immune checkpoint pathways. Therefore, in certain embodiments, such combination therapy may be used to enhance an anti-viral immune response.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+(αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

In a further embodiment, the multigenome viral vector compositions herein are administered in combination with other TLR4 agonists, or a TLR8 agonist, or a TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In an additional embodiment, the multigenome viral vector compositions herein are administered in combination with a cytokine. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, but not limited to, IL-1, IL-1alpha, IL-2, IL-3, IL-4, IL-5, IL-6, IL-7, IL-8, IL-9, IL-10, IL-11, IL-12; IL-15, IL-18, IL-21, IL-23, IL-27, TNF; and other polypeptide factors including LIF and kit ligand (KL). As used herein, the term cytokine includes proteins from natural sources or from recombinant cell culture, and biologically active equivalents of the native sequence cytokines.

In certain embodiments, the compositions comprising multigenome viral vector preparations as described herein may be administered in combination with chloroquine, a lysosomotropic agent that prevents endosomal acidification and which inhibits autophagy induced by tumor cells to survive accelerated cell growth and nutrient deprivation. More generally, the compositions comprising heterozygous viral vectors as described herein may be administered in combination with therapeutic agents that act as autophagy inhibitors, radiosensitizers or chemo sensitizers, such as chloroquine, misonidazole, metronidazole, and hypoxic cytotoxins, such as tirapazamine. In this regard, such combinations of a heterozygous viral vector with chloroquine or other radio or chemo sensitizer, or autophagy inhibitor, can be used in further combination with other cancer therapeutic agents or with radiation therapy.

In another embodiment, the compositions comprising multigenome viral vector preparation as described herein may be administered in combination with small molecule drugs which are known to result in killing of tumor cells with concomitant activation of immune responses, termed "immunogenic cell death", such as cyclophosphamide, doxorubicin, oxaliplatin and mitoxantrone. Furthermore, combinations with drugs known to enhance the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, furthermore proteasome inhibitors (e.g. bortezomib), shikonin (the major constituent of the root of Lithospermum erythrorhizon) and oncolytic viruses, such as TVec (talimogene laherparepvec). In other embodiments, the compositions comprising heterozygous viral vectors as described herein may be administered in combination with epigenetic therapies, such as DNA methyltransferase inhbitors (e.g. Decitabine, 5-aza-2'-deoxycytidine) which may be administered locally or systemically.

In another embodiment, the compositions comprising a multigenome viral vector preparation as described herein may be administered in combination with one or more antibodies that increase ADCC uptake of tumor by DCs. Thus, the present invention contemplates combining compositions comprising a multigenome viral vector preparation with any molecule that induces or enhances the ingestion of a tumor cell or its fragments by an antigen presenting cell and subsequent presentation of tumor antigens to the immune system. These molecules include agents that induce receptor binding (such as Fc or mannose receptors) and transport into the antigen presenting cell such as antibodies, antibody-like molecules, multi-specific multivalent molecules and polymers. Such molecules may either be administered intratumorally with the composition comprising heterozygous viral vector, or administered by a different route. For example, a composition comprising heterozygous viral vector as described herein may be administered intratumorally in conjunction with intratumoral injection of rituximab, cetuximab, trastuzumab, Campath, panitumumab, ofatumumab, brentuximab, pertuzumab, Ado-trastuzumab emtansine, Obinutuzumab, anti-HER1, -HER2, or -HER3 antibodies (e.g., MEHD7945A; MM-111; MM-151; MM-121; AMG888), anti-EGFR antibodies (e.g. Nimotuzumab, ABT-806), or other like antibodies. Any multivalent scaffold that is capable of engaging Fc receptors and other receptors that can induce internalization may be used in the combination therapies described herein—e.g. peptides and/or proteins capable of binding targets that are linked to Fc fragments or polymers capable of engaging receptors.

In certain embodiments, the combination of multigenome viral vector preparations with such antibodies may be further combined with an antibody that promotes a co-stimulatory signal (e.g., by blocking inhibitory pathways), such as anti-CTLA-4, or that activates co-stimulatory pathways such as an anti-CD40, anti-CD28, anti-ICOS, anti-OX40, anti-CD27 antibodies and the like.

The compositions comprising a multigenome viral vector preparation may be administered alone or in combination with other known cancer treatments, such as radiation therapy, immune checkpoint inhibitors, chemotherapy or other cancer therapeutic agents, transplantation, immunotherapy, hormone therapy, photodynamic therapy, etc. The compositions may also be administered in combination with antibiotics.

E. Pharmaceutical Compositions and Kits

Also contemplated herein are pharmaceutical compositions and kits containing a multigenome viral vector preparation provided herein and one or more components. Pharmaceutical compositions can include the multigenome viral vectors as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing viral particles as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The multigenome viral vectors provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides encoding one or more sequences of interest are also contemplated herein. The kit may include at least one plasmid encoding virus packaging components and vector encoding a viral envelope, such as VSVg or a Sindbis virus E2 glycoprotein variant. Some kits will contain at least one plasmid encoding virus packaging components, a vector encoding Sindbis virus E2 glycoprotein variant, and two viral vector genome plasmids, one vector genome encoding an antigen and one vector genome encoding an immunomodulatory molecule.

Kits comprising a viral vector encoding one or more sequences of interest and optionally, a polynucleotide sequence encoding an immunomodulatory molecule are also contemplated herein. In some kits, the kit includes at least one plasmid encoding virus packaging components and a vector encoding a viral envelope glycoprotein.

A kit may also contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as an immunomodulatory molecule or other therapeutic agen, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

As used herein and in the appended claims, the singular forms "a," "and," and "the" include plural referents unless the context clearly dictates otherwise. Thus, for example, reference to "an antigen" includes a plurality of such antigens, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The following examples are offered by way of illustration, and not by way of limitation.

EXAMPLES

Example 1

Multigenome Lentiviral Vectors Induce Robust CD8 T Cell Responses to Two Antigens NY-ESO-1/MAGE-A3 re-assortant (multigenome) lentiviral vector particles were prepared using standard transfection protocols with the exception that both the NY-ESO-1 and the MAGE-A3 vector genome plasmids were used to transfect the packaging cells. A variety of transfection protocols known in the art can be used. A typical protocol used involves calcium phosphate (CaPO4)-mediated transient transfection of 293T cells (293LTV cell line; CELL BIOLABS INC, LTV-100). 293T cells were transfected with six plasmids precipitated together with CaPO4. The following six plasmids were used to produce multigenome lentiviral vector preparations and correspond to the following: i) lentiviral vector genome expressing NY-ESO-1; ii) lentiviral vector genome expressing MAGE-A3; iii) HIV Rev encoding plasmid; iv) HIV Gag/Pol encoding plasmid; and, v) plasmid encoding vpx; vi) envelope encoding plasmid (in this experiment, the envelope was a modified Sindbis envelope glycoprotein as previously described in e.g., WO2011/011584). For typical transfection protocols, 1 mg of lentiviral vector genome plasmid is used. In this case, the total amount of vector genome plasmid (1 mg) was kept the same but split between the two lentiviral vector genome plasmids used. So, 0.5 mg of each vector genome (MAGE-A3 and NY-ESO-1) was used for the transfection. The lentiviral vector genomes all contained the same palindromic dimer initiation site (DIS) sequence. In particular, the DIS sequence is GCGCGC (SEQ ID NO:1). Therefore, in this multigenome preparation, the predicted ratios of homozygous versus heterozygous particles are as described in Table 1, e.g. 25/25/50 ratio.

After vector purification, the viral titers were determined using a gene-specific qRT-PCR based on primer sets specific for NY-ESO-1 and MAGE-A3. Total genomes titers for the entire multigenome viral preparation were measured using PCR primers that amplify all genomes regardless of sequence of interest. The percentage of specific genomes present in the resulting preparation was then calculated as the specific titer over total genomes titer (e.g., NYESO1 genomes=5.1E10/1.2E11=42.5%). The titers are shown in Table 4 below. As shown, the multigenome lentiviral vector preparation contains NY-ESO-1 as well as MAGE-A3 vector RNA and at the expected ratios given the 50/50 ratio of input plasmid. Generally, the genomes assays being used have about a 2-fold variability. Based on this, the titers were within the expected ratios: 42.5% NYESO1 and 42% MAGEA3 in the multigenome lentiviral preparation.

Figure 3:
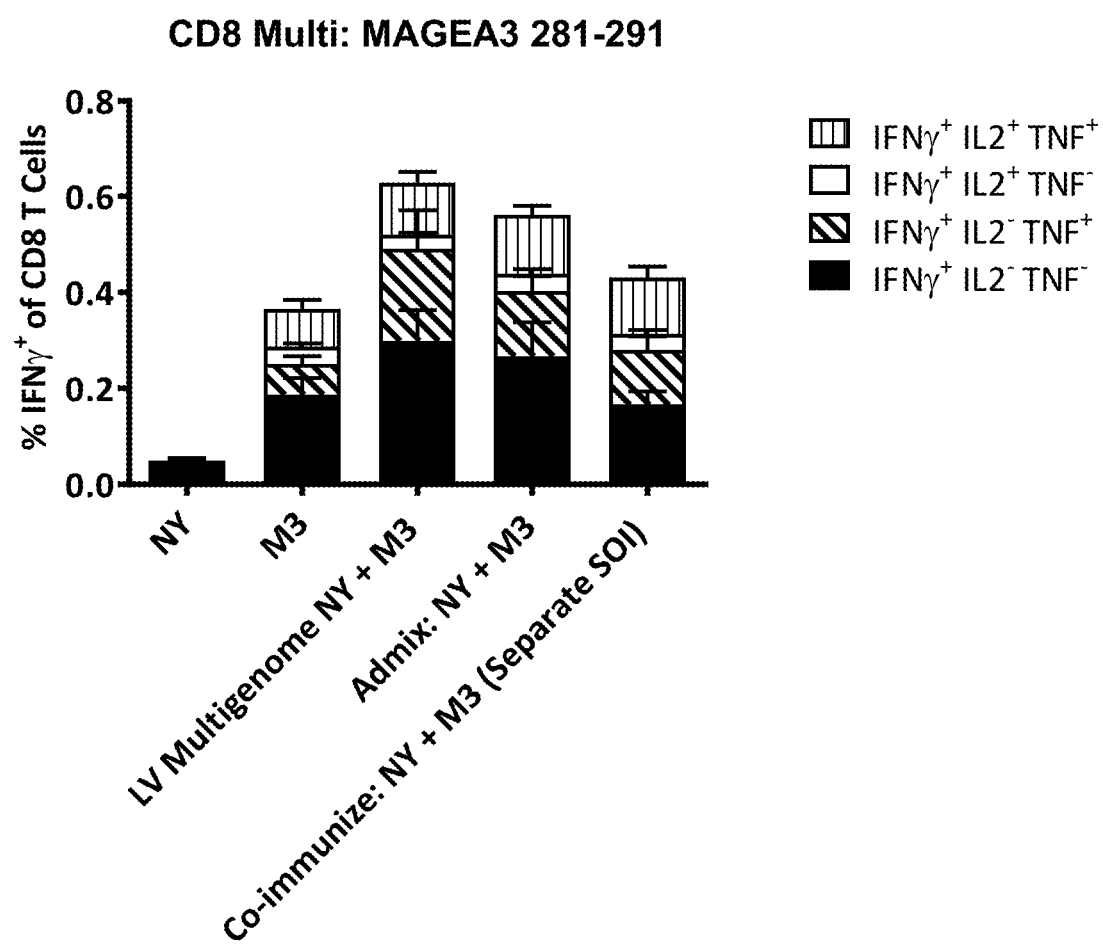
FIG. 3 is a bar graph summarizing the CD8+ T-cell immune responses against MAGE-A3 in BALB/c mice induced by single, admixed, co-immunized and multigenome viral vector preps.
Figure 4:
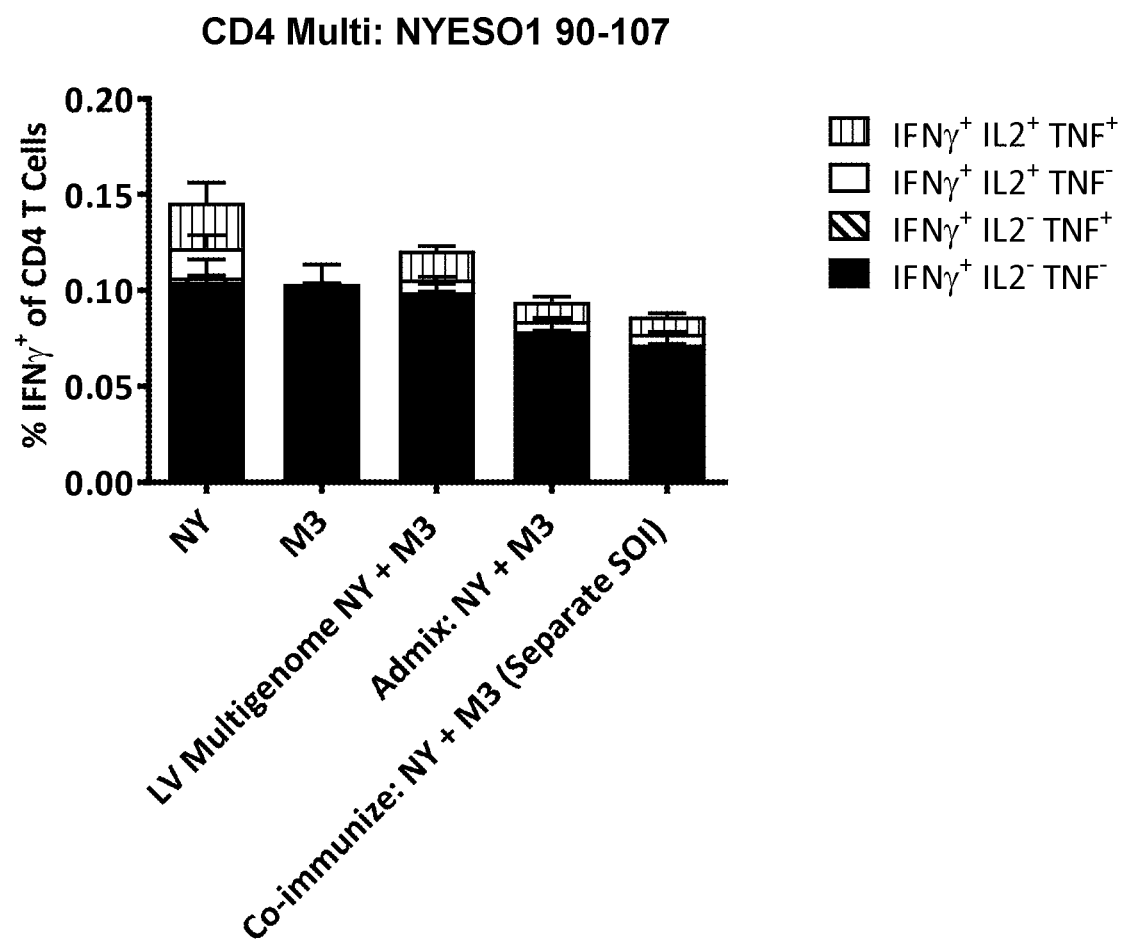
FIG. 4 is a bar graph summarizing the CD4+ T-cell immune responses against NY-ESO-1 in BALB/c mice induced by single, admixed, co-immunized and multigenome viral vector preps.

NYESO1 CD8 T-cell responses (FIG. 2), anti-MAGE-A3 CD8 T-cell responses (FIG. 3), and anti-NYESO-1 CD4 T-cell responses (FIG. 4).

Example 2

In Vivo Immunogenicity Effect of Multigenome Lentiviral Vector Immunizations in Mice This Example demonstrates that immunizing with a multigenome lentiviral vector expressing three tumor associated antigens generates antigen-specific T cell responses against all three tumor antigens targeted in mice.

Multigenome lentiviral vector particle preparations were made using standard transfection protocols with the exception that three vector genome plasmids were used in this experiment. In particular, in this experiment NY-ESO-1, MAGE-A3 and MAGE-A10 lentiviral vector genome plasmids were used to transfect the producer cells. As noted in Example 1, the total amount of lentiviral vector plasmid DNA was kept at 1 mg but split equally between the three plasmids. Thus, in this case, 0.33 mgs of each vector genome plasmid was used for production of the multigenome LV: NY/M3/M10 viral vector preps.

After vector purification, the titers were determined using gene-specific qRT-PCR based on primer sets specific for NY-ESO-1 and MAGE-A3. The results showed that the multigenome LV prep contained vector RNA from these two vector genomes within the expected ratio ranges. Although not specifically measured, the assumption is that the amount of MAGE-A10 vector genome is as expected based on the amount of the two vector genomes that were measured.

TABLE 4

Gene-specific viral titers in a multigenome lentiviral vector preparation

| Prep/Insert | Total Genome Primers (StDev) | NYESO1 Primers (StDev) | MAGEA3 Primers (StDev) | % NYESO1 in Prep | % MAGEA3 in Prep |
| --- | --- | --- | --- | --- | --- |
| 342/GFP | 2.9E+11 (1.8E+10) | | | | |
| 575/NYESO1 | 1.8E+11 (4.1E+09) | 1.9E+11 (1.0E+10) | | 106.9% | |
| 606/MAGEA3 | 2.1E+11 (2.5E+09) | | 2.1E+11 (5.3E+10) | | 97.9% |
| 615/NYESO1 + MAGEA3 | 1.2E+11 (4.5E+09) | 5.1E+10 (1.3E+09) | 5.0E+10 (1.2E+10) | 42.5% | 42% |

BALC/c mice were immunized with homozygous LV (1E10 genomes each prep) encoding NY-ESO-1 (NY) or MAGE-A3 (M3), or with multigenome viral vector preparations of LV material containing both NY-ESO-1 and MAGE-A3 genomes (2E10 total genomes so as to achieve 1E10 of each of NY-ESO-1 or MAGE-A3 genome; per Table 1, based on 50/50 starting vector genome plasmid DNA for each vector genome, 25% of particles will be homozygous for NYESO1 or MAGEA3 and 50% of particles with be heterozygous), or with homozygous NY-ESO-1 and MAGE-A3 LV material ad-mixed together (1E10 genomes of each), or co-immunized with homozygous NY-ESO-1 and MAGE-A3 LV material injected separately (1E10 genomes of each). At 14 days post-immunization T-cell immune responses were assessed using peptide re-stimulation followed by intracellular cytokine staining and flow cytometry. The figures illustrate the mean anti- In this study, on Day 0, BALB/c female mice (n=5 per group) were immunized with 5E9 genomes of lentiviral vector manufactured to deliver NY-ESO-1, MAGE-A3, and MAGE-A10 genes (Multigenome LV: NY/M3/M10) to antigen-presenting cells in vivo. On Day 14, spleens were harvested from immunized mice to determine the development of antigen-specific CD8 T cell responses against the tumor antigens, NY-ESO1, MAGE-A3, and MAGE-A10.

Figure 5A:
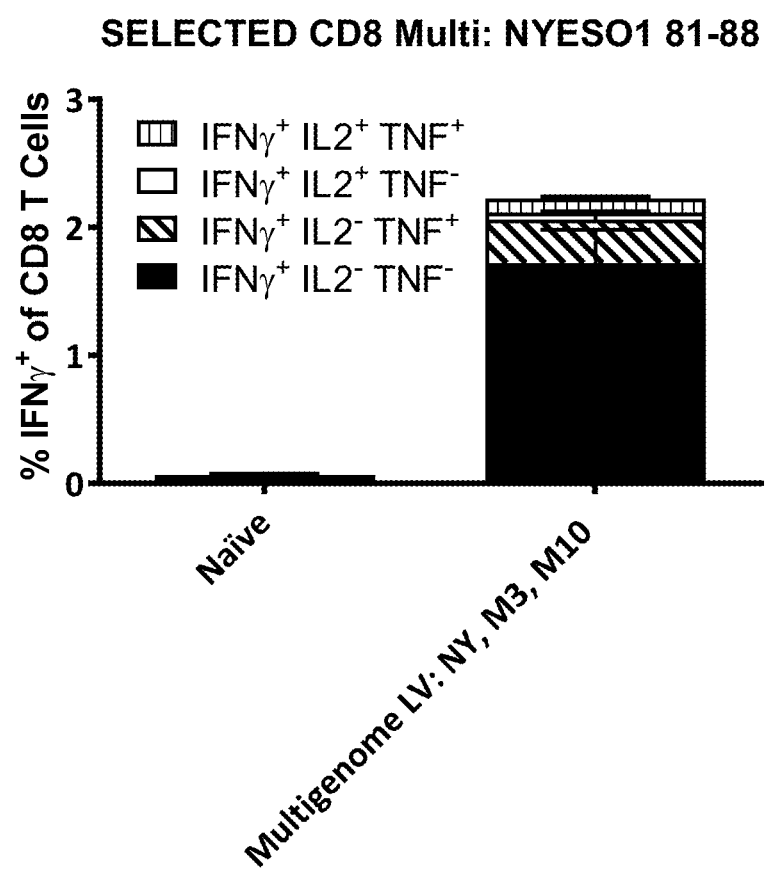
FIGS. 5A-5C contain graphs of antigen-specific CD8 T cell responses from BALB/c female mice injected in the tailbase with a multigenome lentiviral vector preparation to deliver vectors expressing NYESO1/MAGEA3/MAGEA10NYESO1 (FIG. 5A), MAGE A3 (FIG. 5B, and MAGEA10 (FIG. 5C).
Figure 5B:
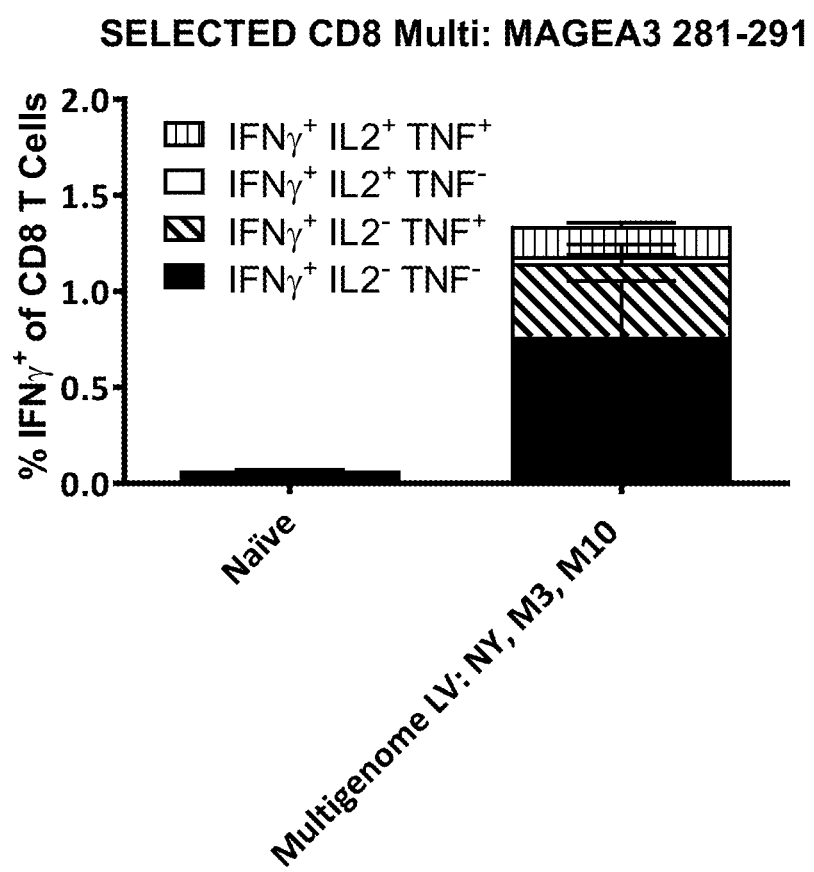
Figure 5C:
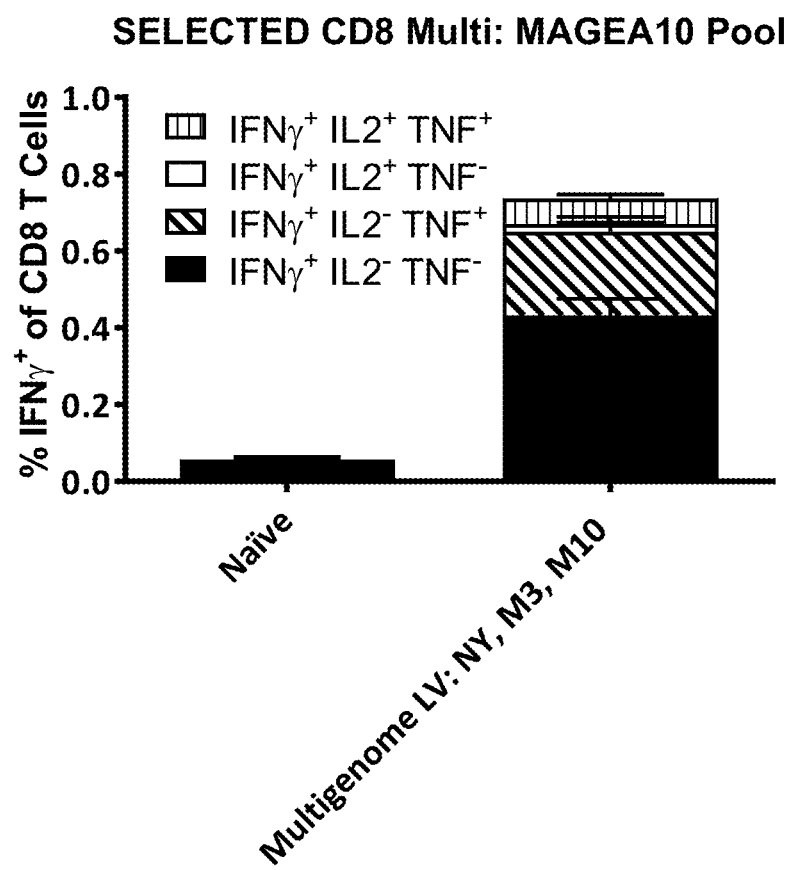

As shown in FIG. 5A-5C, mice immunized with multigenome LV: NY/M3/M10 developed antigen-specific CD8 T cells against all three targeted tumor antigens.

Titrations by qRT-PCR of multiple vector preparations demonstrated that the production yields of multigenome viral vector preparations expressing up to four different TAA (such as NYESO1, MAGE-A3) and two immune modulators (such as IL-12, checkpoint inhibitor etc.) were highly reproducible, both for individual antigen-encoding vector species and for total vector genomes produced. Compared to mice immunized with vectors expressing multiple genes from a single vector genome either as fusion proteins, or separated by 2A endoprotease cleavage sites, or under the control of different IRES motifs, multigenome viral vector prep immunized mice consistently developed antigen-specific T cells against all targeted TAAs.

This Example describes a next generation lentiviral vector system that achieves effective targeting of multiple tumor antigens. The ability to mix multiple lentiviral vector genome plasmids at controllable ratios at the transfection stage of vector production grants otherwise unachievable flexibility to manufacture combinations of multigenome vector preparations highly suitable for use in vivo to induce tumor-specific T cell response and anti-tumor therapy. In particular, this lentiviral vector production system is useful for generating patient-specific lentiviral vectors expressing multiple tumor antigens including neoantigens.

Example 3

In Vivo Immunogenicity Effect of Immunizations Using a Multigenome Lentiviral Vector in Mice The immune response generated following administration of multigenome lentiviral vector expressing multiple tumor antigens and immuno-modulatory factors is investigated.

In this study, on Day 0, BALB/c female mice (n=5 per group) are immunized with multigenome lentiviral vector manufactured to deliver NY-ESO-1, MAGE-A3, and MAGE-A10 genes and one of the following immuno-modulatory factors to antigen-presenting cells in vivo: mIL-12, mIRF3(5D), anti-mPDL1, or anti-mCTLA4. On Day 14, spleens are harvested from immunized mice to determine the development of antigen-specific CD8 T cell responses against the tumor antigens, NY-ESO1, MAGE-A3, and MAGE-A10.

Example 4

In Vivo Therapeutic Efficacy of Immunizations Using a Multigenome Lentiviral Vector in Mice Previous data showed that, when dosed at the same genomes, lentiviral vector particles containing sequences encoding NYESO1 and MAGEA3 on a multicistronic genome separated by a T2A cleavage site (NY-T2A-M3) induced significantly fewer NYESO1 specific CD8 T cells in mice compared to a lentiviral vector encoding only the NYESO1 protein, despite evidence that both proteins were expressed. The mice immunized with the NY-T2A-M3 vectors are able to induce an immune response against MAGEA3. Additionally, the NY-T2A-M3 multicistronic lentiviral vector was shown to be therapeutically ineffective in a mouse tumor model system expressing NYESO1. The experiments in this Example were designed to evaluate the therapeutic efficacy of multigenome viral vector preparations containing NY-ESO-1 and MAGEA3 encoding sequences as compared to the multicistronic NY-T2A-M3 lentiviral vector particles.

BALB/c female mice were inoculated intravenously with CIN.23 cells (CT26 tumor cell line expressing NYESO1). Day 3 post-inoculation, mice were immunized with control vector, LV/NYESO1, admixed LV/NYESO1 and LV/MAGEA3, LV/NY-T2A-M3 (2 antigens on a single genome), or Multigenome LV:NY/M3 vectors (see also Example 1). Day 17 post-inoculation, lungs were harvested for nodule enumeration; splenocytes were stained with NYESO1 peptide MHC multimers for flow cytometry analysis.

Figure 2:
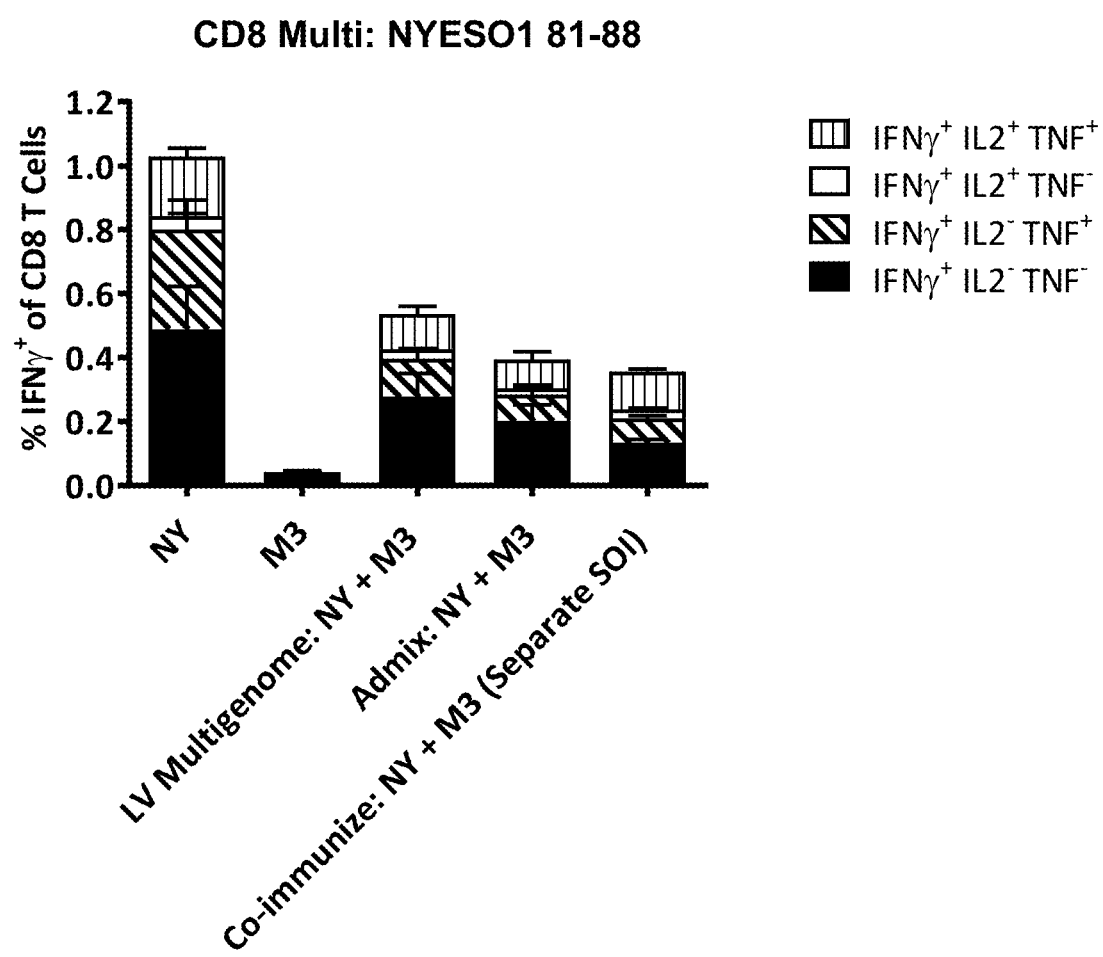
FIG. 2 is a bar graph summarizing the CD8+ T-cell immune responses against NY-ESO-1 in BALB/c mice induced by single, admixed, co-immunized and multigenome viral vector preps.
Figure 6A:
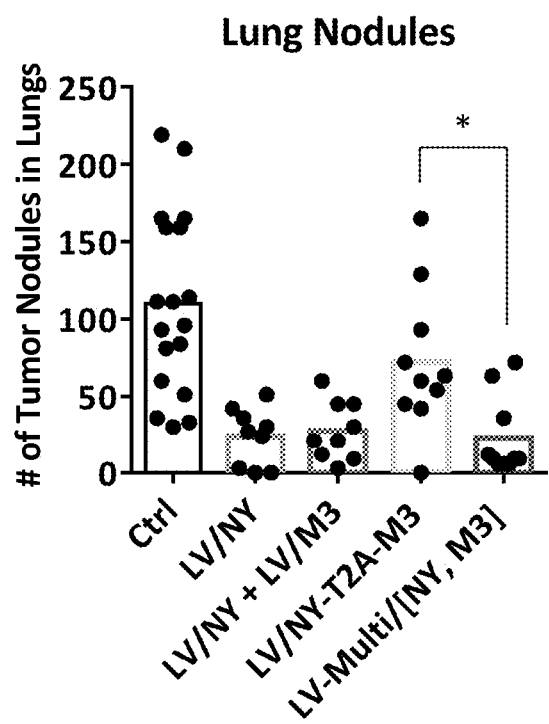
FIGS. 6A-6B are graphs showing reduced tumor nodule formation in the lungs and increased antigen-specific CD8+ T cells of mice treated with multigenome lentiviral vectors. BALB/c females were inoculated intravenously with CIN.23 cells. Day 3 post-inoculation, mice were immunized with lentiviral vectors as shown (see also Example 4). Day 17 post-inoculation, lungs were harvested for nodule enumeration (FIG. 6A); splenocytes were stained with MHC multimers for flow cytometry analysis (FIG. 6B). Error bars represent Mean±SEM. *p<0.05; **p<0.005.
Figure 6B:
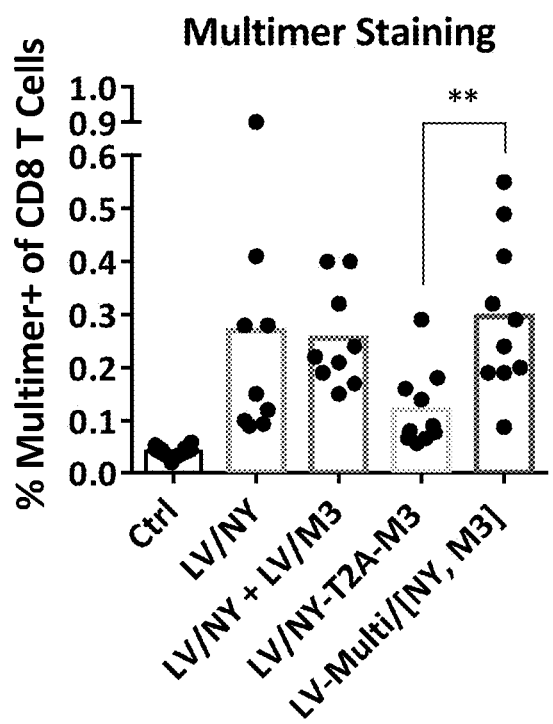
Figure 7A:
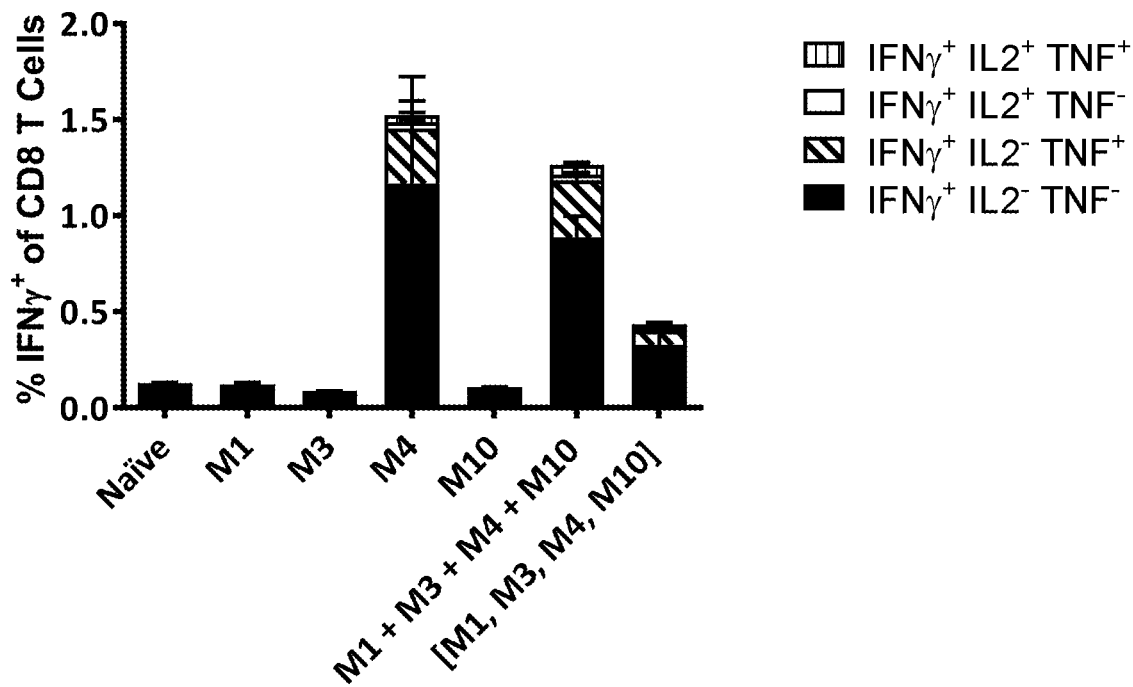
FIGS. 7A-7D are graphs showing antigen-specific CD8 T cell responses from BALB/c mice injected in the tailbase with multigenome lentiviral vector preparation to deliver vectors expressing MAGEA1/A3/A4 and A10 [M1, M3, M4, M10] as compared to mice receiving admixed vectors each expressing a single antigen or mice receiving injections of vectors expressing a single antigen.
Figure 7B:
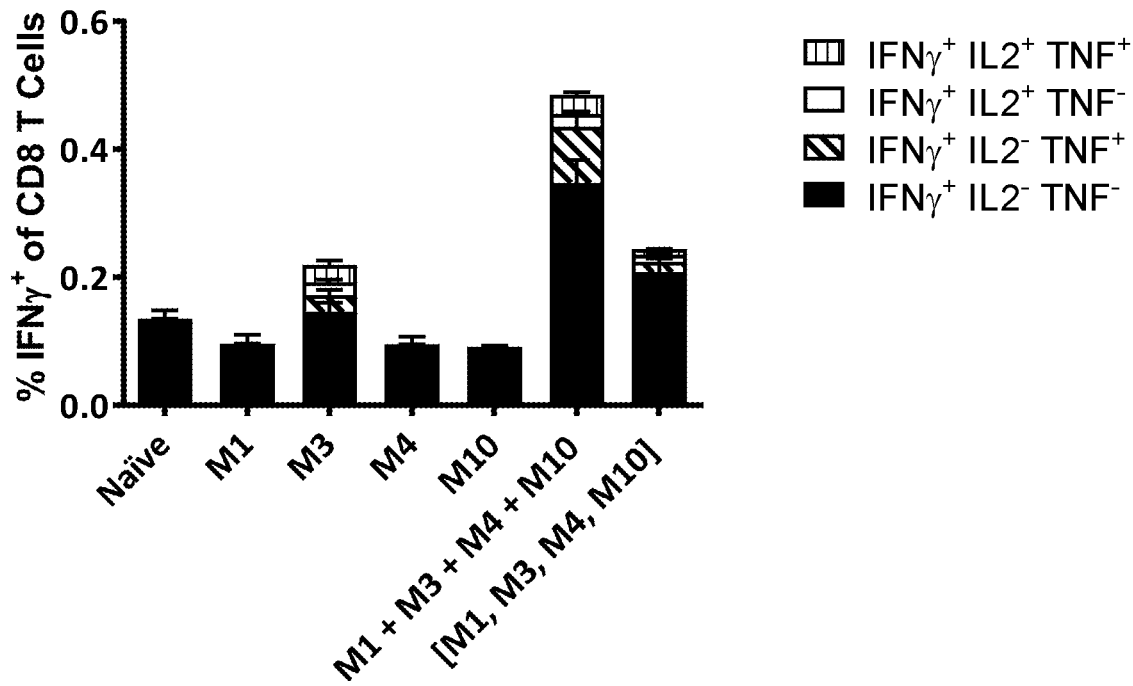
Figure 7C:
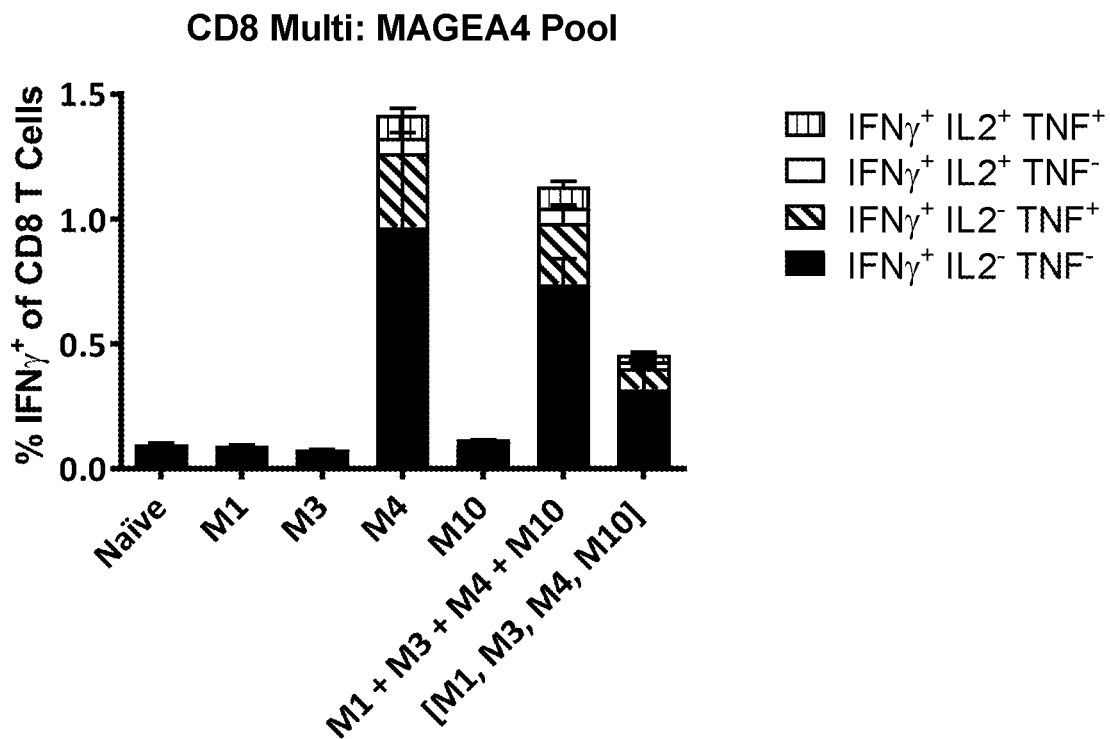
Figure 7D:
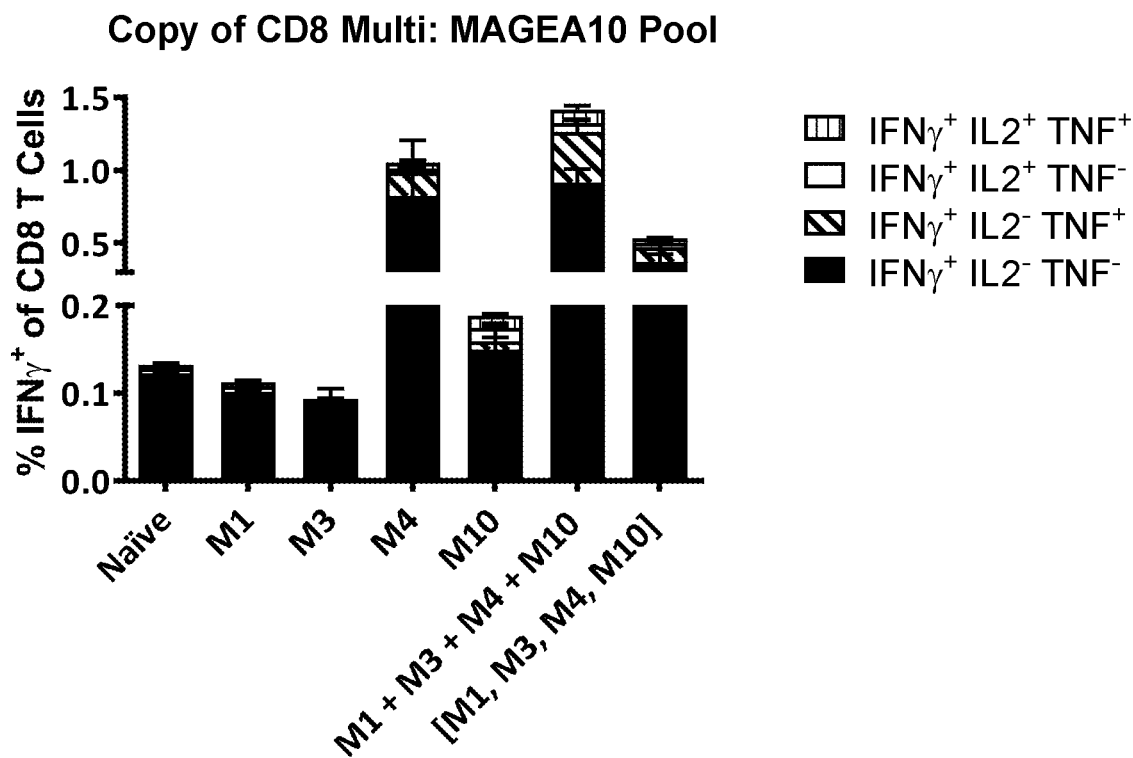

Mice immunized with Multigenome vectors have consistently developed T cells against all targeted TAAs (see e.g., FIGS. 2 and 3). However, confirming previous experiments, the NY-T2A-M3 multicistronic vector did not induce NYESO1 specific T cells (see e.g., FIG. 6B) (note that MAGEA3 T cell induction was not measured in this experiment but has been shown in other experiments (not shown). In this experiment, mice immunized with multigenome vectors exhibited tumor growth control (FIG. 6A) and survival comparable to mice immunized with single vector targeting the tumor antigen of interest, in this case NYESO1. Importantly, the multigenome lentiviral vectors induced a significantly stronger NYESO1 specific CD8 T cell immune response and resulted in a significant reduction in tumor growth as compared to the lentiviral vector expressing both tumor antigens from the same genome (multicistronic genome) (see bars labeled LV/NY-T2A-M3 in FIG. 6 as compared to bars labeled LV-Multi/[NY, M3]).

Example 5

In Vivo Immunogenicity of Immunizations Using a Multigenome (Multimage) Lentiviral Vector in Mice In this Example, the immune response generated following administration of multigenome lentiviral vector expressing multiple MAGE tumor antigens was investigated.

A multigenome vector preparation containing a mixed population of vector particles expressing four different MAGE tumor antigens was prepared essentially as described in Example 1. In this experiment, as in Example 1, 1 mg of lentiviral vector genome plasmid was used for the transfection of packaging cells. Thus, the total amount of vector genome plasmid (1 mg) was kept the same and split between the four lentiviral vector genome plasmids used, so 0.25 mgs of each lentiviral vector genome plasmid (MAGEA1/MAGEA3/MAGEA4/MAGEA10 (all codon optimized) was used for this experiment to generate multigenome lentiviral vector preparations. As described in Example 1, specific genome primers were used to determine the % of each specific genome in the multigenome lentiviral preparation. The results are shown in Table 5 below and based on a 2-fold variability of the assay, the percentages were generally as expected.

TABLE 5

MultiMAGE Lentiviral Vector Preparation Titers
(Gene Specific Single Linearized Standards)

| Viral Prep | Total Genomes | M1 Specific | (M1%) (M1/Total) |
|---|---|---|---|
| M1/M3/M4/M10 | 1.2E+11 | 4.5E+10 | 38.0% |
| M1 | 2.8E+11 | 3.6E+11 | |

| | Total Genomes | M3 Specific | (M3%) (M3/Total) |
|---|---|---|---|
| M1/M3/M4/M10 | 4.6E+10 | 8.94E+09 | 19.3% |
| M3 | 5.60E+10 | 5.2E+10 | |

| | Total Genomes | M4 Specific | (M4%) (M4/Total) |
|---|---|---|---|
| M1/M3/M4/M10 | 6.30E+10 | 9.5E+09 | 15.0% |
| M4 | 9.9E+09 | 1.5E+10 | |

TABLE 5-continued

MultiMAGE Lentiviral Vector Preparation Titers
(Gene Specific Single Linearized Standards)

|             | Total Genomes | M10 Specific | (M10%) (M10/Total) |
|-------------|---------------|--------------|--------------------|
| M1/M3/M4/M10 | 6.4E+10      | 8.6E+09      | 13.6%              |
| M10         | 6.0E+10       | 1.7E+10      |                    |

BALB/c mice (n=5) were immunized as shown in FIG. 7A-7D with the listed vector preparations at a dose of 2.5E9 vector genomes (vg) (vg/specific Ag). Immune response was assessed via in vitro re-stimulation and ICS using the peptide pools as indicated in FIG. 7.

The results show that LV/MageA1 (M1) was not immunogenic in this mouse strain due to the mouse H2K background and that there was no appropriate M1 epitope for this mouse strain MHC haplotype. Further experiments in the Black6 mouse strain showed that the MultiMAGE multigenome vector is immunogenic and generates an anti-M1 immune response in that strain.

Multigenome LV induced a MageA3 (M3) Ag-specific CD8 T cells with no cross reactivity with M1, M4, or M10.

Multigenome LV induced a MAGEA4 (M4) Ag-specific CD8 T cells with cross reactivity with M1 and M10.

MAGEA10 (M10) was minimally immunogenic in this mouse strain.

Thus, this Example confirms that this next generation lentiviral vector system achieves effective expression and induction of immune responses against multiple tumor antigens via a multigenome lentiviral vector preparation.

Example 6

In Vivo Immunogenicity of Immunizations Using a Multigenome Lentiviral Vector Expressing Multiple Antigens and an Immunomodulatory Molecule in Mice This Example demonstrates that including of IL-12 in multigenome lentiviral vector preparations resulted in significantly enhanced CTL responses against the antigens expressed by the multigenome lentiviral vector (e.g., NYESO1 and MAGE-A3), as well as increased vaccine take compared to including a control protein, GFP.

Multigenome lentiviral vector preparations were made essentially as described in Example 1. Plasmids comprising lentiviral genomes encoding NYESO1 (NY), MAGEA3 (M3), MAGEA10 (M10), and mIL12, or GFP as a control, were made using a 1:1:1:3 ratio of plasmid input in the packaging system. Therefore, 0.5 mg of plasmid was split equally between NY, M3 and M10 plasmid and the remaining 0.5 mg plasmid was mIL12 plasmid. Specific and total viral genomes were determined using specific PCR essentially as described in Example 1. Antigen-specific primers were only available for NYESO1 and MAGEA3 in this assay. The results are shown in Table 6 below and demonstrate that the percentages of the specific genomes were close to expected given the ~2-fold variation in the assay.

TABLE 6

Individual gene-specific viral titers

| Viral Prep | Total | NY | M3 | NY % | M3% |
|---|---|---|---|---|---|
| GFP | 2.4E+11 | 0.0E+00 | 0.0E+00 | 0.0% | 0.0% |
| NY, M3, M10, GFP | 4.9E+10 | 1.1E+10 | 1.8E+10 | 22.3% | 36.6% |
| NY, M3, M10, mIL12 | 7.1E+10 | 1.9E+10 | 2.7E+10 | 26.8% | 38.4% |

BALB/c mice (n=7) were immunized with the multigenome preparation containing NY, M3, and M10±GFP or IL-12. Two target dose levels (1E9 or 2E9 vector genomes of Ag) were chosen: "very low" and "low". A two-fold difference was chosen in order to assess the effect of IL-12 per vector genome dose (genomes encoding antigen) and reflecting the approximate variability in the genomes assay.

Figure 8A:
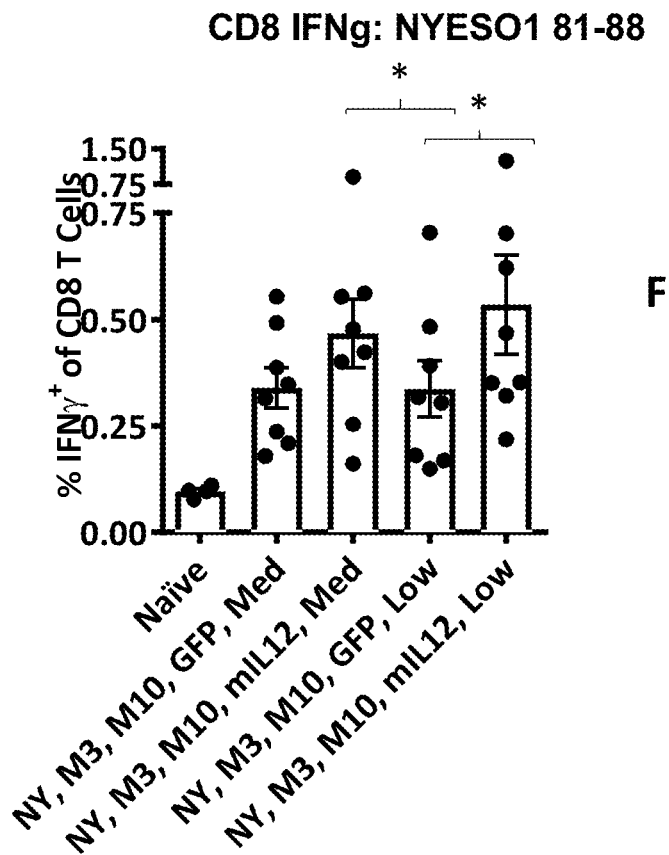
FIGS. 8A-8C are graphs showing antigen-specific CD8 T cell responses in BALB/c mice injected in the tailbase with multigenome lentiviral vector preparation to deliver vectors expressing three antigens (NYESO1/MAGEA3/A10 [NY, M3, M10]) and mIL12 or GFP, at two different doses.
Figure 8B:
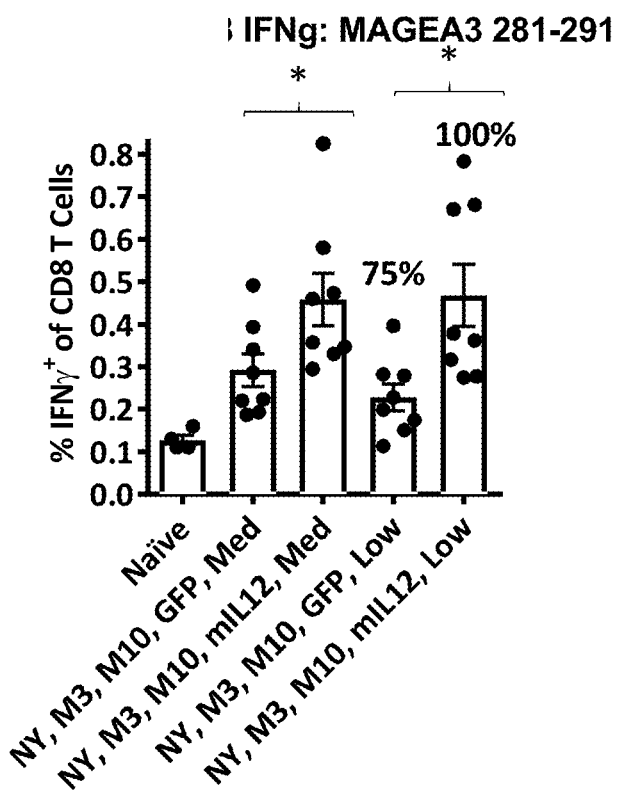
Figure 8C:
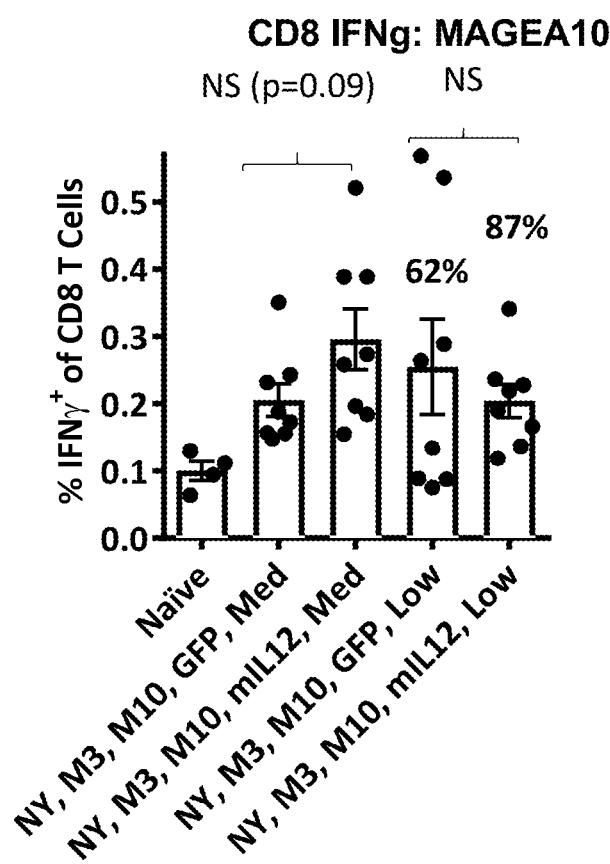

As shown in FIG. 8, including IL-12 in multigenome lentiviral preparations resulted in significantly enhanced CTL responses against NYESO1 and MAGE-A3, as well as increased vaccine take (see bars noted with % vaccine take) compared to addition of GFP. The immune enhancing effect was larger than the effect of a 2-fold dose increase.

Example 7

Production of Multigenome Lentiviral Vector Preparations with Modified Dimer Initiation Signal (DIS) Sequences This Example provides evidence that manipulation of the dimer initiation signal (DIS) sequence of input genomes used in the packaging process for multigenome lentiviral vectors can influence the proportion of heterozygous and homozygous particles in the resulting viral preparation.

Figure 9A:
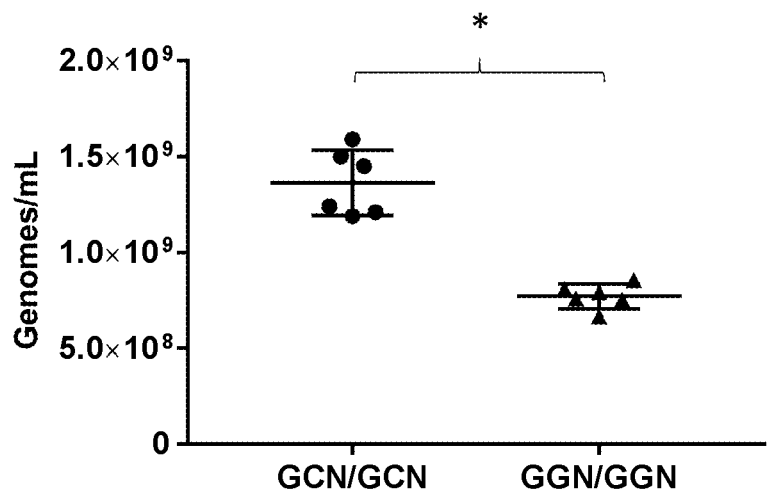
FIGS. 9A-9B show gene-specific genome titers for lentiviral vector preparations made with wildtype and modified DIS sequences.

In the first experiment, lentiviral vector preparations were made with a single input genome (encoding NYESO1) with either the wildtype DIS sequence (GCGCGC, SEQ ID NO:1; viral preparation denoted as GCN/GCN) or with a genome in which the DIS sequence was replaced with a non-palindromic (and non-complementary) DIS (GGGGGG, SEQ ID NO:4; viral preparation denoted as GGN/GGN). Replacing the palindromic DIS sequence with a non-complementing DIS sequence resulted in a significant reduction in lentiviral vector genome titer (p=0.0022, Mann-Whitney test, FIG. 9A). These results illustrated that a palindromic DIS sequence mediates effective dimerization and high-titer lentiviral vector production. The results further showed that genomes lacking a pairing palindromic DIS sequence are still packaged albeit much less efficiently, thereby resulting in lower viral vector titers.

In the next experiment, two input genomes were used (at equal input amounts) to make multigenome lentiviral vector preparations using either the same palindromic DIS sequence on each genome or mutated but complementary DIS sequences on each genome. In the first multigenome preparation, each genome contained the wildtype HIV-1 palindromic DIS sequence (SEQ ID NO:1). The first genome encoded NYESO (denoted GCN in FIG. 9B) and the second encoded MAGEA3 (denoted GCM in FIG. 9). The resulting multigenome preparation is denoted GCN/GCM. In the second multigenome viral vector preparation, the DIS sequence of the first vector genome plasmid, encoding the NYESO1 protein, was mutated to GGGGGG (SEQ ID NO:4; denoted GGN) and the second genome, encoding MAGEA3, contained a DIS sequence mutated to CCCCCC (SEQ ID NO:5; denoted CCM). The resulting multigenome viral preparation is denoted GGN/CCM.

Lentiviral vectors were produced by transfection as described in EXAMPLE 1. The specific genomes present in the resulting multigenome lentiviral vector preparations were then measured using the approach described in EXAMPLE 1 (see e.g., Table 4).

Figure 9B:
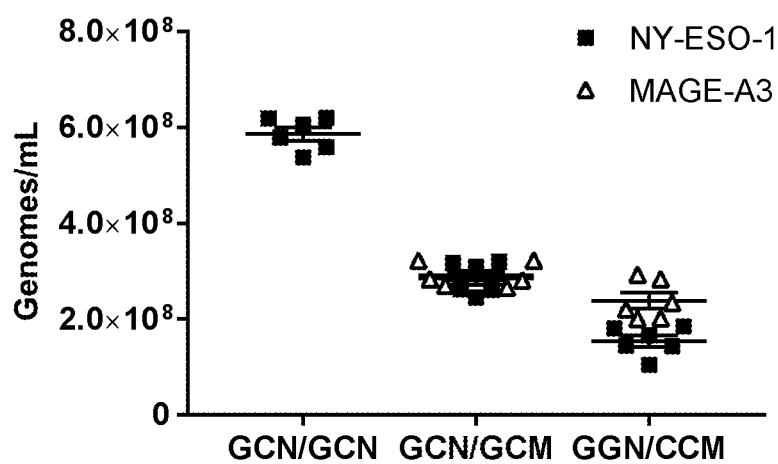

FIG. 9B shows gene-specific vector genome titers of a standard single genome viral preparation using wildtype palindromic DIS (GCN/GCN) as compared to the GCN/GCM multigenome lentiviral vector preparation. Confirming previous experiments, in the GCN/GCM multigenome preparation, made with half NYESO1 and half MAGEA3 input genome plasmid, the NYESO1 genomes detected in the resulting multigenome viral preparation were about half those detected in the NYESO1 single genome viral preparation. The same proportion of MAGEA3 genomes were detected in the GCN/GCM preparation as NYESO1 genomes as would be expected from the 1:1 input ratio of NYESO1/MAGEA3 genomes plasmid used in the packaging process. Based on viral genetics, per Table 1, the resulting preparation should be 25% homozygous for each genome and 50% heterozygous for NYESO1/MAGEA3.

The previous experiment (FIG. 9A), showed that the genomes (GGN/GGN) in the viral preparation made with non-palindromic, non-complementing mutated DIS sequences, did not pair and package efficiently. As shown in FIG. 9B (GGN/CCM) in a multigenome viral preparation made with the mutated DIS sequence, a reduction in NYESO1 and MAGEA3 specific genome titers was observed as compared to the multigenome viral preparation made with a palindromic DIS sequence. This reduction in gene-specific genome titers is presumably due to the reduction in the pairing and packaging of homozygous genomes (GGN/GGN and CCM/CCM). Consequently, one can infer that the resulting percentage of heterozygous particles in the GGN/CCM multigenome viral preparation is increased.

This Example shows that manipulation of DIS sequences can be used to modulate the percentage of heterozygous and homozygous particles in a multigenome viral vector preparation.

The various embodiments described above can be combined to provide further embodiments. All U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A recombinant multigenome retroviral vector preparation comprising:

a. a first retroviral particle comprising two copies of a first retroviral vector genome comprising a first sequence of interest; wherein the first sequence of interest encodes a heterologous protein selected from the group consisting of a tumor antigen, a neoantigen, an infectious disease antigen, an immunomodulatory molecule, a chimeric antigen receptor, a recombinant T cell receptor, and an immunoglobulin antigen-binding domain;

b. a second retroviral particle comprising two copies of a second retroviral vector genome comprising a second sequence of interest; wherein the second sequence of interest encodes a heterologous protein selected from the group consisting of a tumor antigen, a neoantigen, an infectious disease antigen, an immunomodulatory molecule, a chimeric antigen receptor, a recombinant T cell receptor, and an immunoglobulin antigen-binding domain;

c. a third retroviral particle comprising one copy of the first retroviral vector genome comprising a first sequence of interest and one copy of the second retroviral vector genome comprising a second sequence of interest;

wherein the first and second sequences of interest are different; and wherein the retroviral vector preparation is pseudotyped with a heterologous envelope glycoprotein.

2. The recombinant multigenome retroviral vector preparation of claim 1, wherein the heterologous envelope glycoprotein is selected from the group consisting of VSVg, measles envelope glycoprotein, and a Sindbis envelope glycoprotein.

3. The recombinant multigenome retroviral vector preparation of claim 2, wherein the variant Sindbis virus E2 glycoprotein targets the vector to dendritic cells.

4. The recombinant multigenome retroviral vector preparation of any one of claims 1, 2, and 3, wherein the retroviral vector preparation is a lentiviral vector preparation.

5. The recombinant multigenome retroviral vector preparation of any one of claims 1, 2, and 3, wherein the first sequence of interest encodes a tumor-associated antigen or one or more neoantigens and the second sequence of interest encodes an immunomodulatory molecule.

6. The recombinant multigenome retroviral vector preparation of any one of claims 1, 2, and 3, wherein the first sequence of interest encodes a tumor-associated antigen and the second sequence of interest encodes a different tumor-associated antigen.

7. A retroviral vector packaging system for producing a pseudotyped multigenome retroviral vector preparation, comprising:
   a. a first nucleic acid molecule encoding a viral envelope protein;
   b. a second nucleic acid molecule encoding gag and pol proteins;
   c. a third nucleic acid molecule encoding rev;
   d. a fourth nucleic acid molecule comprising a first retroviral vector genome comprising a first sequence of interest; wherein the first sequence of interest encodes a heterologous protein selected from a tumor antigen, a neoantigen, an infectious disease antigen, an immunomodulatory molecule, a chimeric antigen receptor, a recombinant T cell receptor, and an immunoglobulin antigen-binding domain;
   e. a fifth nucleic acid molecule comprising a second retroviral vector genome comprising a second sequence of interest; wherein the second sequence of interest encodes a heterologous protein selected from a tumor antigen, a neoantigen, an infectious disease antigen, an immunomodulatory molecule, a chimeric antigen receptor, a recombinant T cell receptor, and an immunoglobulin antigen-binding domain;
   f. optionally a sixth nucleic acid molecule encoding vpx; and
   g. a packaging cell or cell line.

8. The retroviral vector packaging system of claim 7 wherein the retroviral vector preparation is a lentiviral vector preparation.

9. The retroviral vector packaging system of claim 7 or claim 8 wherein the first sequence of interest encodes a tumor-associated antigen or one or more neoantigens and the second sequence of interest encodes an immunomodulatory molecule.

10. The retroviral vector packaging system of claim 7 wherein the first sequence of interest encodes a tumor-associated antigen and the second sequence of interest encodes a different tumor-associated antigen.

11. The retroviral vector packaging system of claim 7 wherein the first lentiviral vector genome and the second lentiviral vector comprise a palindromic dimer initiation site (DIS) sequence.

12. The retroviral vector packaging system of claim 7 wherein the first lentiviral vector genome comprises a first palindromic DIS sequence and the second lentiviral vector comprise a second palindromic DIS sequence.

13. The retroviral vector packaging system of claim 7 wherein the first lentiviral vector genome comprises a first DIS sequence and the second lentiviral vector comprise a second DIS sequence wherein the first and second DIS sequences are non-palindromic.

14. The retroviral vector packaging system of claim 7 wherein the pol protein has a non-functional integrase.

15. The recombinant multigenome retroviral vector preparation of claim 1, further comprising:
   e. a fourth retroviral particle comprising two copies of a third retroviral vector genome comprising a third sequence of interest;
   f. a fifth retroviral particle comprising one copy of the first retroviral vector genome comprising a first sequence of interest and one copy of the third retroviral vector genome comprising the third sequence of interest; and
   g. a sixth retroviral particle comprising one copy of the second retroviral vector genome comprising a second sequence of interest and one copy of the third retroviral vector genome comprising the third sequence of interest.

16. The recombinant multigenome retroviral vector preparation of claim 1 or claim 15 wherein the first retroviral vector genome comprises about 50% of the vector genomes in the multigenome vector preparation.

17. A multigenome retroviral vector packaging system, comprising:
   a. at least two nucleic acid molecules each comprising a retroviral vector genome comprising a unique sequence of interest; wherein the unique sequence of interest encodes a heterologous protein selected from a tumor antigen, a neoantigen, an infectious disease antigen, an immunomodulatory molecule, a chimeric antigen receptor, a recombinant T cell receptor, and an immunoglobulin antigen-binding domain;
   b. one or more nucleic acid molecules encoding the components necessary to generate pseudotyped retroviral vector particles;
   c. optionally a nucleic acid molecule encoding vpx; and
   d. a packaging cell line.

18. The multigenome retroviral vector packaging system of claim 17, consisting of 2 to 8 nucleic acid molecules each comprising a retroviral vector genome comprising a unique sequence of interest.

19. The multigenome retroviral vector packaging system of claim 18, consisting of 5 nucleic acid molecules each comprising a retroviral vector genome comprising a unique sequence of interest, wherein the relative input ratio of the 5 nucleic acid molecules each comprising a retroviral vector genome comprising a unique sequence of interest is selected from one of the input ratios shown in Table 3.

20. The multigenome retroviral vector packaging system of any one of claims 17, 18, and 19 wherein the components necessary to generate retroviral vector particles include gag, pol, envelope, and optionally rev and/or vpx proteins.

21. The multigenome retroviral vector packaging system of any one of claims 17, 18, and 19 wherein the packaging cell line stably expresses one or more of the components necessary to generate retroviral vector particles.

22. The multigenome retroviral vector packaging system of any one of claims 17, 18, and 19 wherein the retroviral vector genome is a lentiviral vector genome.

23. A method for producing a pseudotyped multigenome retroviral vector preparation comprising culturing the packaging cell line of any one of claims 17, 18, and 19 transfected with the nucleic acids of (a) and (b) and optionally (c).

24. A method of inducing an immune response in a subject comprising administering the multigenome retroviral vector preparation of any one of claims 1, 15, and 16.

25. A method of treating cancer in a subject comprising administering the multigenome retroviral vector preparation of any one of claims 1, 15, and 16.

* * * * *